US011213552B2

(12) United States Patent
Kovarik

(10) Patent No.: US 11,213,552 B2
(45) Date of Patent: *Jan. 4, 2022

(54) METHOD FOR TREATING AN INDIVIDUAL SUFFERING FROM A CHRONIC INFECTIOUS DISEASE AND CANCER

(71) Applicant: Joseph E. Kovarik, Englewood, CO (US)

(72) Inventor: Joseph E. Kovarik, Englewood, CO (US)

(*) Notice: Subject to any disclaimer, the term of this patent is extended or adjusted under 35 U.S.C. 154(b) by 0 days.

This patent is subject to a terminal disclaimer.

(21) Appl. No.: 17/337,600

(22) Filed: Jun. 3, 2021

(65) Prior Publication Data

US 2021/0283196 A1  Sep. 16, 2021

Related U.S. Application Data

(63) Continuation-in-part of application No. 17/027,953, filed on Sep. 22, 2020, now Pat. No. 11,026,982, and a continuation-in-part of application No. 17/023,736, filed on Sep. 17, 2020, now abandoned, which is a continuation-in-part of application No. 17/011,175, filed on Sep. 3, 2020, said application No. 17/027,953 is a continuation-in-part of application No. 16/917,096, filed on Jun. 30, 2020, now Pat. No. 10,940,169, application No. 17/337,600, which is a continuation-in-part of application No. 16/904,056, filed on Jun. 17, 2020, said application No. 16/917,096 is a continuation-in-part of application No. 16/782,364, filed on Feb. 5, 2020, now Pat. No. 10,835,560, application No. 17/337,600, which is a continuation-in-part of application No. 16/776,861, filed on Jan. 30, 2020, now Pat. No. 10,864,109, said application No. 17/011,175 is a continuation-in-part of application No. 16/722,117, filed on Dec. 20, 2019, now Pat. No. 10,842,834, application No. 17/337,600, which is a continuation-in-part of application No. 16/426,346, filed on May 30, 2019, said application No. 16/782,364 is a continuation-in-part of application No. 16/423,375, filed on May 28, 2019, now Pat. No. 10,555,976, said application No. 16/782,364 is a continuation-in-part of application No. 16/423,375, filed on May 28, 2019, now Pat. No. 10,555,976, said application No. 16/722,117 is a continuation-in-part of application No. 16/229,252, filed on Dec. 21, 2018, now Pat. No. 10,512,661, said application No. 16/423,375 is a continuation of application No. 16/160,336, filed on Oct. 15, 2018, now Pat. No. 10,314,866, said application No. 16/776,861 is a continuation of application No. 16/142,171, filed on Sep. 26, 2018, now Pat. No. 10,548,761, application No. 17/337,600, which is a continuation-in-part of application No. 16/037,053, filed on Jul. 17, 2018, said application No. 16/904,056 is a continuation-in-part of application No. 15/983,250, (Continued)

(51) Int. Cl.
| | |
|---|---|
| A61K 35/74 | (2015.01) |
| A61K 31/715 | (2006.01) |
| A61K 31/58 | (2006.01) |
| A61K 38/17 | (2006.01) |
| A61K 35/00 | (2006.01) |

(52) U.S. Cl.
CPC .............. *A61K 35/74* (2013.01); *A61K 31/58* (2013.01); *A61K 31/715* (2013.01); *A61K 38/1709* (2013.01); *A61K 38/1758* (2013.01); *A61K 2035/11* (2013.01)

(58) Field of Classification Search
None
See application file for complete search history.

(56) References Cited

U.S. PATENT DOCUMENTS

| 5,518,733 A | 5/1996 | Lamonthe et al. |
|---|---|---|
| 6,287,610 B1 | 9/2001 | Bowling et al. |

(Continued)

FOREIGN PATENT DOCUMENTS

| WO | WO 2006/07922 | 1/2006 |
|---|---|---|
| WO | WO 2011029701 | 3/2011 |

(Continued)

OTHER PUBLICATIONS

U.S. Appl. No. 10/687,975, filed Jun. 23, 2020, Kovarik.
U.S. Appl. No. 10/716,815, filed Jul. 21, 2020, Kovarik et al.

*Primary Examiner* — Brian Gangle
(74) *Attorney, Agent, or Firm* — Sheridan Ross P.C.

(57) ABSTRACT

A method for treating an individual suffering from a chronic infectious disease and who has cancer employs a CRISPR system to selectively kill or reduce the numbers of pathogenic bacteria within the individual and the individual is then administered an immune checkpoint inhibitor. In particular embodiments, the pathogenic bacteria is one of *E. coli, Pseudomonas aeruginosa* and *Klebsiella* bacteria, and the checkpoint inhibitor is selected from the group consisting of nivolumab, pembrolizumab, pidilizumab, AMP-224, AMP-514, STI-A1110, TSR-042, RG-7446, BMS-936559, MEDI-4736, MSB-0020718C, AUR-012 and STI-A1010. Further embodiments include enhancing the growth of a second bacteria in the individual, such bacteria including *Akkermansia, Bacteroides, Bifidobacterium, Clostridium, Enterococcus, Fusobacterium, Coprococcus, Lactobacillus, Propionibacterium, Ruminococcus, Veillonella, Prevotella, Escherichia* and *Streptococcus*. The CRISPR system may include Cas9, Cpf1 and Cas3, and may be delivered using a bacteriophage.

20 Claims, 7 Drawing Sheets

Related U.S. Application Data filed on May 18, 2018, now Pat. No. 10,687,975, said application No. 16/426,346 is a continuation of application No. 15/639,767, filed on Jun. 30, 2017, now Pat. No. 10,314,865, which is a continuation-in-part of application No. 15/437,976, filed on Feb. 21, 2017, now Pat. No. 9,730,967, said application No. 16/160,336 is a continuation of application No. 15/403,823, filed on Jan. 11, 2017, now Pat. No. 10,111,913, said application No. 16/142,171 is a continuation-in-part of application No. 15/395,419, filed on Dec. 30, 2016, now Pat. No. 10,086,018, said application No. 16/229,252 is a continuation-in-part of application No. 15/392,173, filed on Dec. 28, 2016, now Pat. No. 10,245,288, said application No. 15/983,250 is a continuation-in-part of application No. 15/384,716, filed on Dec. 20, 2016, now Pat. No. 9,987,224, application No. 17/337,600, which is a continuation-in-part of application No. 15/270,034, filed on Sep. 20, 2016, now Pat. No. 9,750,802, said application No. 15/437,976 is a continuation-in-part of application No. 15/228,454, filed on Aug. 4, 2016, now Pat. No. 9,585,920, said application No. 15/228,454 is a continuation-in-part of application No. 14/954,074, filed on Nov. 30, 2015, now Pat. No. 9,457,077, said application No. 15/270,034 is a continuation-in-part of application No. 14/954,074, filed on Nov. 30, 2015, now Pat. No. 9,457,077.

(60) Provisional application No. 62/296,186, filed on Feb. 17, 2016, provisional application No. 62/275,341, filed on Jan. 6, 2016, provisional application No. 62/274,550, filed on Jan. 4, 2016, provisional application No. 62/387,405, filed on Dec. 24, 2015.

(56) References Cited

U.S. PATENT DOCUMENTS

| | | |
|---|---|---|
| 6,569,474 B2 | 5/2003 | Clayton et al. |
| 7,267,975 B2 | 9/2007 | Strobel et al. |
| 7,820,420 B2 | 10/2010 | Whitlock |
| 8,034,601 B2 | 10/2011 | Boileau et al. |
| 8,349,313 B2 | 1/2013 | Smith et al. |
| 8,481,299 B2 | 7/2013 | Gueniche |
| 8,685,389 B2 | 4/2014 | Baur |
| 8,758,764 B2 | 6/2014 | Masignani et al. |
| 8,815,538 B2 | 8/2014 | Lanzalaco et al. |
| 8,951,775 B2 | 2/2015 | Castiel |
| 9,011,834 B1 | 4/2015 | McKenzie |
| 9,028,841 B2 | 5/2015 | Henn et al. |
| 9,044,420 B2 | 6/2015 | Dubensky, Jr. |
| 9,234,204 B2 | 1/2016 | Qvit-Raz |
| 9,288,981 B2 | 3/2016 | Gandhi et al. |
| 9,314,489 B2 | 4/2016 | Kelly et al. |
| 9,445,936 B2 | 9/2016 | Kovarik |
| 9,457,077 B2 | 10/2016 | Kovarik |
| 9,585,920 B2 | 3/2017 | Kovarik et al. |
| 9,730,967 B2 | 8/2017 | Kovarik et al. |
| 9,750,802 B2 | 9/2017 | Kovarik |
| 9,987,224 B2 | 6/2018 | Kovarik |
| 10,086,018 B2 | 10/2018 | Kovarik |
| 10,111,913 B2 | 10/2018 | Kovarik |
| 10,245,288 B2 | 4/2019 | Kovarik |
| 10,314,865 B2 | 6/2019 | Kovarik et al. |
| 10,314,866 B2 | 6/2019 | Kovarik |
| 10,512,661 B2 | 12/2019 | Kovarik |
| 10,548,761 B2 | 2/2020 | Kovarik |
| 10,683,323 B2 | 6/2020 | Prakash et al. |
| 10,760,075 B2 | 9/2020 | Sommer et al. |
| 11,026,982 B2 | 6/2021 | Kovarik |
| 2002/0009520 A1 | 1/2002 | Clayton et al. |
| 2003/0206995 A1 | 11/2003 | Bowling et al. |
| 2007/0054008 A1 | 3/2007 | Clayton et al. |
| 2007/0123448 A1 | 5/2007 | Kaplan et al. |
| 2007/0148136 A1 | 6/2007 | Whitlock et al. |
| 2009/0205083 A1 | 8/2009 | Gupta et al. |
| 2010/0081681 A1 | 4/2010 | Blagosklonny |
| 2012/0142548 A1 | 6/2012 | Corsi et al. |
| 2012/0276143 A1 | 11/2012 | O'Mahony |
| 2012/0276149 A1 | 11/2012 | Littman |
| 2012/0283269 A1 | 11/2012 | Blagosklonny |
| 2012/0301452 A1 | 11/2012 | Gueniche et al. |
| 2013/0157876 A1 | 6/2013 | Lynch |
| 2013/0225440 A1 | 8/2013 | Freidman et al. |
| 2013/0259834 A1 | 10/2013 | Klaenhammer et al. |
| 2013/0310416 A1 | 11/2013 | Blagosklonny |
| 2013/0326645 A1 | 12/2013 | Cost et al. |
| 2014/0030332 A1 | 1/2014 | Baron et al. |
| 2014/0044677 A1 | 2/2014 | Raz et al. |
| 2014/0045744 A1 | 2/2014 | Gordon |
| 2014/0065209 A1 | 3/2014 | Putaala et al. |
| 2014/0068797 A1 | 3/2014 | Doudna et al. |
| 2014/0255351 A1 | 9/2014 | Berstad et al. |
| 2014/0294915 A1 | 10/2014 | Barreca et al. |
| 2014/0296139 A1 | 10/2014 | Cohen et al. |
| 2014/0349405 A1 | 11/2014 | Sontheimer et al. |
| 2014/0377278 A1 | 12/2014 | Elinav et al. |
| 2015/0004130 A1 | 1/2015 | Faber et al. |
| 2015/0017227 A1 | 1/2015 | Kim |
| 2015/0064138 A1 | 3/2015 | Lu |
| 2015/0071957 A1 | 3/2015 | Kelly |
| 2015/0086581 A1 | 3/2015 | Li |
| 2015/0132263 A1 | 5/2015 | Liu |
| 2015/0190435 A1 | 7/2015 | Henn |
| 2015/0202136 A1 | 7/2015 | Lanzalaco et al. |
| 2015/0259728 A1 | 9/2015 | Cutliffe et al. |
| 2015/0353901 A1 | 12/2015 | Liu et al. |
| 2015/0361436 A1 | 12/2015 | Hitchcock et al. |
| 2015/0374607 A1 | 12/2015 | Lanzalaco et al. |
| 2016/0000754 A1 | 1/2016 | Stamets |
| 2016/0000841 A1 | 1/2016 | Yamamoto et al. |
| 2016/0008412 A1 | 1/2016 | Putaala et al. |
| 2016/0024510 A1 | 1/2016 | Bikard et al. |
| 2016/0040216 A1 | 2/2016 | Wilder |
| 2016/0069921 A1 | 3/2016 | Holmes et al. |
| 2016/0089315 A1 | 3/2016 | Kleinberg et al. |
| 2016/0095316 A1 | 4/2016 | Goodman et al. |
| 2016/0122806 A1 | 5/2016 | Amini et al. |
| 2016/0120915 A1 | 6/2016 | Blaser et al. |
| 2016/0151427 A1 | 6/2016 | Whitlock et al. |
| 2016/0151428 A1 | 6/2016 | Bryann et al. |
| 2016/0158294 A1 | 6/2016 | Von Maltzahn |
| 2016/0168594 A1 | 6/2016 | Zhang et al. |
| 2016/0175327 A1 | 6/2016 | Adams et al. |
| 2016/0199424 A1 | 7/2016 | Berry et al. |
| 2016/0206666 A1 | 7/2016 | Falb |
| 2016/0206668 A1 | 7/2016 | Kort et al. |
| 2016/0243132 A1 | 8/2016 | Adams et al. |
| 2016/0271189 A1 | 9/2016 | Cutcliffe |
| 2016/0314281 A1 | 10/2016 | Apte |
| 2017/0014341 A1 | 1/2017 | Armer et al. |
| 2017/0027914 A1 | 2/2017 | Qi |
| 2017/0079947 A1 | 12/2017 | Richards |
| 2018/0015131 A1 | 1/2018 | Gajewski et al. |
| 2018/0140698 A1 | 5/2018 | Clube et al. |
| 2018/0258100 A1 | 9/2018 | Gregory |
| 2018/0371405 A1 | 12/2018 | Barrangou et al. |
| 2019/0000815 A1 | 1/2019 | Melin |
| 2019/0059314 A1 | 2/2019 | Aharoni |
| 2019/0388471 A1 | 12/2019 | June |
| 2020/0009185 A1 | 1/2020 | Shin |
| 2020/0009268 A1 | 1/2020 | Scholz |
| 2020/0032224 A1 | 1/2020 | Schaeffer et al. |
| 2020/0179460 A1 | 6/2020 | Kovarik |

(56) References Cited

U.S. PATENT DOCUMENTS

2020/0190494 A1  6/2020  Hou et al.
2020/0199555 A1  6/2020  Zhang

FOREIGN PATENT DOCUMENTS

| WO | WO 2013026000   | 2/2013  |
|----|-----------------|---------|
| WO | PCT/US2014/036849 | 11/2014 |
| WO | WO2015069682 A2 | 5/2015  |
| WO | WO2017211753    | 12/2017 |

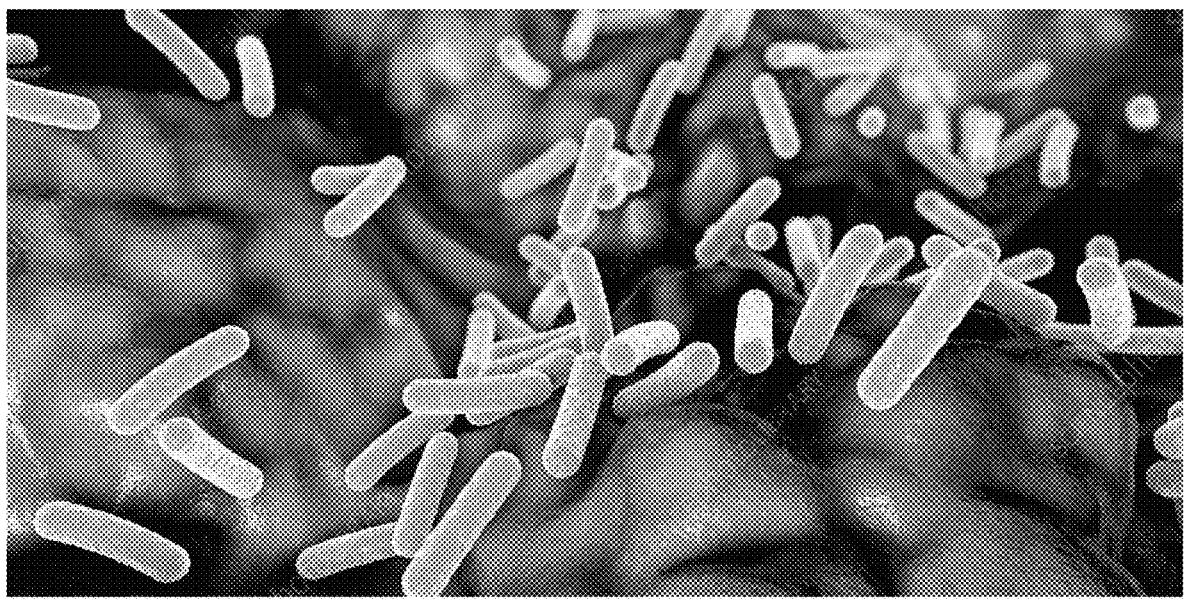
Fig. 1. - *Faecalibacterium prausnitzii*
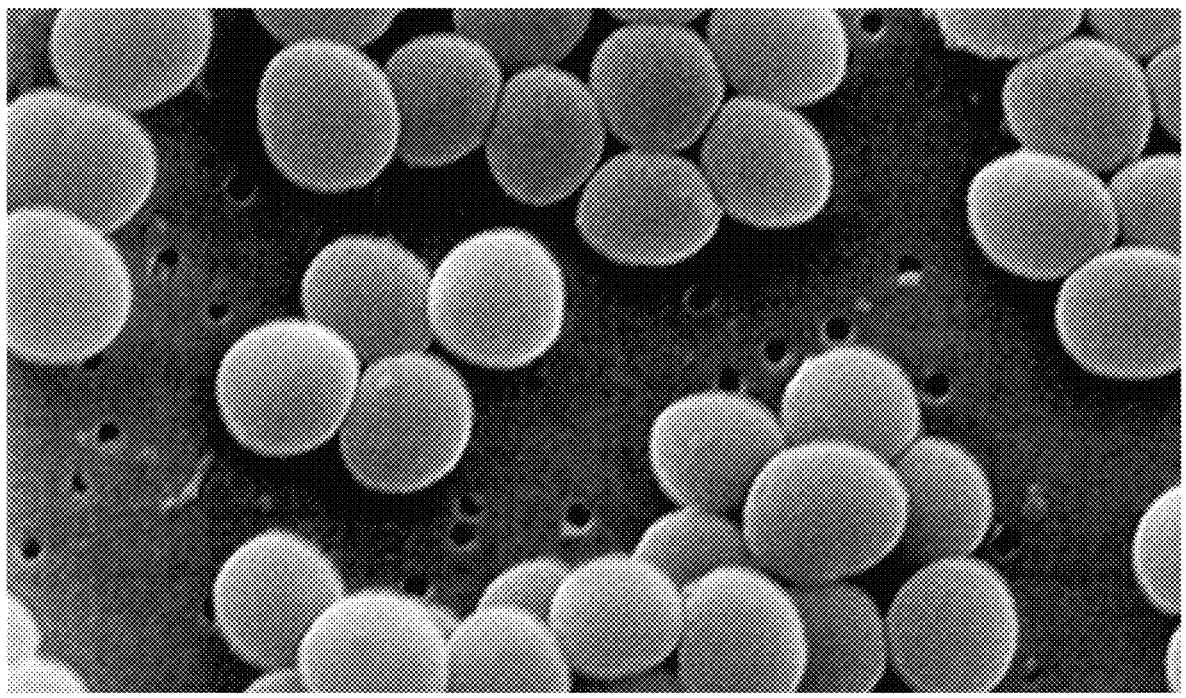
Fig. 2 - *Akkermansia muciniphila*

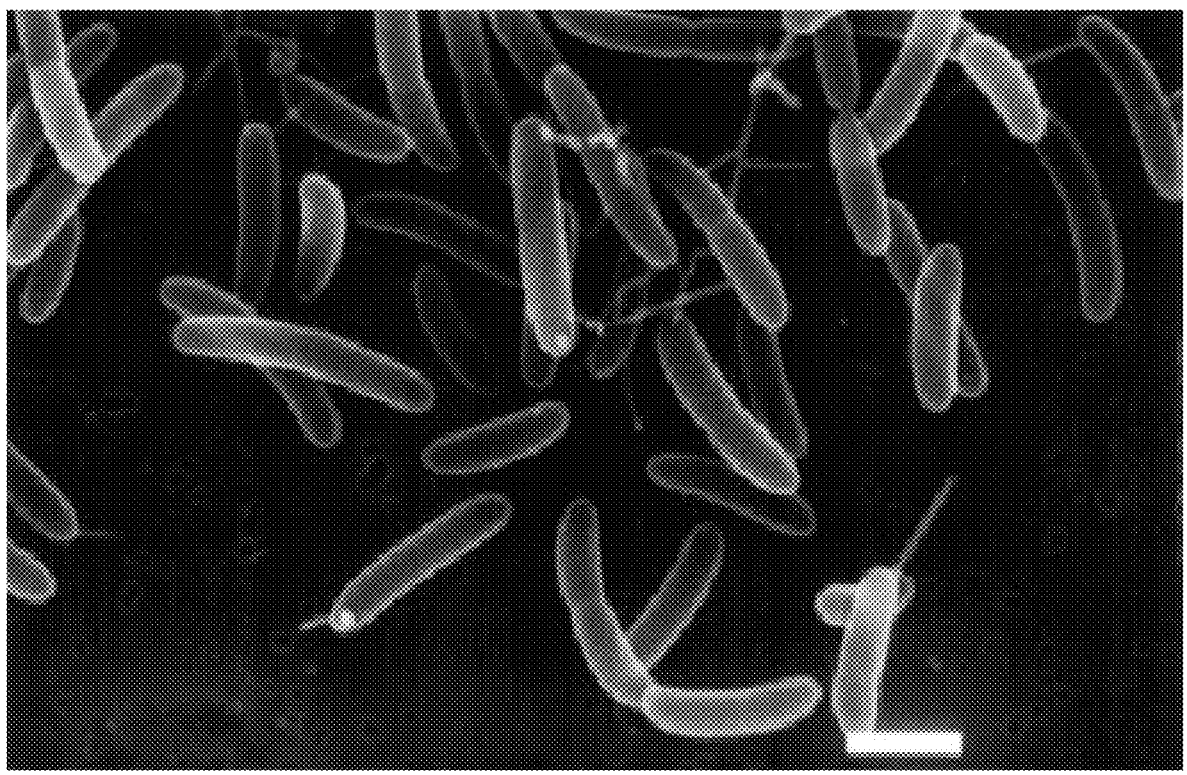
Fig. 3 - Roseburia

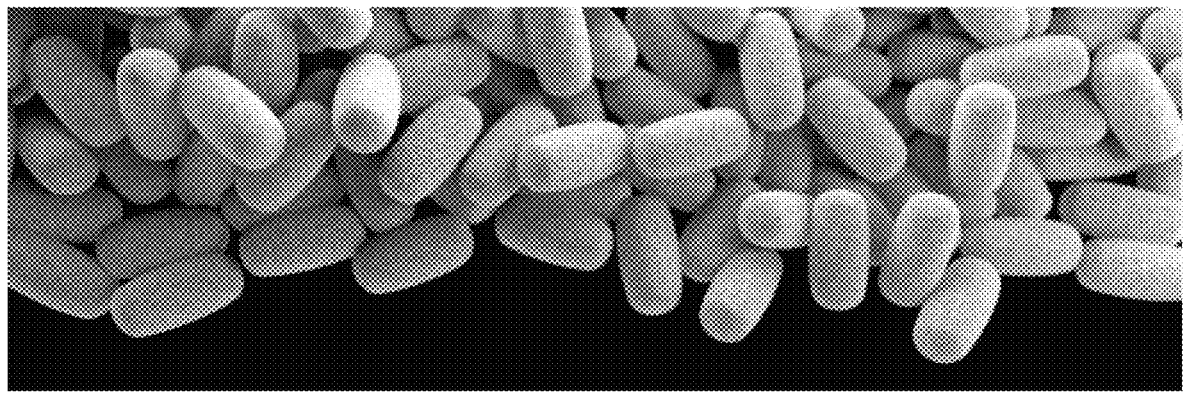
Fig. 4 - *Clostridium*
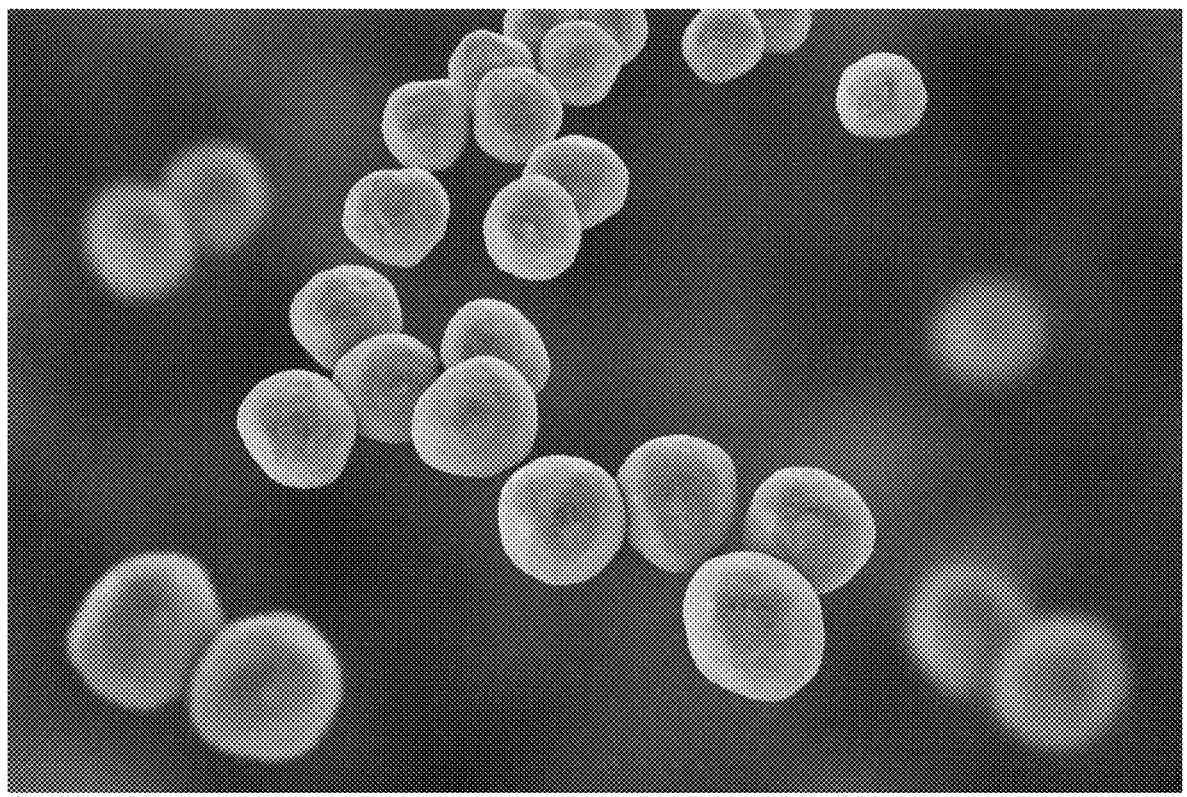
Fig. 5 - *Veillonella*

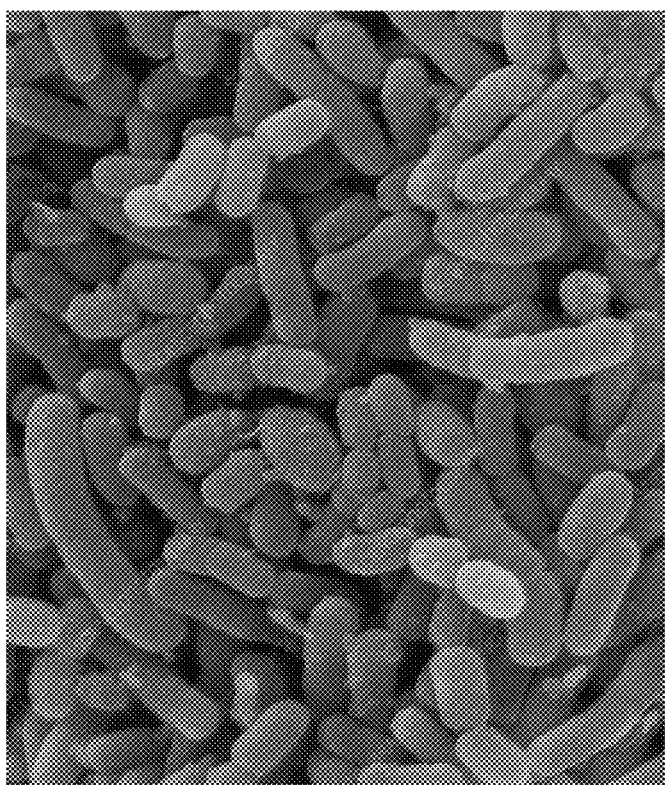
Fig. 6 – *Prevotella*
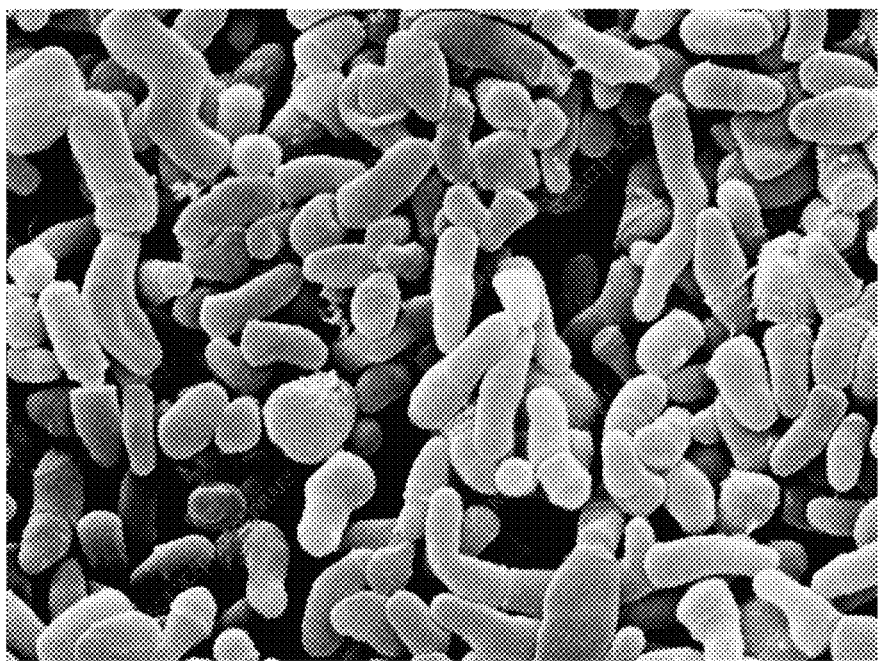
Fig. 7 – *Propionibacterium*

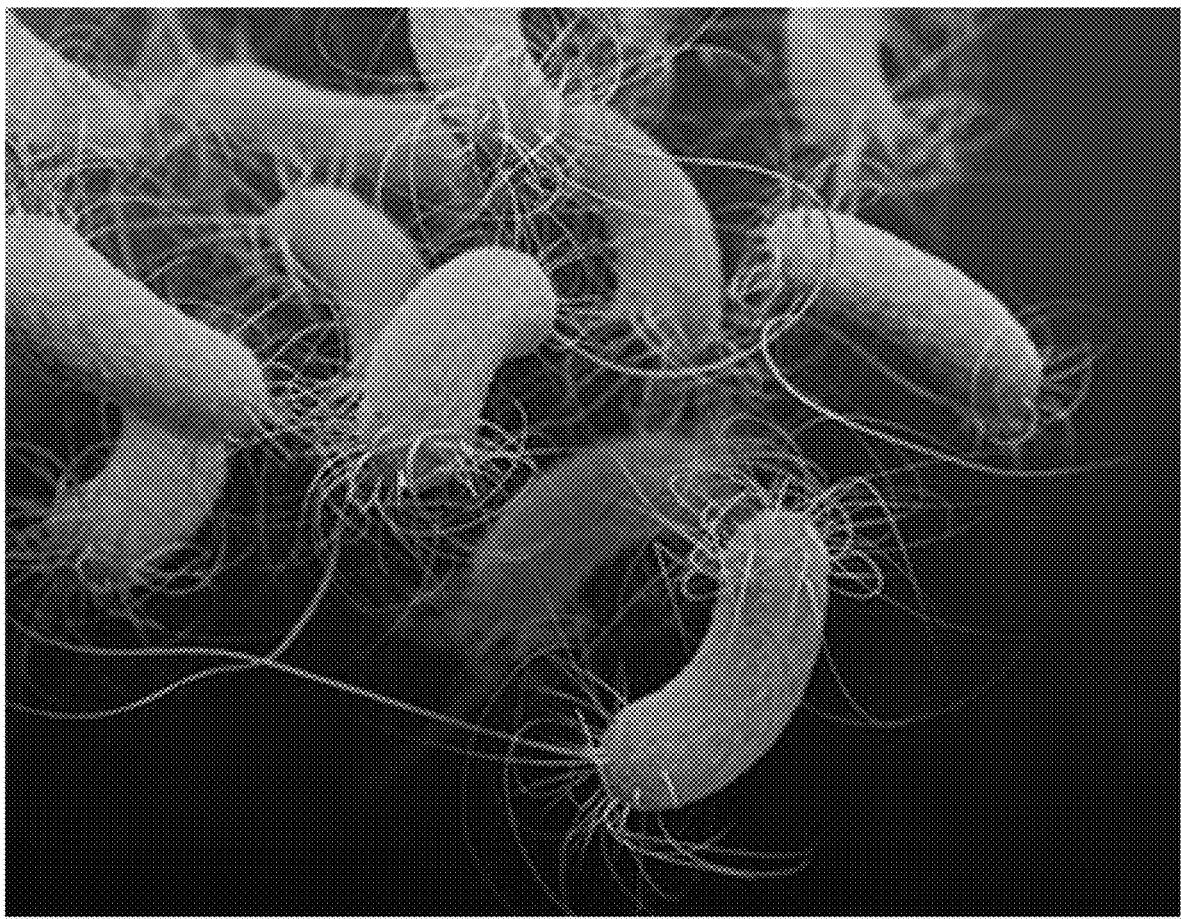
Fig. 8 - *Pseudomonas aeuroginosa*

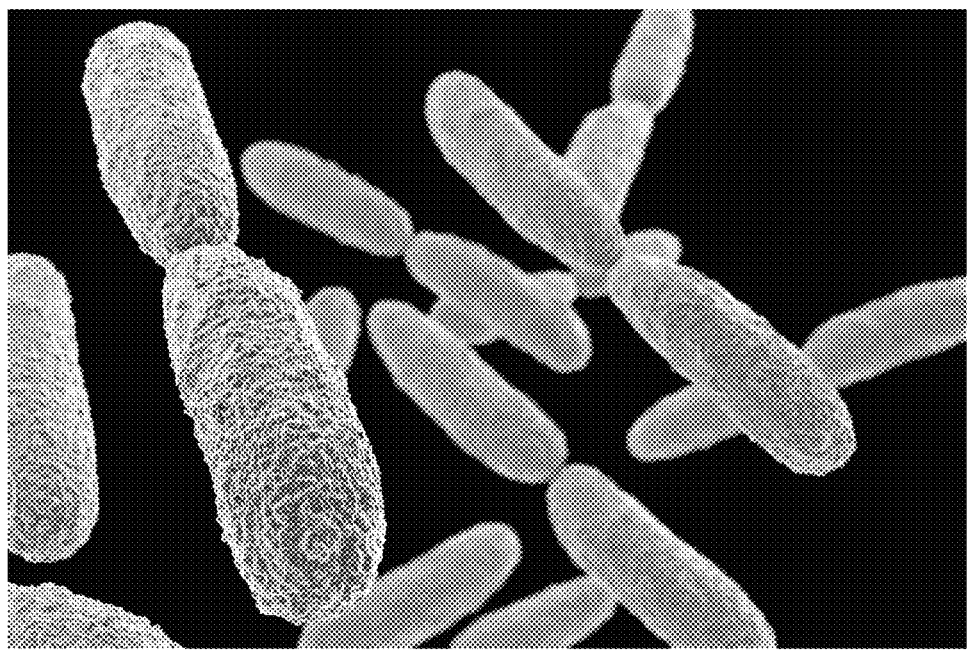
Fig. 9 – *Klebsiella*
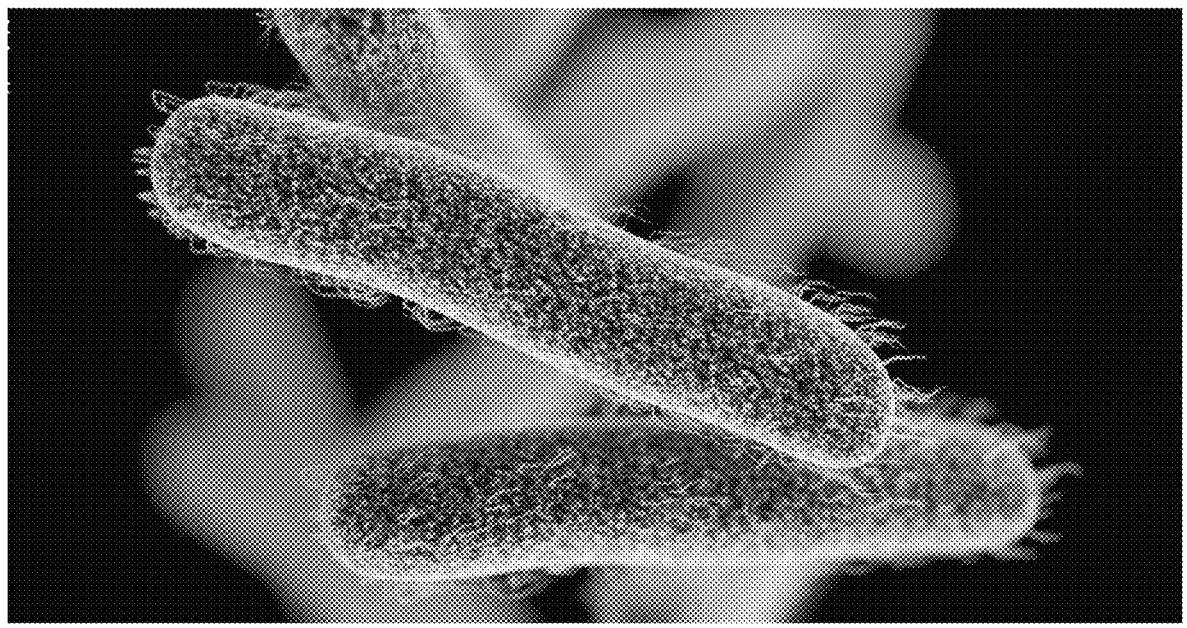
Fig. 10 – Shignella

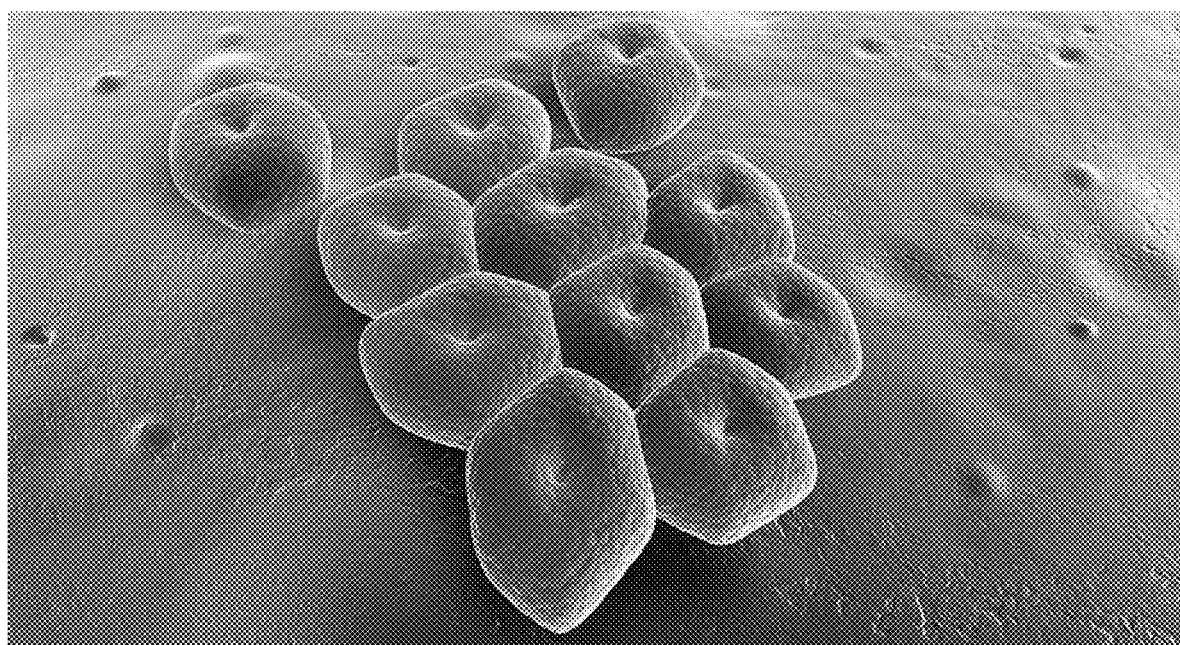
Fig. 11 - *Acinetobacter baumannii*

METHOD FOR TREATING AN INDIVIDUAL SUFFERING FROM A CHRONIC INFECTIOUS DISEASE AND CANCER

RELATED APPLICATIONS

This application is a continuation-in-part of U.S. patent application Ser. No. 17/027,953, filed on Sep. 22, 2020 (now U.S. Pat. No. 11,026,982, issued Jun. 8, 2021), which is a continuation-in-part of U.S. patent application Ser. No. 16/917,096, filed Jun. 30, 2020 (now U.S. Pat. No. 10,940,169, issued Mar. 9, 2021), which is a a continuation-in-part of U.S. patent application Ser. No. 16/782,364, filed Feb. 5, 2020 (now U.S. Pat. No. 10,835,560, issued Nov. 17, 2020), which is a continuation-in-part of U.S. patent application Ser. No. 16/423,375, filed May 28, 2019 (now U.S. Pat. No. 10,555,976, issued Feb. 11, 2020), which is a continuation of U.S. patent application Ser. No. 16/160,336, filed Oct. 15, 2018 (now U.S. Pat. No. 10,314,866, issued Jun. 11, 2019), which is a continuation of U.S. patent application Ser. No. 15/403,823, filed Jan. 11, 2017 (now U.S. Pat. No. 10,111,913, issued Oct. 30, 2018), which is a non-provisional of U.S. Provisional Patent Application Ser. No. 62/296,186, filed on Feb. 17, 2016.

This application is a continuation-in-part of U.S. patent application Ser. No. 16/426,346, filed May 30, 2019 (now U.S. Pat. No. 10,716,815, issued Jul. 20, 2020), which is a continuation of U.S. patent application Ser. No. 15/639,767, filed Jun. 30, 2017 (now issued U.S. Pat. No. 10,314,865, issuing Jun. 11, 2019), which is a continuation-in-part of U.S. patent application Ser. No. 15/437,976, filed Feb. 21, 2017 (now U.S. Pat. No. 9,730,967, issued Aug. 15, 2017), which is a continuation-in-part application of U.S. patent application Ser. No. 15/228,454, filed Aug. 4, 2016 (now U.S. Pat. No. 9,585,920, issued Mar. 7, 2017), which is a continuation-in-part application of U.S. patent application Ser. No. 14/954,074, filed on Nov. 30, 2015 (now issued U.S. Pat. No. 9,457,077, issued Oct. 4, 2016).

This application is a continuation-in-part application of U.S. patent application Ser. No. 16/776,861, filed Jan. 30, 2020, which is a continuation of U.S. patent application Ser. No. 16/142,171, filed Sep. 26, 2018 (now U.S. Pat. No. 10,548,761, issued Feb. 4, 2020), which is a continuation-in-part of U.S. patent application Ser. No. 15/395,419, filed Dec. 30, 2016 (now U.S. Pat. No. 10,086,018, issued Oct. 2, 2018), which is a non-provisional of U.S. Provisional Patent Application Ser. No. 62/274,550, filed on Jan. 4, 2016.

This application is a continuation-in-part application of U.S. patent application Ser. No. 17/023,736, filed Sep. 17, 2020, which is a continuation-in-part of U.S. patent application Ser. No. 17/011,175, filed Sep. 3, 2020, which is a continuation-in-part of U.S. patent application Ser. No. 16/722,117, filed Dec. 20, 2019 (now U.S. Pat. No. 10,842,834, issued Nov. 24, 2020), which is a continuation-in-part of U.S. patent application Ser. No. 16/229,252, filed Dec. 21, 2018 (now U.S. Pat. No. 10,512,661, issued Dec. 24, 2019), which is a continuation-in-part of U.S. patent application Ser. No. 15/392,173, filed Dec. 28, 2016 (now U.S. Pat. No. 10,245,288, issued Apr. 2, 2019), which is a non-provisional of U.S. Provisional Patent Application Ser. No. 62/275,341, filed on Jan. 6, 2016.

This application is a continuation-in-part of U.S. patent application Ser. No. 16/904,056, filed Jun. 17, 2020, which is a continuation-in-part of U.S. patent application Ser. No. 15/983,250 filed on May 18, 2018 (now U.S. Pat. No. 10,687,975, issued Jun. 23, 2020), which is a continuation-in-part of U.S. patent application Ser. No. 15/384,716 filed on Dec. 20, 2016 (now issued U.S. Pat. No. 9,987,224, issued Jun. 5, 2018), which claims priority of U.S. Provisional Patent Application Serial Nos. 62/387,405, filed on Dec. 24, 2015.

This application is a continuation-in-part application of U.S. patent application Ser. No. 15/270,034, filed Sep. 20, 2016 (now U.S. Pat. No. 9,750,802, issued Sep. 5, 2017), which is a continuation-in-part application of U.S. patent application Ser. No. 14/954,074, filed on Nov. 30, 2015 (now issued U.S. Pat. No. 9,457,077, issuing on Oct. 4, 2016).

This application is a continuation-in-part application of U.S. patent application Ser. No. 16/037,053, filed Jul. 17, 2018.

The entire disclosure of the prior applications are considered to be part of the disclosure of the accompanying application and are hereby incorporated by reference.

FIELD OF THE INVENTION

A method for treating an individual suffering from a chronic infectious disease and who has cancer employs a CRISPR system to selectively kill or reduce the numbers of pathogenic bacteria within the individual and the individual is then administered an immune checkpoint inhibitor. In particular embodiments, the pathogenic bacteria are one of *E. coli, Pseudomonas aeruginosa* and *Klebsiella* bacteria, and the checkpoint inhibitor is selected from the group consisting of nivolumab, pembrolizumab, pidilizumab, AMP-224, AMP-514, STI-A1110, TSR-042, RG-7446, BMS-936559, MEDI-4736, MSB-0020718C, AUR-012 and STI-A1010. Further embodiments include enhancing the growth of a second bacteria in the individual, such bacteria including *Akkermansia, Bacteroides, Bifidobacterium, Clostridium, Enterococcus, Fusobacterium, Lactobacillus, Propionibacterium, Ruminococcus, Veillonella, Prevotella, Escherichia* and *Streptococcus*. Still other embodiments include increasing the levels of *Roseburia* and/or *Faecalibacterium prausnitzii*, in the individual's gut microbiome.

BACKGROUND OF THE INVENTION

There are over 200 different known cancers that afflict human beings. Cancer causes millions of deaths a year worldwide and rates are also rising as more people live to an older age and urbanization causes more stress. It is anticipated that one in eight people currently alive will eventually die of cancer. Cancer manifests itself in a wide variety of forms, characterized by different degrees of invasiveness and aggressiveness. Malignant tumors are the second leading cause of death in the United States, after heart disease.

The majority of tumors harbor p53 mutants. As the "guardian of the genome," p53 is arguably one of the most important tumor suppressors that controls the regulation and expression of many genes that mediate cell cycle arrest, DNA repair and apoptosis. Under physiological conditions, newly synthesized p53 quickly undergoes ubiquitination and degradation. The p53 tumor suppressor protein plays critical roles in preventing malignant transformation by inducing cell growth arrest or apoptosis. Normally, p53 is inactive in the cell and its levels are low. In response to cellular stress such as DNA damage, p53 levels increase dramatically and it becomes activated through multiple post-translation modifications.

Cancer causes millions of deaths a year worldwide and rates are also rising as more people live to an older age. It is anticipated that one in eight people currently alive will eventually die of cancer. Cancer manifests itself in a wide variety of forms, characterized by different degrees of invasiveness and aggressiveness. Malignant tumors are the second leading cause of death in the United States, after heart disease. 87% of cancer diagnoses in the U.S. are in people age 50 and older. The global population is rapidly aging. Currently, 566 million people are aged 65 years old worldwide, with estimates of nearly 1.5 billion by 2050, particularly in developing countries. Infections constitute a third of mortality in people over 65 years old. Moreover, lengthening life spans correlate with increased time in hospitals or long-term care facilities and exposure to drug-resistant pathogens. The risk of nosocomial infections increases with age, independent of duration spent in healthcare facilities. One theory is that as a person ages, their immune system changes and is less robust in addressing bacterial infections. By enhancing the microbiome of a person as they age, it is believed that infections that would otherwise be encountered will be avoided, or at least the frequency and severity of the same will be decreased. Aging is a pathophysiological phenomenon that is possible to influence so as to delay or postpone the aging process, and in turn, delay the onset and incidence of various cancers. The prospect of achieving a longer life, free of age related functional decline and fragility, such as cancer, is perhaps the quintessential long-felt but unsolved problem of mankind. Increasingly, there is a growing awareness of the importance of the variation in the gut microbiota as its affects the etiology of several age-related diseases, including cancer.

In the US, bladder cancer is the fourth most common type of cancer in men and the ninth most common cancer in women. Non-muscle invasive bladder cancer (NMIBC) begins and stays in the cells lining the bladder without growing into the deeper main muscle layer of the bladder, and accounts for the majority (70-80%) of patients diagnosed with bladder cancer. Bladder cancer has the highest recurrence rate of any malignancy. Although NMIBC is a relatively benign disease, it recurs in 50-70% of patients, of which 10-20% eventually progress to high-grade muscle-invasive disease. More than 1 million patients in the US and Europe are estimated to be affected by the disease.

Non-alcoholic fatty liver disease is a condition ranging from benign lipid accumulation in the liver (steatosis) to steatosis combined with inflammation. The latter is referred to as non-alcoholic steatohepatitis (NASH). NASH is viewed as the hepatic component of metabolic syndrome. Estimates from the USA are that 5.7% to 17% of all adults have NASH, while 17% to 33% of Americans have NAFLD. As obesity and insulin resistance reach epidemic proportions in industrialized countries, the prevalence of both NAFLD and NASH is increasing and is therefore considered to be a major health hazard. Steatosis alone is considered a relatively benign condition for the liver itself and is also a reversible condition. However, the transition towards NASH represents a key step in the pathogenesis, as it sets the stage for further damage to the liver, such as fibrosis, cirrhosis and liver cancer. While the mechanisms leading to steatosis are well described, little is known about the actual risk factors that drive hepatic inflammation during the progression to NASH. Consequently, therapeutic options are poor.

Cachexia is a positive risk factor for death, meaning that if a patient has cachexia, the chance of death from the underlying condition is increased dramatically. Skeletal muscle atrophy is a nearly universal consequence of cancer. Cachexia is considered the immediate cause of death of a large proportion of cancer patients, ranging from 22% to 40% of cancer patients. The pathogenesis of cancer cachexia is poorly understood. Only limited treatment options exist for patients with clinical cancer cachexia. Current treatment strategies involve attempting to improve an individual's appetite using appetite stimulants and protein supplementation to provide the individual with required nutrients. The reversal of cancer cachexia and muscle wasting leads to prolonged survival, and with the ability to retain muscle mass and strength, it is believed that various forms of cancer treatment may be more effective, if only due to the fact that the cancer victim may be able to withstand the rigors of the various cancer treatments involved. Cachexia was overlooked for many years, with doctors directing their attention to the primary illness instead. Many, however, now view cachexia as a distinct, treatable condition.

Probiotics are so-called "good" microorganisms (typically bacteria) that are ingested (or contacted with a person) alive by an individual so that the introduced microorganisms can colonize the GI tract of the person. Conventional prebiotics are ingestible ingredients that selectively support the growth or survival of the "good" microorganisms which are desirably present in the GI tract. Conventional prebiotics are typically a nutrient source (e.g., fructooligosaccharide or galactooligosaccharide) that can be assimilated by one or more members of the GI microbiome, but which are not digestible by the human host.

The development of molecular techniques to identify and quantify microbial organisms has revolutionized the microbial world. Genomic characterization of bacterial diversity relies on sequence analysis of the 16S ribosomal RNA gene, which is present in all bacteria and archaea. The 16S rRNA gene contains species-specific hypervariable regions, which allow taxonomic classification, and highly conserved regions, which act as a molecular clock and a binding site for PCR primers. Using current technologies, an organism does not need to be cultured to determine its type by 16S rRNA sequencing.

The human gut is perhaps one of the most complex networks in the body and is colonized by trillions of microorganisms including bacteria, archaea, fungi, protists, and viruses, among which bacteria are the major inhabitants. Hepatocellular carcinoma (HCC) is one of the most common malignancies in the world. Gut microbiota has been demonstrated to play a critical role in liver inflammation, chronic fibrosis, liver cirrhosis, and HCC development through the gut-liver axis. Gut microbial dysbiosis accompanies the progression of alcoholic liver disease, non-alcoholic fatty liver disease and liver cirrhosis, and promotes HCC progression. Microbial dysbiosis contributes to cancer susceptibility via multiple pathways. Further studies have suggested that the microbiota and their associated metabolites are not only closely related to carcinogenesis by inducing inflammation and immune dysregulation, which lead to genetic instability, but also interfere with the pharmacodynamics of anticancer agents. Chronic inflammation has been verified as a driving cause of cancer. Inflammation promotes tumor progression and accelerates the invasion and metastasis. The generation of inflammation-associated factors can also inactivate tumor-suppressor genes (e.g., P53 mutation). The hepatic environment is greatly influenced by the pathogens or metabolites produced by the microbiota in the GI tract through the hepatic portal venous system. Liver exerts an essential effect on the host microbial community by filtering the blood stream as well as metabolizing and neutralizing toxins derived from intestinal microbes. Gut microbial dysbiosis contributes to hepatocarcinogenesis because the microbiota and microbial metabolites are detected by liver resident immune cells and are able to modify hepatic metabolism. NAFLD is considered to be a major risk factor for HCC.

The use of checkpoint inhibitors has revolutionized various cancer treatments. Improving the outcomes of such treatments by an understanding of how a person's microbiome can be beneficially manipulated to advance positive outcomes that employ checkpoint inhibitors is a long sought but unsolved issue.

SUMMARY OF THE INVENTION

One aspect of the present invention is directed to a method for treating an individual suffering from one of bladder cancer and colorectal cancer that involves the use of a clustered regularly interspaced short palindromic repeats (CRISPR) CRISPR associated protein (Cas) system or a CRISPR from *Prevotella* and *Francisella* 1 (Cpf1) to accomplish the selective killing or reduction in the number of a pathogenic bacteria within the individual, followed by the administration of an immune checkpoint inhibitor.

The microbiota inhabiting our bodies influence cancer predisposition and etiology. The largest microbial community in the human body resides in the gut and comprises somewhere between 300 and 1000 different microbial species. The human oral microbiome and the bacteria inhabiting such microbiome are, in certain circumstances, also effective as agents in the treatment of cancer. Various embodiments of the present invention involve the modification of at least two, if not three separate microbiomes of a person to treat certain conditions. For example, the treatment for cachexia may be achieved via modification of an individual's oral microbiome via the delivery of particular bacteria designed to produce therapeutic amounts of tomatidine. The simultaneous provision of bacteria to the individual's gut microbiome that are designed to produce therapeutic amounts of p53 protein can also be achieved, with the two separate microbiomes being employed to address separate but related issues involved in cancer treatments. This particular aspect of the present invention, while simple in nature, is believed to have profound effects in avoiding undesired drug interactions that can complicate treatment regimens. By having different microbiomes of the same individual administer different desired compounds, drugs, factors, proteins, etc. to the person's body, the ability to separately control administration and amounts (as well as to address issues by killing bacteria in one but not the other microbiome) is rendered feasible as a way to administer desired cancer fighting agents to an individual.

In particular embodiments, the pathogenic bacteria is selected from the group consisting of *E. coli, Pseudomonas aeruginosa* and *Klebsiella* bacteria and the immune checkpoint inhibitor selected from the group consisting of nivolumab, pembrolizumab, pidilizumab, AMP-224, AMP-514, STI-A1110, TSR-042, RG-7446, BMS-936559, MEDI-4736, MSB-0020718C, AUR-012 and STI-A1010. In other embodiments, one enhances the growth of a second bacteria in the individual selected from the group consisting of *Akkermansia, Bacteroides, Bifidobacterium, Clostridium, Enterococcus, Fusobacterium, Lactobacillus, Propionibacterium, Ruminococcus, Veillonella, Prevotella, Escherichia* and *Streptococcus* bacteria.

Certain aspects of the present invention are directed to modifying a person's intestinal (gut), oral or skin microbiota using specific combinations of pre-biotics, pro-biotics and/or anti-biotics to establish a defined microbiota that can treat and/or reduce the likelihood that individuals will experience various diseases, including cancer. The employment of various bacteria, whether in particular combinations or after being modified using CRISPR-type systems, forms various embodiments of the present invention, and leads to improved outcomes when checkpoint inhibitors are used to treat various forms of cancer.

For example, various embodiments of the present invention are directed to averting or reducing the likelihood of cancer by employing bacteria modified to address p53 deficiency. In such a manner, rather than treating human cells and the consequent issues surrounding genetic manipulation of human cells for treatments of cancer, the present invention provides a method and system that employs the microbiome of a person, whether than be oral, gut or skin, or a combination thereof, to treat cancer by increasing the level of p53 to take advantage of the role of such protein in the progression of various cancers. Provision of modified bacteria as described herein to pre-treat a person prior to a cancer treatment, such as radiation, can also be used to lessen the otherwise detrimental effects of the radiation treatment. Moreover, after such treatments, provision of such modified bacteria to restore the person's microbiomes, whether they be oral, skin or intestinal, is one aspect of the present invention. Use of modified skin bacteria to treat melanoma is one aspect of the present invention, thus providing a way to treat skin cancer by providing essential compounds to reduce the spread and health of cancer cells while at the same time, enhancing the growth and propagation of beneficial bacteria, especially those modified as described herein via a CRISPR system.

Through coevolution of bacteria, archaea and fungi with the human host over thousands of years, a complex host-microbiome relationship emerged in which many functions, including metabolism and immune responses, became codependent. This coupling becomes evident when disruption in the microbiome composition, termed dysbiosis, is mirrored by the development of pathologies in the host. Among the most serious consequences of dysbiosis, is the development of cancer. Various embodiments of the present invention are directed to the field of Oncology, and in particular, embodiments directed to a method of ameliorating, treating, or preventing a malignancy in a human subject wherein the steps of the method assist or boost the immune system in eradicating cancerous cells. In certain embodiments, administration of beneficial bacteria to an individual's microbiome that have been modified so as to produce effective amounts of desired compositions, compounds, agents, e.g. tomatidine, p53 protein, etc., is employed to address cancerous conditions. In several embodiments, the administration of such beneficial bacteria and microbes to an individual's microbiome invokes either an active (or a passive) immune response to destroy, weaken or render less invasive certain cancerous cells, and preferably maintains muscle tissue to combat cancer cachexia. Various embodiments of the present invention involve the expression/production by microbes of an individual's microbiome of a phytochemical to enhance the lifespan and health of a human.

Preferably, the modified bacteria employed in the present invention are administered orally to a patient in order to deliver the therapeutic directly to the site of inflammation in the gut. Suppositories can also be employed for administration of particular bacteria that may be more difficult to deliver to a particular portion of a person's body, e.g. those that may be destroyed while passing through a person's stomach. The advantage of an oral or rectal approach is that it avoids systemic administration of immunosuppressive drugs and delivers the therapeutic directly to the gastrointestinal tract. In certain embodiments, the viability and stability of such modified bacteria is enhanced to support the production of such microbes of desired agents/compounds, e.g. tomatidine, p53 protein, rapamycin, resveratrol, methylene blue, etc. and by doing so, a method is provided that reduces gut inflammation, enhances gut barrier function, and/or treats autoimmune disorders. Preferably, such modified bacteria are capable of producing therapeutic anti-inflammation and/or gut barrier enhancer molecules, particularly in the presence of reactive nitrogen species, and more preferably the bacteria are functionally silent until they reach an environment containing local RNS, wherein expression of the therapeutic molecule is induced. In certain embodiments, the genetically engineered bacteria are non-pathogenic and may be introduced into the gut in order to reduce gut inflammation and/or enhance gut barrier function. For example, in some embodiments, the bacteria are under the control of a RNS-responsive regulatory region and a corresponding RNS-sensing transcription factor such that a desired product, e.g. butyrate is produced, which induces the differentiation of regulatory T cells in the gut and/or promotes the barrier function of colonic epithelial cells. Short-chain fatty acid production by commensal bacteria is important in regulating the immune system in the gut. Butyrate plays a direct role in inducing the differentiation of regulatory T cells and suppressing immune responses associated with inflammation. Butyrate is normally produced by microbial fermentation of dietary fiber and plays a central role in maintaining colonic epithelial cell homeostasis and barrier function. Use of such modified bacteria, especially those modified via CRISPR-Cas systems, provides a way to generate a desired therapeutic effect in a manner that lowers the safety issues associated with systemic exposure. Resveratrol (3,4',5-trihydroxystilbene; $C_{14}H_{12}O_3$) is a polyphenolic phytoalexin found in grapes, berries, peanuts, and wines. Resveratrol has been viewed as an antioxidant, anti-inflammatory, anti-apoptotic, and anticancer agent. Moreover, it has been reported that resveratrol modulates mitochondrial function, redox biology, and dynamics in both in vitro and in vivo experimental models. Resveratrol also attenuates mitochondrial impairment induced by certain stressors. Resveratrol upregulates, for example, mitochondria-located antioxidant enzymes, decreasing the production of reactive species by these organelles. Resveratrol also triggers mitochondrial biogenesis, ameliorating the mitochondria-related bioenergetics status in mammalian cells. Brain cells (both neuronal and glial) are susceptible to mitochondrial dysfunction due to their high demand for adenosine triphosphate (ATP). Additionally, brain cells consume oxygen ($O_2$) at very high rates, leading to a proportionally high mitochondrial production of reactive species. One aspect of various embodiments of the present invention is the maintenance of mitochondrial function in various cell types to address degenerative diseases, which involve mitochondrial impairment and increased generation of reactive species, leading, for example, to neuroinflammation and cell death. The mechanism by which resveratrol protects mitochondrial function and dynamics is not completely understood, but it is known that resveratrol is able to induce cytotoxicity depending on its dosage. Resveratrol produced by the microbiome of an individual can be employed to improve the dysregulation of the gut microbiota induced by a high-fat diet, as it will result in increasing the ratio of *Bacteroides*-to-Firmicutes and also increases the growth of *Lactobacillus acidophilus* and *Bifidobacterium* in humans. It is believed that resveratrol modifies the intracellular environment by changing the oxidizing milieu into a reducing milieu and upregulates intracellular glutathione, potentiating a signal transduction cascade that results in mitophagy, and thus paves the way to an anti-aging environment. Rapamycin was first discovered in Easter Island soil bacteria in the 1980s. It is known that rapamycin extends the life span of mice. The protein that rapamycin targets is a kinase called mTOR. This kinase plays a role in a variety of pathways. mTOR suppresses some senescent cells from secreting their cocktail of problematic molecules and mTOR plays a role in the positive effects of caloric restriction. But given the disparity of microbiome constituents between any two individuals, the present inventors contend that the manner by which to effectively address aging of any particular individual lies in taking advantage of the noted differences of each individual's microbiome to address the aging mechanisms involved.

One aspect to the present invention relates to the fact that microbiome composition can influence chemotherapy efficacy. Various bacterial strains have been found to enhance resistance against pathogenic infections and to improve the therapeutic efficacy of immune checkpoint inhibitors. The effects of the intestinal microbial metabolite butyrate interferes with the development of colorectal cancer. Increased levels of SOFA, namely, acetate, butyrate, and propionate in CRC are usually linked with lower risk and improved prevention or therapy. Microbial-derived butyrate counteracts tumor development. Butyrate suppresses proinflammatory genes and tumor growth, the latter via histone deacetylase inhibition, which downregulates oncogenic signaling pathways. However, depending on local concentration, SCFAs can also play a dual role in cancer. Butyrate, for instance, also inhibits proliferation of healthy intestinal progenitor cells. Certain strains are associated with cancer. *Porphyromonas gingivalis* has been found to be involved in several different types of cancer. A significant overabundance of *P. gingivalis* was found in fecal samples from CRC patients. Similarly, *Fusobacterium, Peptostreptococcus, Prevotella, Parvimonas, Bacteroides*, and *Gemella* are among the most prominent CRC-associated bacteria. Moreover, certain metabolites are known to enhance cancer. Exogenous formate may fuel cancer invasion as increased formate overflow is a hallmark of oxidative cancer. One aspect of the present invention is therefore directed to shifting the metabolic state of the tumor microenvironment into a lesser oncometabolite-containing state.

Certain embodiments involve the administration of beneficial bacteria to an individual's microbiome that have been modified so as to produce effective amounts of desired compositions, compounds, agents, etc., e.g. tomatidine, p53 protein, rapamycin, resveratrol, methylene blue, butyrate, SCFA's, etc. For example, in several embodiments, the administration of beneficial bacteria and microbes to an individual's microbiome invokes either an active (or a passive) immune response to destroy, weaken or render less invasive certain cancerous cells. Various other embodiments are drawn to the co-administration of one or more of tomatidine, p53 protein, rapamycin, resveratrol, methylene blue etc., in combination with conventional therapies for treating diseases, such as cancer. In particular, the co-administration of various pre-biotic compositions to enhance and sustain the desired effects of the beneficial modified bacteria forms another aspect of the present invention. In this regard, incorporation by reference of U.S. Patent publication No. 20160213702 to Maltzahn et al. is included as part of the written description of various aspects of the present invention. For example, in view of the fact that the microbiota of humans is complex and varies by individual depending on genetics, age, sex, stress, nutrition and diet, modifying the numbers and species of gut, oral, vaginal and skin microbiota can alter community function and interaction with the host. A number of probiotic bacteria known in the art, as well as some foods considered to be 'prebiotic' that contain substances that promote the growth of certain bacteria and that stimulate beneficial microbiota shifts to improve human health, can be employed in concert with the modified bacteria as described herein to effect desired cancer treatment regimens. For example, the administration of glycans in an amount effective to modulate the abundance of the bacterial taxa can be used to achieve better outcomes in the treatment of various age related diseases, including cancer.

One aspect of the present invention relates to the use of various *Lactobacillus* species to reduce LDL, cholesterol, and triglycerides to cause an improvement and amelioration of inflammation and steatosis—which can lead to cancer.

Nonalcoholic fatty liver disease (NAFLD) is a risk factor for colorectal cancer. NAFLD is associated with a high incidence of CRC. Age is an important factor for CRC and the CRC incidence increases with age. The present inventors believe that particular modulation of the gut microbiome, including the establishment and maintenance of certain beneficial bacteria, including *Lactobacillus, Bifidobacterium*, and certain *Streptococcus* species, forms the basis of a treatment of NAFLD, as well as NASH, and in particular, the use of particular species that have been modified via a CRISPR system. Nonalcoholic steatohepatitis (NASH) is a more advanced form of NAFLD where liver injury has occurred, and can lead to liver failure, portal hypertension, hepatocarcinoma and cirrhosis. Even without significant changes in BMI, glucose, or LDL2, probiotic use is believed to significantly decrease ALT, AST, total cholesterol, HDL, and TNF-.alpha.1.

Thus, in various embodiments of the present invention, the employment of particular probiotics as described herein, provides a treatment for NAFLD that shows improvements in intestinal dysbiosis, leading to decreasing intestinal permeability, endotoxemia and subsequent inflammation.

The most frequent cause which leads to obesity is a dysbalance between energy intake and energy expenditure. The gut microbiota contributes to host metabolism. Gut microbiota not only influence absorption and disposal of nutrients to the liver, but also can lead to the development of "metabolic endotoxemia" and activation of TLR ligands, which can stimulate liver cells to produce proinflammatory cytokines, thereby initiating inflammation and fibrogenesis, which characterize NASH. Another possible molecular mechanism implicated in NAFLD development is the alteration in LPS-endocannabinoid (eCB) system regulatory loops and bile acid metabolism. Thus, certain embodiments of the present invention are directed to the modification of intestinal bacterial flora by specific probiotics to achieve a therapeutic approach for the treatment of NAFLD.

One strategy for NAFLD treatment encompassed by the present invention relates to a treatment for obesity that involves manipulation of an individual's gut microbiota. Thus, modulation of gut microbiota by probiotic treatment or dietary intervention provides beneficial effects with respect to body weight, influence on glucose and fat metabolism, insulin sensitivity and reduction in chronic systemic inflammation, all of which can impact the status of NAFLD. Probiotic positive effects on host metabolism are specifically directed to beneficial levels of *Lactobacillus* and/or *Bifidobacterium* strains. For example, employment of *Saccharomyces cerevisiae* var. *boulardii, Enterobacter halii* or *Akkermansia muciniphila* are used to achieve beneficial effects for obesity and NAFLD. In certain embodiments, because obstructive sleep apnea and attendant fatigue are common in patients with NAFLD, one aspect of the present invention relates to the use of "no-snore strips" as described herein (and in more extensive pending patent applications incorporated herein by this reference, e.g. U.S. Pat. No. 9,445,936) such that use of such strips can beneficially modify not only the populations of oral bacteria, but also snoring patterns, thus providing those suffering from NAFLD with a way to manage such condition to permit them to address fatigue issues and to thus sleep better, exercise more, etc.

Gut bacteria alter the way individuals store fat, how levels of glucose are balanced in the blood, and how humans respond to hormones that make individuals feel hungry or full. Certain population mixes of microbes set the stage for NAFLD, obesity and diabetes. The gut community in lean people is diverse while obese people have a gut microbe community that is comparatively less diverse. Lean individuals, for example, tended to have a wider variety of Bacteroidetes, a population of varied microbes that specialize in breaking down bulky plant starches and fibers into shorter molecules that the body can use as a source of energy.

Probiotics have physiologic functions that contribute to the health of gut microbiota, can affect food intake and appetite, body weight and composition and metabolic functions through gastrointestinal pathways and the modulation of the gut bacterial community. Thus, in various embodiments of the present invention, probiotics are employed, e.g. (*Enterococcus faecium, Streptococcus thermophilus L. acidophilus, Bifidobacterium longum, L. plantarum* and/or *B. lactis*) to significantly reduce total serum cholesterol and LDL cholesterol and to improve the LDL:HDL cholesterol ratio. In particular embodiments, a CRISPR-Cas system (Clustered Regularly Interspaced Short Palindromic Repeats-CRISPR-associated) is employed to alter one or more of these bacteria to modify various virulence factors associated with bacteria so that beneficial populations of bacteria inhabit an individual's oral and/or gut microbiome.

Various embodiments of the present invention relate to a composition capable of increasing the level of anti-oxidized low-density-lipoprotein (oxLDL) antibodies in vivo for use in the treatment or prevention of NASH. OxLDL is an immunogenic molecule that stimulates the induction of anti-oxLDL antibodies. Phosphorylcholine, a component of *Streptococcus pneumoniae*, is a major antigen in oxLDL, which is recognized by anti-oxLDL antibodies that have protective properties. One embodiment relates to the expression of OxLDL in bacteria via employment of a CRISPR-Cas system to insert genes for OxLDL such that such modified bacteria produce OxLDL to therefore stimulate the induction of anti-oxLDL antibodies, thus providing the protective effects of such antibodies. Using the present invention, fibrosis can be decreased or prevented by the production and administration of anti-oxLDL antibodies to avoid inflammation of the liver and to therefore treat NASH and NAFLD. While antibodies against oxLDL are known in the art, various embodiments of the present invention relate to a new medical use of such antibodies, as well as to methods and systems that modify gut bacteria to enhance the production of such antibodies. In other words, various embodiments of the invention relate to a composition comprising antibodies against oxLDL for use in the treatment or prevention of hepatic inflammation or more in particular the treatment or prevention of NASH, and/or the use of oxLDL antibodies for the preparation of a medicament for the treatment or prevention of hepatic inflammation and in the treatment of NASH. In certain embodiments, a method of treatment or prevention of hepatic inflammation is provided where oxLDL antibody levels are increased by modification of particular bacteria using a Clustered Regularly Interspaced Short Palindromic Repeats-CRISPR-associated system (CRISPR-Cas) or Clustered Regularly Interspaced Short Palindromic Repeats from *Prevotella* and *Francisella* 1 (CRISPR/Cpf1) system so that the bacteria is able to produce desired levels of oxLDL antibodies.

In other embodiments, the methods and systems disclosed herein are directed to modifying the gut microbiota of an individual to ameliorate the progression of NAFLD, including reducing liver aminotransferases, total-cholesterol, TNF-.alpha. and improving insulin resistance in individuals with NAFLD. In certain embodiments, NAFLD is thus treated by modulation of the gut microbiota. Effective treatments include employing a method of populating a subject's gastrointestinal tract with a diverse and useful selection of microbiota in order to alter a dysbiosis. Various aspects and embodiments of the invention are directed to methods and compositions for modulation of NAFLD of an individual's gut microbiome by using bacteria that have been treated with a CRISPR-Cas or CRISPR-Cpf1 system to reverse antibiotic resistance or to render ineffective certain virulence factors in pathogenic bacterial cell, as well as modifying gut bacteria in a manner to make them "better" in various ways, including an ability to outcompete other undesired bacteria. Other various embodiments of the present invention relate to the employment of engineered autonomously distributed circuits containing programmable nucleases (e.g. "programmable nuclease circuits") that are delivered to microbial organisms in vivo to modulate the expression of certain antibiotic resistant and virulence factors of particular microbial organisms. Some embodiments employ the Type II CRISPR-Cas (Clustered Regularly Interspaced Short Palindromic Repeats-CRISPR-associated) system of *Streptococcus pyogenes* to reverse antibiotic resistance in a wide range of microbial organisms. In certain embodiments, the CRISPR-Cas system is used to weaken resistance of microbial pathogens to existing antibiotics. The use of the CRISPR-Cas system may be viewed as a paradigm shift in combating pathogens because it enables autonomous and distributed neutralization of disease at the gene level. Various aspects of the present disclosure provide methods that comprise modifying bacterial cells to target a gene or nucleotide sequence of interest, and in particular, genes involved in the storage of fat. Such modified bacterial cells include an engineered autonomously distributed circuit having at least one nucleic acid encoding a programmable nuclease that targets a gene or nucleotide sequence directed to fat metabolism.

While there are medications approved for treating diseases and conditions associated with NAFLD, there are currently no medications specifically approved for the treatment of NAFLD itself. Treatment protocols have instead been focused upon the associated conditions, such as the metabolic syndrome. Conventional treatment of NAFLD includes weight loss, restricting dietary fat, administration of medications employed in the treatment of an associated condition and administration of medications employed in the treatment of hyperlipidemia. Many medications employed to treat conditions associated with NAFLD are hepatotoxic.

Various embodiments of the present invention are directed to a method for treating NAFLD in a subject in need thereof that includes administering a composition including a therapeutically effective amount of *Prevotella*, and more preferably *Prevotella* that has been modified, e.g. by CRISPR-Cas, in a manner that reduces the effect of at least one of the virulence factors of such bacteria. Other embodiments involve the employment of bacteria of the *Bacteroides* family that have been modified to reduce the amount of a ligand-activated transcription factor.

Dysbiosis in a person's gut has a significant role in the pathogenesis of human NAFLD/NASH. In various embodiments of the present invention, administration of probiotics, as well as associated fiber diets to support such bacteria, is involved, in some embodiments employing *Bifidobacterium* and *Lactobacillus* strains. Control of the bacterial flora lowers proinflammatory cytokine production (tumor necrosis factor-.alpha., interleukin-6, interferon-.gamma.) via down-regulation of the nuclear factor kappa B, and decreases oxidative stress. Probiotics can reduce the urease activity of bacterial microflora, decrease fecal pH value and reduces amino-acid fermentation and ammonia adsorption; reduce aminotransferases, and improve the lipid status in NAFLD patients. Each of these may be modified via CRISPR-Cas systems employed to alternative characteristics of an individual's microbiome.

Microbiome research in liver disease has evolved recently as an exciting new field. Prebiotics encompass products that promote the growth of beneficial intestinal microbiota. Probiotics include live microbial strains in predefined quantities. Both prebiotics and the use of probiotics is involved in the various embodiments of the invention as herein described. The present invention is directed in various embodiments directed to ways to modify the microbiota to treat hepatic steatosis, liver inflammation, fibrosis, and developing and advanced liver disease. The purposeful manipulation of the gut microbiota is done to address various liver diseases at both early and late disease stages.

More than 90% of the adult microbiome is composed of species belonging to four bacterial phyla: Firmicutes, Bacteroidetes, Actinobacteria, and Proteobacteria. Differences exist, however, with respect to different individuals as well as in different habitats. For example, Firmicutes are the major species in the intestine, vagina, skin, and oral cavity, while Actinobacteria and Proteobacteria are more dominant in the oral cavity, skin, and nasal cavity. The enterotype is a classification of the microbiome, with the gut microbiome being classified into three enterotypes. Each enterotype includes a dominant species selected from the group consisting of: *Bacteroides, Prevotella*, and Ruminococcus, with enterotypes being unrelated to race, residential region, or diet.

It is believed that commensal microbiota protect against biliary injury and liver fibrosis. The present inventor believes that there is a significant association of fatty liver with *H. pylori* infection. Thus, various embodiments involve the modification of an individual's microbiome, including *H. pylori* in one's stomach, to combat NAFLD and NASH and cancers related thereto. Thus, use of CRISPR-Cas to render *H. pylori* more susceptible to particular antibiotics is one way in which such modification may be achieved.

NAFLD is a complex disease and a treatment targeting one pathological process often also causes changes in other pathways. Prebiotics represent a specific type of dietary fiber that when fermented, mediate measurable changes within the gut microbiota composition, usually causing an increase in the relative abundance of bacteria thought of as beneficial, such as bifidobacteria or certain butyrate producers. Prebiotics are usually non-digestible carbohydrates, oligosaccharides or short polysaccharides, including inulin, oligofructose, galactofructose, galacto-oligosaccharides and xylooligosaccharides, all leading to increasing the relative abundance of bifidobacteria and lactobacilli. The gut of individuals with various maladies, including obesity, harbor bacteria in their gut that establishes an inflammation-associated microbiome, often providing a lower potential for butyrate production and reduced bacterial diversity. Thus, one objective of the present invention is to alter the microbiome of such individuals to increase bacterial diversity in their gut and to increase levels of butyrate production. Patients with NAFLD have small intestinal bacterial overgrowth and increased intestinal permeability. Thus, altering the microbiome of such individuals is achieved to counter the progression of NAFLD. In certain embodiments, one objective is to increase the proportion of Ruminococcaceae in a person's microbiome and to also reduce the proportion of *Escherichia*, e.g. by modifying *Escherichia* via CRISPR-Cas to make it less viable than it otherwise would be.

Probiotics can reduce liver aminotransferases, total cholesterol, tumor necrosis factor .alpha. and improve insulin resistance in patients with NAFLD. Similarly, treatment of other diseases in the gut, like inflammatory bowel disease (IBD) is implicated with respect to modification of the gut microbiome. The concept of an altered gut microbiota or dysbiosis is possibly the most significant development in IBD and NAFLD research in the past decade. A definitive change of the normal gut microbiota with a breakdown of host-microbial mutualism is believed to be the defining event in IBD and NAFLD development.

In other embodiments, one objective is to increase the levels of *Lactobacillus, Leuconostoc, Lactococcus, Pediococcus* and Firmicutes in an individual's gut microbiome, while reducing the levels of Bacteroidetes and *Akkermansia* spp. In certain other embodiments, one objective is to increase the levels of *Prevotella* and *Roseburia* (a butyrate-producer) in a person's gut microbiome, and especially the colon microbiome. Other embodiments focus on increasing the levels of *Bacteroides* in the person's gut and decreasing the levels of *Escherichia*, Lachnospiraceae and *Megasphaera*.

Periodontal disease is a chronic infectious disease of the tissues surrounding the teeth that result in tooth loss. Several reports have indicated that periodontal infection is related to NAFLD. Both NAFLD and periodontal disease are chronic inflammatory conditions that are known as 'silent diseases'. Therefore, both conditions need to be detected early and treated under collaborative medical and dental care in order to prevent progression to NASH. The prevalence of NAFLD in the American general adult population is 10%-40% and that of NASH is approximately 2%-5%. One aspect of the present invention is directed to the relationship between periodontal pathogens, e.g. composed of *P. gingivalis*, and the severity of NAFLD. The eradication of periodontal pathogens, such as *P. gingivalis* infection, is believed to have a beneficial effect upon NASH.

Certain embodiments of the present invention are directed to a method for treating non-alcoholic fatty liver disease by providing to an individual in need thereof an effective amount of a composition comprising modified *L. reuteri* bacteria, preferably using CRISPR-Cas and/or Cpf1 systems, to provide such bacteria in a manner so that they have the ability to survive the conditions in the duodenum or jejunum of the small intestine. Other embodiments involve a method for treating non-alcoholic fatty liver disease involving establishing in the gut of an individual a population of beneficial bacteria selected from the group consisting of *Lactobacillus, Bifidobacterium*, and *Streptococcus* species and administering at least 6 grams per day of fiber to the individual to maintain the beneficial bacteria in the gut of the individual. Still other embodiments are directed to a method for treating non-alcoholic fatty liver disease by increasing oxLDL antibody levels in an individual by modifying bacteria, preferably using a CRISPR-Cas or Cpf1 system, so that the bacteria is able to produce desired levels of oxLDL. Yet other methods involve the modulation of NAFLD of an individual's gut microbiome by using beneficial bacteria, e.g. such as one or more of bacteria from one or more of the phylas: Firmicutes, Bacteroidetes, Actinobacteria, and Proteobacteria, preferably treated with a CRISPR-Cas or CRISPR-Cpf1 system to reverse antibiotic resistance or to render ineffective certain virulence factors in pathogenic bacterial cells. In other embodiments, an individual is administered a therapeutically effective amount of *Prevotella*, and more preferably *Prevotella* that has been modified in a manner that reduces the effect of at least one of the virulence factors of such bacteria. Certain embodiments are directed to a method for treating non-alcoholic fatty liver disease involving the modifying of bacteria of the *Bacteroides* family so that they produce reduced amounts of a ligand-activated transcription factor as compared to non-modified bacteria. In preferred embodiments, probiotics are further provided to feed such bacteria, with the result being improvements in levels of density lipoprotein, and tumor necrosis factor-.alpha.

Other aspects of the present invention are directed to treating and/or reducing the likelihood of colorectal cancer. Humans possess an inflammatory response—the triggering of the overproduction of hydrochloric acid—as the stomach's primary response to bacterial colonization. Inflammation of the stomach lining coincides with production of peptides called cytokines, which stimulate production of a hormone called gastrin. Gastrin triggers parietal cells in the stomach lining to produce more hydrochloric acid, which kills off most invading microbes. Notably, *H. pylori* is the only bacterial organism in the stomach that cannot be killed by hydrochloric acid. If you inhibit gastric acid production, you interfere with the stomach's natural defense mechanism. An abnormally low level of acidity in the stomach is a factor in various disease states. Since reduced gastric acidity does appear to make the mammalian stomach more vulnerable to bacterial invasion and gastritis, however, physicians are advised to re-evaluate the long-term use of proton-pump-inhibiting drugs in their patients.

One aspect of the several embodiments of the present invention is directed to the modification of microbes in a manner that reduces, if not eliminates, the symptoms of GERD. *Helicobacter pylori* is one of several pathogens that persist within the host despite a robust immune response. *H. pylori* elicits a proinflammatory response from host epithelia, resulting in the recruitment of immune cells which manifests as gastritis. Certain embodiments employ CRISPR-Cas or Cpf1 systems to render *H. pylori* more susceptible to certain drugs, including antibiotics, thus addressing the resistance otherwise experienced by treating *H. pylori* with antibiotics.

While not bound by theory, it is believed that *H. pylori* survives antimicrobials, including calprotectin (CP), which employs nutrient sequestration, through alteration of its outer membrane. Thus, one embodiment of the present invention relates to the interference with and modification of the normal mechanism of *H. pylori* resistance to antibiotics by affecting the ability of *H. pylori* to form biofilms, including the retention and maintenance of lipid A production, which is normally interfered with by *H. pylori* when contacted by CP. In particular embodiments, CRISPR-Cas systems are employed to undermine the ability of *H. pylori* to form biofilms. One such strategy is to add additional genetic components in *H. pylori* cultures that include lipid A expression and the purposeful inclusion of such a culture of *H. pylori* in a person's stomach so as to establish a competitively beneficial culture of such modified *H. pylori* in the stomach. Thus, once such bacteria are the predominant bacteria, as compared to non-modified *H. pylori*, then the application of CP (or other suitable antibiotics) can be used to eliminate or vastly reduce the number of *H. pylori* bacteria in the person's stomach. Having the individual provided with further *H. pylori* cultures that possess such modified characteristics is further contemplated as a way in which to preclude the reestablishment of a wild type *H. pylori* culture from persisting in the person's stomach. By such a strategy, the person is able to substantially eradicate *H. pylori* species that are resistant to antibiotics. Other ways to decrease the formation of *H. pylori* biofilms include increasing cell surface hydrophobicity. Another way is to enhance the function of the Lpx lipid A biosynthetic enzymes (e.g. LpxF, LpxL, and LpxR enzymes) to ensure that their functions are not perturbed. Thus, to combat *H. pylori* resistance to cationic antimicrobial peptides, one target is to affect the formation of biofilms and to reduce the ability of *H. pylori* to modify endotoxins. This can be achieved in various ways, but preferably by employment of CRISPR-Cas systems to interfere with genes involved in the formation of biofilms by *H. pylori.*

Certain embodiments are directed to the modification of resident *H. pylori* populations in vivo in a person's stomach so as to beneficially disrupt the colonization of the gastric glands by *H. pylori*. Other aspects involve the modification of dietary components and essential micronutrients in concert with the gastrointestinal microbiota to affect a beneficial modification of *H. pylori* activity so as to maintain it as a commensal bacteria and to prevent its activity as a pathogen, thus precluding its carcinogenic potential.

One aspect of the present invention is directed to therapeutic interventions in the microbiome directed against molecular entities, such as essential and antibiotic resistance genes to quorum sensing systems components used to control microbial networking behaviors, including the chemical communication and production of virulence factors. Various embodiments are focused on dietary interventions and microbial modification genetic tools to modify and/or eliminate pathogenic microorganisms and to control dysbiosis. Various embodiments of the present invention are also directed towards the modification of the human-microbiota ecosystem to promote health and to combat disease, including the modification and/or elimination of certain bacteria living in the human body. The determination of human microbiota and the analyses of the presence or absence of specific microbial species in accordance with particular diseases provides one of skill in the art with the ability to identify particular biomarkers and to target the same to treat GERD.

While phage therapy could potentially have beneficial impact on human microbiomes, host specificity greatly limits the types of bacteria that can be employed and the selection of a specific phage to use as a therapeutic agent requires in-depth knowledge of the pathogen causing a given disease. In the absence of such knowledge, some have suggested the use of a cocktail of different species of phages to broaden the range of action, but such a cocktail could have undesired negative effects on the microbial community. Thus, in preferred embodiments of the present invention, CRISPR systems are employed to effect desired microbial modifications. The relative simplicity of the mechanism of action and the peculiarities of Cas9 make the CRISPR/Cas9 system an ideal tool for a vast assortment of procedures, particularly for genomic editing, and in various embodiments of the present invention, the editing of bacterial strains is employed to interfere with the development of GERD and to otherwise treat GERD.

In various embodiments of the present invention, various targets for intervention using CRISPR-Cas systems include the modification of bacteria resident in the human gut that are distinct from humans in various respects. For example, most bacteria synthesize thiamine de novo, whereas humans depend on dietary uptake. Methionine is not synthesized de novo in humans and must be supplied by diet. In contrast, most bacteria need to synthesize methionine to survive. There are a myriad of other orthologous gene groups conserved in both human and human commensal gut microflora that are not suitable targets for drug development. The majority of unique targets found in microbes' genomes are genes responsible for the metabolism of carbohydrates, amino acids, xenobiotics, methanogenesis, and the biosynthesis of vitamins and isoprenoids, and in particular for the purposes of various embodiments of the present invention, focus is directed to those genes that are non-homologous to those encompassed in human genome. A number of microbial genes and products, including bacteriocins, lysins, holins, restriction/modification endonuclease systems, and other virulence factors contribute to resistance to antibiotics. Thus, an alternative to killing or inhibiting growth of pathogenic bacteria is targeting these key regulatory systems. Other aspects of the present invention are directed to targeted changes in microbiota by the rational use of prebiotics and probiotics to abolish metabolic alterations associated with various maladies, including GERD, obesity, cancer, etc.

In particular embodiments, compounds such as halogenated furanones produced by many microbial species, mostly belonging to the proteobacteria, are employed to interfere with AHL and AI-2 QS pathways in Gram-negative and Gram-positive bacteria. It is believed that by interrupting normal systems of bacterial inter and intra quorum sensing, one may effectively modify bacterial cell-cell communication in a manner that prevents colonization by pathogenic bacteria, and in particular, can be employed to interfere with biofilm formation by *H. pylori* and thus, treat GERD.

High doses and frequent use of antibiotics can disrupt and destabilize the normal bowel microbiota, predisposing patients to develop *Clostridium difficile* infections. Up to 35% of these patients develop a chronic recurrent pattern of disease. Fecal bacteriotherapy is the transplantation of liquid suspension of stool from a donor (usually a family member) and has been used successfully in severe cases of recurrent *C. difficile* relapse. Many problems exist with this therapy since it can increase the risks of transmitting other pathogens. One particular focus of the present invention is to employ transplanted microbiota to treat metabolic disorders in humans but that limit the risks involved in conventional fecal transplants. For example, via the use of modified bacteria (e.g. using CRISPR-Cas systems) one is able to more effectively employ antibiotics to target particular regions of the body, to target particular bacteria, etc. in a manner that avoids the complications experienced in the typical use of antibiotics, which cause complications from *C. difficile* growth.

In particular embodiments, probiotic microorganisms that possess resistance to low gastric pH and have the capacity to reach the intestines alive, are used to exert beneficial effects on the human body, preferably lactic acid-producing bacteria of the *Lactobacillus* and *Bifidobacterium* genera. Such microorganisms are preferably those modified using CRISPR-Cas to provide a population that can be more easily controlled and manipulated to maintain particular levels in an individual's microbiome. Specifically, some embodiments of the present invention include regulating the balance of intestinal microbiota by physically blocking the adhesion of pathogenic species onto epithelial cells, such blocking action directly mediated by means of increases in the production of a mucosal barrier by goblet epithelial cells and/or by regulating epithelial permeability by enhancing the formation of tight-junctions between cells. Use of CRISPR-Cas to modify or delete virulence factors of particular bacteria, such as adhesion abilities thereof, is employed in this fashion.

In various embodiments of the present invention, CRISPR/Cas9 is used to selectively deplete a given bacterial community of a particular harmful strain or species, or of particular virulence factors possessed by particular strains of bacteria. Thus, in certain embodiments, the identification of a harmful pathogen is performed, and CRISPR/Cas9 is then used to selectively deplete or modify that particular bacterial species from an individual's gut microbiota. The use of antibiotics is believed to increase the ability of bacteria to acquire drug resistance-encoding plasmids. Thus, the CRISPR/Cas9 system may be used to introduce specific mutations into essential, antibiotic resistance and virulence genes, as well as to directly modulate the expression of particular genes. For example, one can employ a Cas protein that lacks nuclease activity but retains a binding capacity so as to repress bacterial transcription by binding to promoter regions to effect the blocking of transcriptional initiation and/or elongation. CRISPR-Cas or Cpf1 systems may also be used to fuse regulatory domains in order to switch on/off the expression of specific genes. Thus, the present invention includes the engineering of commensal bacteria with improved properties using a CRISPR/Cas system to prevent and treat diseases. One of skill in the art will appreciate the steps required to affect the desired levels of target specificity and delivering efficiency.

Still other embodiments employ the modification of various beneficial bacteria so that they express certain compounds and substances, notably those substances found to be effective as an anti-*H. pylori* agent, such as those isolated from garlic and *ginseng*. Alliin, the main active molecule present in Garlic extract, is used to effect immune modulation. The use of dialkyl-thiosulfinate and/or propy thiosulfonate can be employed to improve disease resistance of a pathogen, with these compounds generated from the natural degradation of propiin, a molecule present in most *Allium* species, and more specifically onion, shallots or chives. Still other sulfur compounds may be employed to inhibit *H. pylori* colonization. Using CRISPR-Cas, one is able to modify resident bacteria to express the active ingredient in garlic found to be an effective killer of *H pylori*. Such expressed compounds include those described above.

Similarly, another aspect of the present invention is to control *H. pylori* populations in an individual's stomach by a diet including kimchi. Other aspects are directed to the expression of kimchi genes by one or more bacterial species that reside in a human stomach. In a manner similar to the expression of certain genes derived from garlic, one is therefore able to control the population of *H. pylori* in a person's stomach. The use of CRISPR-Cas to insert genes into particular bacteria so as to facilitate the control of *H. pylori* is one aspect of certain embodiments, including the insertion of genes having the active agent contained in Korean kimchi and garlic. The incidence of gastric cancer is about 20 per 100,000 population (in Korea) and about 50 per 100,000 population (in Japan, where far less kimchi is eaten), demonstrating that kimchi is effective as a cancer preventative agent. Similarly, the expression of garlic related genes by one or more bacterial species that reside in a human stomach is another embodiment of the present invention. The use of garlic (as well as kimchi) to address GERD is considered to be a teaching away from the prior art, as many have identified garlic and onions as causing heartburn. Garlic (*allium sativum*), like onions, shallots and leeks, among others, belongs to the alliaceae family, and all contain organosulfur products. Garlic in particular contains allicin, an organosulfur compound that is produced when garlic is broken or crushed, through the action of the allinase enzyme on alliin. Allicin is a potent phytocide, with marked antibiotic and antifungal properties. The release of allicin produces other sulfur derivatives, such as ajoene, allyl sulfides, diallyl sulfides, allyl methyl disulfide, allyl methyl trisulfide, s-allyl cysteine and diallyl trisulfide. Allicin pronouncedly inhibits the secretion of various cytokines (IL-1b, IL-8, IP-10 and MIG) from epithelial cells, suppressing the expression of interleukin 8 (1-8) and interleukin 1b (IL-1b) mRN and is therefore considered to be effective in attenuating intestinal inflammation. It is believed that low doses of garlic oil suppress NOS (inducible Notric Oxide Synthase) activity, ulceration and apoptosis of the intestinal mucosa. At high doses, however, garlic oil has shown a toxic effect, which is why it is deduced that garlic is beneficial in moderate doses, but can be toxic in high doses. Garlic extracts and garlic oil have also been found to be powerfully anti-microbial against other GI bacteria such as *Escherichia coli*, *Shigella* sp, *Salmonella* sp, and *Proteus mirabills*.

One aspect of the present invention is directed to the use of probiotics to modulate the human microbiota and promote health and prevent antibiotic side effects. L. species are acid-resistant and commensal and their concentrations in the normal human stomach vary between 0 and $10.^3$ mL.$^{-1}$. They can survive in the stomach for periods of up to 2 h. In various embodiments, fructo-oligosaccharides (FOS) and trans-galacto-oligosaccharides (TOS), such as inulin, are used to selectively stimulate growth and activity of health-promoting bacteria. In this regard, dietary inulin fibers are used to stimulate $Mg.^{2+}$ and $Ca.^{2+}$ absorption and are a potent stimulant of mineral absorption, especially achieved by oligofructose-enriched inulin. Certain strains of gut bacteria have a preference for inulin fibers. Thus, one aspect of the present invention is to selectively advance the population of such bacteria in a person's gut. It is known that N-butryic acid increases $Ca.^{2+}$ and $Mg.^{2+}$ absorption. Thus, certain embodiments of the present invention are directed to the provision of bacteria designed to produce n-butryic acid to treat PPI-induced $Ca.^{2+}$ disturbances. It is believed that dietary inulin stimulates intestinal $Mg.^{2+}$ absorption, and thus, other embodiments of the present method include the provision of dietary inulin in addition to the provision of the various bacteria strains as described herein. One aspect of the present invention is therefore directed to the impact of PPIs on $Ca.^{2+}$ homeostasis and provides a treatment for PPI-induced mineral disturbances. Dietary oligofructose enriched inulin fibers are believed to prevent omeprazole-induced reduction of $Ca.^{2+}$ absorption and lead to improved intestinal $Mg.^{2+}$ absorption, thus preventing PPI-induced mineral deficits in individuals.

In various embodiments, the present invention is directed to the use of dietary inulin to counteract reduced intestinal $Ca^{2+}$ absorption upon PPI treatment. One aspect of the present invention is directed to the local luminal acidification of the colon to enhance intestinal $Mg^{2+}$ absorption and by so doing, preventing PPIH. Other embodiments are directed to the use of the fructan fiber inulin to reduce intestinal pH, such ingested inulin fibers being fermented in the large intestine by bifidogenic gut bacteria, resulting in short-chain fatty acids (SCFA), which in turn acidify the colon. Thus, one aspect of various embodiments is directed to the stimulating action of SOFA on intestinal $Mg^{2+}$ absorption by reducing the luminal pH. Certain aspects are directed to the enhancement of intestinal $Mg^{2+}$ and $Ca^{2+}$ absorption in order to counteract omeprazole-induced defects in mineral uptake. Proton-pump inhibitor-induced hypomagnesemia (PPIH) is the most recognized side effect of proton-pump inhibitors (PPIs). Additionally, PPIH is associated with hypocalcemia and hypokalemia. It is hypothesized that PPIs reduce epithelial proton secretion and thereby increase the pH in the colon, which may explain the reduced absorption of and $Mg^{2+}$ and $Ca^{2+}$. Fermentation of dietary oligofructose-enriched inulin fibers by the microflora leads to acidification of the intestinal lumen and by this enhances mineral uptake. One aspect of the present invention is therefore directed to the improvement of mineral absorption by application of dietary inulin to counteract PPIH.

In various embodiments of the present invention, candidate probiotic strains are isolated from fecal samples, especially after enrichment with a prebiotic application. As described in other applications incorporated herein, the use of particular fecal samples from healthy Amish individuals is employed to combat GERD. Moreover, one strategy for enhancing the establishment of probiotic bacteria in the human intestinal tract is via the parallel administration of a prebiotic. In vivo selection (IVS) may be employed to isolate candidate probiotic strains from fecal samples following enrichment with a prebiotic. For example, isolated bifidobacteria from human subjects who consumed increasing doses of galactooligosaccharides (GOS) revealed an 8-fold enrichment in *Bifidobacterium adolescentis* strain IVS-1. It is believed that such selected strains are able to outcompete resident *Bifidobacterium* populations. One aspect of the present invention, especially employing one or more of the modified bacteria as described herein, is to substantially enhance the establishment and competitiveness of one or more putative probiotic strains in an individual's gastrointestinal tract to combat GERD.

One aspect of the present invention is directed to the provision of pharmaceuticals based on an individual's own microbiome. Thus, in certain embodiments, isolation of particular bacteria from an individual's stool is employed and CRISPR-Cas and/or Cpf1 systems are then used to modify such bacteria in various beneficial ways, as described herein. The reintroduction of such modified bacteria into the person's gut (e.g. via fecal transplantation) provides a way to selectively and competitively compete with other undesired bacteria in the person's gut. Preferably, the resident populations of gut microbes are reduced substantially before the reintroduction of the modified bacteria, thus providing a better chance and opportunity for the establishment of a population of preferred bacteria, as modified via the CRISPR-Cas systems, as described herein.

The growth of microbiota communities is under control of distinct subfamilies of host genes encoding antimicrobial peptides (AMPs). When bacteria colonize a given human habitat, the expression of AMPs, including .alpha. and .beta. defensins and cathelicidins, is upregulated in order to limit the spreading of bacteria. The equilibrium between the immune system and immunoregulatory functions of bacteria appears to be a delicate balance in which the loss of a specific species can lead to an overreaction or suppression of the innate immune system. The maintenance of a stable, fermentative gut microbiota requires diets rich in whole plant foods particularly high in dietary fibers and polyphenols. Individuals colonized by bacteria of the genera *Faecalibacterium, Bifidobacterium, Lactobacillus, Coprococcus*, and *Methanobrevibacter* have significantly less of a tendency to develop obesity-related diseases like type-2-diabetes and ischemic cardiovascular disorders. These species are characterized by high production of lactate, propionate and butyrate as well as higher hydrogen production rates, which are known to inhibit biofilm formation and activity of pathogens. Thus, in various embodiments of the present invention, these bacterial species are selected and administered to an individual in preferred ratios that reflect those of healthy individuals so as to attain the general balance of bacterial populations in a person's gut. Moreover, preferably bacteria are selected that are effective in inhibiting biofilm formation and in particular, those that demonstrate a high production of lactate, propionate, butyrate and hydrogen. CRISPR-Cas and/or Cpf1 may be employed to provide such characteristics to the selected bacterial species in this regard.

CDT (*Clostridium difficile* transferase) is a binary, actin ADP-ribosylating toxin frequently associated with hypervirulent strains of the human enteric pathogen *C. difficile*, the most serious cause of antibiotic-associated diarrhea and pseudomembranous colitis. CDT leads to the collapse of the actin cytoskeleton and, eventually, to cell death. The lipolysis-stimulated lipoprotein receptor (LSR) is the host cell receptor for CDT. By applying the CRISPR-Cas technology to interfere with the binding component of CDT, preferably by impacting amino acids 757 to 866 of CDT, one is able to interfere with the binding of CDT to the LSR. Thus, interfering with the interaction between CDT and its receptor LSR, is one way to provide an anti-toxin strategy for preventing cell entry of the toxin. Use of the active expression of CRISPR arrays in *C. difficile* strains is therefore one way in which to counter *Clostridium difficile* nosocomial infections associated with antibiotic therapies. One aspect of certain embodiments is directed to modifying the site where the bacterium *Clostridium difficile*'s binary toxin binds to intestinal cells' LSR (lipolysis-stimulated lipoprotein receptor) protein and triggers a mechanism that results in the invasion of the host cells by the bacteria. *Clostridium difficile* produces the binary, actin ADP-ribosylating toxin CDT (*Clostridium difficile* transferase). While CDT can lead to death of the host cells through collapse of the actin cytoskeleton, low doses of CDT result in the formation of microtubule-based protrusions on the cell surface that increase the adherence and colonization of *C. difficile*. Thus, one aspect of certain embodiments relates to the interference with the adherence characteristics of this bacteria by reducing the amount of CDT produced by bacterial cells, thus providing a population of *C. difficile* that do not pose the problems of wild type strains. One aspect of certain embodiments involves blocking certain areas in the toxin and the receptor in order to prevent the *Clostridium difficile* transferase toxin from entering the host cell.

Other embodiments are directed to a system and method for reducing the likelihood of GERD and includes the modification of an individual's gut microbes in a manner that reduces, if not eliminates, the symptoms of GERD. Certain embodiments employ CRISPR-Cas or Cpf1 systems to render H. *Pylori* more susceptible to certain drugs, including antibiotics, thus addressing the antibiotic resistance otherwise experienced by treating H. *Pylori* with antibiotics.

Still other aspects of the present invention are directed to treating aging in a fashion such that individuals do not suffer from the various forms of cancer that invariably increase as an individual ages. Extending healthy life by slowing ageing is the most efficient way to combat fatal and disabling pathologies, such as cancer, that plague the elderly human population. Thus, one aspect of the present invention is directed not to overcoming age-associated pathologies one-by-one, but rather, to prevent or delay age-related pathologies in general, thus more effectively addressing the commonplace chronic disorders experienced by the elderly. The present invention therefore represents a paradigm shift in the current public health strategy, which is targeted to the prevention of particular disorders, which even if successful, leaves an individual susceptible to other comorbidities that inevitably substitute for the pathology being treated. In various embodiments of the present invention, a method and system is provided that treats age-related disease by increasing the healthspan of a human individual. In various embodiments, rapamycin (sirolimus) is administered to an individual via a person's microbiome by employing microbes, and in particular bacteria modified to produce rapamycin and preferably other anti-aging agents, to achieve this objective.

As described in more detail herein, one aspect of the present invention involves the use of a natural small molecule derived from tomato plants, tomatidine, which is believed to cause cell growth, especially in skeletal muscle tissue. Tomatidine is an inhibitor of muscle atrophy and thus has a use as a therapeutic agent for skeletal muscle atrophy. Tomatidine is a steroidal alkaloid and the aglycone of alpha-tomatine, an abundant glycoalkaloid in tomato plants that mediates plant defense against fungi, bacteria, viruses and predatory insects. When consumed by animals, alpha-tomatine is hydrolyzed by stomach acid and intestinal bacteria to tomatidine, which is absorbed by the gut. Tomatidine is believed to have an anti-atrophic (anabolic) effect in skeletal muscle and possesses anti-hyperlipidemic and anti-atherosclerotic effects without evidence of toxicity. Tomatidine is significantly more potent than ursolic acid in building muscle tissue and has a different mechanism of action.

The tomato belongs to the Solanaceae family that includes more than 3,000 species. Tomato fruit consumption has been associated with a reduced risk of inflammatory processes, cancer, and chronic noncommunicable diseases (CNCD) including cardiovascular diseases (CVD) such as coronary heart disease, hypertension, diabetes, and obesity. Tomatidine is found in certain plants at certain developmental stages, such as in green (but not ripened red) tomatoes. One aspect of the present invention is directed to the provision to individuals in need thereof with bacteria that have been modified to produce effective amounts of tomatidine to address the muscle atrophy associated with various cancers. In one embodiment, DNA encoding tomatidine or its analogs is inserted into the genome of one or more bacterial species by employing CRISPR-Cas or CPf1 systems, such that an individual can orally take a pill containing such modified bacteria (preferably bacteria of the same species as presently reside in the individual's gut microbiome) and in such a manner, administer tomatidine to the individual in a manner that does not require injections or the taking of traditional pharmaceutical formulations containing tomatidine. In such a manner, the production by such bacteria inside the individual provides a more natural way for tomatidine to be provided to those in need of its extraordinary abilities to foster the retention of muscle mass in the individual. The ability to further modify the populations of bacteria inside an individual via the use of particular antibiotics, for example, those that can target the modified species that produce tomatidine, provides a way to control the amount of tomatidine in the individual's body. Tomatidine in this instance, is but one of many examples of how the personal microbiome of an individual can be amended, modified, enhanced and/or changed to adjust the levels and amounts of various compounds, drugs, molecules, etc. that are important in maintaining or restoring health to an individual.

Yet another aspect of the present invention involves the treatment of cancer cachexia, specifically including methods that use a natural small molecule derived from tomato plants, tomatidine, which is believed to cause cell growth, especially in skeletal muscle tissue. Tomatidine is an inhibitor of muscle atrophy and thus has a use as a therapeutic agent for skeletal muscle atrophy. Tomatidine is a steroidal alkaloid and the aglycone of alpha-tomatine, an abundant glycoalkaloid in tomato plants that mediates plant defense against fungi, bacteria, viruses and predatory insects. When consumed by animals, alpha-tomatine is hydrolyzed by stomach acid and intestinal bacteria to tomatidine, which is absorbed by the gut. Tomatidine is believed to have an anti-atrophic (anabolic) effect in skeletal muscle and possesses anti-hyperlipidemic and anti-atherosclerotic effects without evidence of toxicity. Tomatidine is significantly more potent than ursolic acid in building muscle tissue and has a different mechanism of action.

One aspect of the present invention is directed to the provision to individuals in need thereof of bacteria that have been modified to produce effective amounts of tomatidine to address the muscle atrophy associated with various cancers and diseases. In one embodiment, DNA encoding tomatidine or its analogs is inserted into the genome of one or more bacterial species by employing CRISPR-Cas or Cf11 systems, such that an individual can orally take a pill containing such modified bacteria (preferably bacteria of the same species as presently reside in the individual's gut microbiome) and in such a manner, administer tomatidine to the individual in a manner that does not require injections or the taking of traditional pharmaceutical formulations containing tomatidine. In such a manner, the production by such bacteria inside the individual provides a more natural way for tomatidine to be provided to those in need of its extraordinary abilities to foster the retention of muscle mass in the individual. The ability to further modify the populations of bacteria inside an individual via the use of particular antibiotics, for example, those that can target the modified species that produce tomatidine, provides a way to control the amount of tomatidine in the individual's body. Tomatidine in this instance, is but one of many examples of how the personal microbiome of an individual can be amended, modified, enhanced and/or changed to adjust the levels and amounts of various compounds, drugs, molecules, etc. that are important in maintaining or restoring health to an individual.

In certain embodiments of the present invention, a method for treating cancer cachexia involves the administering to the microbiome of a subject in need thereof of an effective amount of a bacterial combination that expresses p53 protein and tomatidine, such cancer being for example, one of breast cancer, bladder cancer, kidney cancer, or colorectal cancer. In certain embodiments, the cancer is a metastatic cancer; and the microbiome is one or more of the gut microbiome, the oral microbiome or the skin microbiome. Other embodiments involve mucosally administering to the subject an effective amount of a bacteria that has been modified to express one of tomatidine, statins and/or p53, with the bacteria selected from the group consisting of *Streptococcus, Actinomyces, Veillonella, Fusobacterium, Porphromonas, Prevotella, Treponema, Neisseria, Haemophilus, Eubacteria, Lactobacterium, Capnocytophaga, Eikenella, Leptotrichia, Peptostreptococcus, Bacillus* Calmette Guerin, *Staphylococcus*, and *Propionibacterium*. Still other embodiments include the provision of *Streptomyces hygroscopicus* in an amount effective to produce therapeutically effective amounts of rapamycin to the subject. It should be appreciated that a therapeutically effective amount is preferably an amount sufficient to elicit any of the listed effects of natural tomatidine and p53, for example, including, but not limited to, the power to treat cancer cachexia in a fashion demonstrated by a result indicating that there is evidence of the maintenance of muscle mass in the individual treated. In certain preferred embodiments, the mucosal administration is oral administration and the subject individual maintains or increases muscle mass. In most preferred embodiments, the bacterial composition has been modified via a CRISPR-Cas or Cfl1 system to express tomatidine, and in other embodiments, produces both tomatidine and p53 protein. Other embodiments include a bacterial composition that includes one of a *Chlamydia* species, *Shigella flexneri, Mycoplasma* bacteria, and/or *H. pylori*.

The TP53 gene, which encodes the p53 protein, is the most frequent target for mutation in tumors. In response to a number of stressors, p53 becomes activated to promote cell cycle arrest, apoptosis or senescence thereby suppressing tumor growth and also plays many additional roles including regulating cellular metabolism. Unlike most tumor suppressor genes, which are predominantly inactivated as a result of deletion or truncation, the majority of mutations in TP53 are missense mutations. In contrast to wild-type p53, which under unstressed conditions is a very short-lived protein, missense mutations lead to the production of full-length p53 protein with a prolonged half-life. While many tumor-derived mutant forms of p53 can exert a dominant-negative effect on the remaining wild-type allele, serving to abrogate the ability of wild-type p53 to inhibit cellular transformation, the end result is that the wild-type version of p53 is lost and the mutant form is retained, with cancer and cachexia resulting. There is substantial evidence that certain mutants of p53 can exert oncogenic, or gain-of-function, activity independent of their effects on wild-type p53. There is a great need for methods of treating cancer having mutated p53 protein and TP53. Certain embodiments of the present invention address such need by providing methods and systems whereby the oncogenic mutant p53 populations are hindered via the provision of agents that block their activities, such as statins, while also providing a new source of wild-type p53 produced by added bacteria to the individual. Enhancing an individual's microbiome with microbes that are also able to produce tomatidine and rapamycin is a further way to combat various disease conditions and to restore health to the individual.

Over 50 percent of human tumors contain mutations in the gene encoding p53, a protein that plays a significant role in early carcinogenesis. Wild-type p53 is a tumor suppressor, but mutant p53 has been shown to exhibit gain-of-function properties as well, causing cancer formation by enabling normally suppressed pathways. One such oncogenic pathway activated by this mutation is the sterol biosynthesis pathway. 3-Hydroxy-3-methylgutaryl CoA reductase inhibitors (statins) have proven therapeutic and demonstrate preventative effects in cardiovascular diseases. Inhibition of this pathway using HMG-CoA Reductase inhibitors, commonly known as statins, forms various aspects of the present invention and provides an entirely new treatment against mutant p53 expressing cancers, especially with respect to the delivery of statins being via microbes administered to individuals. Statins are among the most carefully studied class of drugs in use and are well tolerated with an excellent safety profile. Statins are already FDA approved and widely used for other indications. Statins also have other beneficial anti-inflammatory and immune-modulatory effects.

Various aspects of the present invention involve the confluence of some historically important developments in the biological sciences, including the recognition of the importance of the microbiome, the advent of CRISPR-Cas systems to manipulate various genes and organisms, and the ability to better control the "holy grail" of cancer therapy, namely the use of competently folded p53 protein and the reduction of the actions of mutant p53 on the progression of cancer. With the further acknowledgement of tomatidine as one of the natural plant-derived agents that can have a positive effect on cachexia, especially that associated with cancer, as well as the beneficial effects from the administration of rapamycin via an individual's microbiome, there is presently a new and extraordinary opportunity to advance the long sought but heretofore unfulfilled prospects of effectively treating cancer so as to substantially extend the quality and quantity of life for those suffering therefrom.

Still further aspects of the present invention are directed to the appreciation that cancer and aging appear to be related in many ways, as the ability of cancer to be immortal is a characteristic that if understood, could be applied to the aging of cells, thus providing an ability to combat age related diseases. By understanding how p53 can be administered to cancer tissues to halt cancer progression, while at the same time, stopping the ability of mutated p53 to promote cancer growth, a large step in providing a treatment for cancer is achieved. The further provision of modified microbes administered to an individual's microbiome so as to produce effective amounts of particular agents, such as tomatidine (to forestall muscle atrophy), rapamycin (to address aging issues), etc., is a further benefit that may be achieved, especially given the CRISPR-Cas technologies that easily provide an unprecedented ability to modify microbes in this regard—and without having to genetically engineer human cells in the process of such treatments.

Still other embodiments of the present invention are directed to the employment of anaerobic bacteria to address cancer growth as the biological environment of cancerous tumors and anaerobic bacteria are similar in several respects. Abnormal blood vessels and hypoxic and necrotic regions are universal features of solid tumors. These hypoxic and anoxicmicroenvironments may be targeted by obligatory or facultative anaerobic bacteria, such as *Bifidobacterium, Salmonella, Escherichia*, lostridium and *Listeria*, as well as certain bacteria believed to be involved in the progression of Alzheimer's Disease, namely, spirochetes. Some of these bacteria accumulate and actively proliferate within tumors, resulting in much higher increases in the number of bacterial cells in tumor tissues relative to those in normal organ cells and tissues, such as liver and spleen. The use of attenuated bacterial strains to suppress tumor growth forms one aspect of the present invention, and in particular, use of BCG that has been further modified to express particular agents, such as tomatidine, p53, statins, rapamycin, etc. whether in separate bacterial cells or the same bacterial cell, comprises various aspects of the present invention. Such modified bacteria may act by directly suppressing tumor growth directly and/or by activating host immunity, but are effective in achieving improved therapeutic effects. One advantage of various embodiments of the present invention is that instead of having to inject bacteria into a patient's tumor, the administration of agents is achieved preferably via the more organic administration of agents via the bacterial and host cell interactions. Various of the embodiments encompassed herein rely upon approaches that stimulate inflammation, and thus trigger an antitumor immune response by the individual.

Other aspects of certain embodiments of the present invention are directed towards the administration of quercetin, a polyphenol abundant in plants, preferably as it is or in the form of a glycoside. Quercetin may be found in various plants including citrus fruits, onion, buckwheat, and *Sophora* and it is known that it has a wide variety of physiological functions, such as platelet aggregation/adhesion inhibition activities, and vasodilatory activity. In various embodiments of the present invention, quercetin is expressed by cells of an individual's microbiome to elicit anticancer activity and to confer other health benefits. The administration of certain modified bacteria to an individual in various embodiments effectively creates microbial cell factories that, through metabolic engineering of heterologous biosynthetic pathways, turns microbes into a cost effective and more organic way to both produce and administer agents to desired tissues in a person suffering from cancer and other diseases. Using CRISPR-Cas techniques especially, and in view of the guidance provided herein, one of ordinary skill in the art will be able to excise desired genes from plants, bacteria and fungi and have them expressed by microbes that can be administered to an individual's microbiome such that health can be restored to the individual.

In addition, treatments for various types of cancer are desired that relate to the production of competently folded p53 tumor support factor. There has been a long felt but unmet need for a way to inexpensively administer desired amounts of p53 protein to an individual in need thereof. The present invention in several of its aspects addresses this concern, for example, by the expression of p53 by human microbiome bacteria, by the administration of BCG cells transformed to express p53 (as well as statins, rapamycin, tomatidine, quercetin, neoalbaconol, a phosphatase and tensin homolog (PTEN), etc.

Thus, in particular embodiments, the present invention is specifically directed to a method of treating cancer cachexia in a subject in need of such treatment by administering a therapeutically effective amount of a composition comprising *Bacillus* calmette-guerin that is adapted to produce tomatidine, wherein the cancer is bladder cancer or alternatively colorectal cancer. The *Bacillus* calmette-guerin is preferably modified via a CRISPR-Cas system to produce tomatidine, is even more preferably adapted to also produce rapamycin, and even more preferably adapted to further produce a statin, such as one or more of Mevacor™, Pravachol™, simvastatin, atorvastatin, fluvastatin, lovastatin, pravastatin and rosuvastatin. In still other embodiments, the *Bacillus* calmette-guerin is adapted to produce neoalbaconol, and even more preferably, it is further adapted to produce p53. Other embodiments are similar to that described above, but the *Bacillus* calmette-guerin is specifically adapted to produce tomatidine and the cancer is colorectal cancer. One will appreciate that similar preferred embodiments include *Bacillus* calmette-guerin being further adapted to produce one or more of rapamycin, a statin, a phosphatase and tensin homolog (PTEN), p53 and/or neoalbaconol.

Treatments for various types of cancer are desired that relate to the production of competently folded p53 tumor support factor. There has been a long felt but unmet need for a way to inexpensively administer desired amounts of p53 protein to an individual in need thereof. The present invention in several of its aspects addresses this concern, for example, by the expression of p53 by human microbiome bacteria. In certain embodiments of the present invention, a method for treating cancer cachexia involves the administering to the microbiome of a subject in need thereof an effective amount of a bacterial combination that expresses p53 protein and tomatidine, such cancer being for example, one of breast cancer, bladder cancer, kidney cancer, or colorectal cancer. In certain embodiments, the cancer is a metastatic cancer; and the microbiome is one or more of the gut microbiome, the oral microbiome or the skin microbiome. Other embodiments involve mucosally administering to the subject an effective amount of a bacteria that has been modified to express one of tomatidine and p53, with the bacteria selected from the group consisting of—*Streptococcus, Actinomyces, Veillonella, Fusobacterium, Porphromonas, Prevotella, Treponema, Neisseria, Haemophilus, Eubacteria, Lactobacterium, Capnocytophaga, Eikenella, Leptotrichia, Peptostreptococcus, Staphylococcus, Streptococcus thermophilus* and *Propionibacterium*. Still other embodiments include the provision of *Streptomyces hygroscopicus* in an amount effective to produce therapeutically effective amounts of rapamycin to the subject. It should be appreciated that a therapeutically effective amount is preferably an amount sufficient to elicit any of the listed effects of natural tomatidine and p53, for example, including, but not limited to, the power to treat cancer cachexia in a fashion demonstrated by result indicating the maintenance of muscle mass in the individual treated. In preferred embodiments, the mucosal administration is oral administration and the subject individual maintains or increases muscle mass. In most preferred embodiments, the bacterial composition has been modified via a CRISPR-Cas or CPf1 system to express tomatidine, and in other embodiments, produces both tomatidine and p53 protein. Other embodiments include a bacterial composition that includes one of a *Chlamydia* species, or *Shigella flexneri, Mycoplasma bacteria*, and *H. pylori*.

With respect to combating aging, particular agents and combinations thereof are employed in various embodiments of the present invention such that the incidence of cancer is lessened due to the avoidance of aging. Certain embodiments involve the administration of microbes to an individual where such microbes have been modified to produce desired levels of such agents/combinations. Since signaling pathways related to the aging of *Caenorhabditis elegans* (*C. elegans*), fruit flies and mice are evolutionarily conserved, compounds and agents extending lifespan in such organisms are believed to be useful in treating age-related diseases in humans. Natural products are preferred as they have a special resource advantage with few side effects. For example, microbes can be introduced to an individual's microbiome so that that they may produce one or more of such desired natural product agents by an individual's microbiome. One such agent is rapamycin (aka sirolimus), which is a macrolide produced by the bacterium *Streptomyces hygroscopicus*. Sirolimus is currently used as an immunosuppressant and is most often used to prevent rejection of transplanted organs. Sirolimus has two approved indications—renal transplantation and lymphangioleiomyomatosis and has also been shown to be potentially effective in treating Tuberous Sclerosis Complex (TSC)-associated seizures, skin disease, brain lesions, pulmonary lesions, and renal lesions. Administration of therapeutically effective amounts of rapamycin via an individual's microbiome (whether oral vaginal, skin, gut, bladder, etc.) forms one aspect of various embodiments of the present invention. Such employment of an anti-aging medicine like rapamycin is believed to be one of the most effective ways to combat various age-associated diseases of aging people. Rapamycin is but one example of the many compounds with anti-aging activity that have been and will be discovered. Delivery of such agents by employing an individual's microbiome is believed to be an effect and person-specific way to account for the vast diversity of individual's biological systems, including the acknowledged disparity and array of microbiome compositions.

Rapamycin is an inhibitor of mTOR complex (mammalian target of rapamycin) which is a serine threonine kinase and a master regulator of protein synthesis, cell growth, and cell metabolism. Excessive mTORC1 activity has been implicated in multiple disease conditions, as well as various cancers, inflammatory bowel disease, inflammatory skin diseases and neurodegenerative diseases. In various embodiments, rapamycin is employed, especially when produced by microbes in an individual's microbiome, to treat or prevent disease conditions by inhibiting the mTORC1 pathway.

In certain embodiments, and while not bound by theory, it is believed that tomatidine increases the ability of an individual to maintain muscle mass, while rapamycin, as an inhibitor of mTOR, which increases the production of muscle proteins, reduces the growth of muscles. It is believed that these two agents may play parallel but separate roles in muscle atrophy, and thus, the use of both of these agents to address cancer, cachexia and aging is one particular aspect of the present invention.

In the treatment of particular cancers, the employment of rapamycin to inhibit cell growth, especially muscle growth, may in various instances be desired. At the same time, retention of muscle mass may be important for an individual to withstand the rigors of various cancer treatments. By administering tomatidine to an individual to maintain desired muscle mass, while also co-administering rapamycin to such individual to inhibit the growth of certain cells, especially cancer cells, one is able to achieve the seemingly converse objectives of maintaining muscle mass so as to preserve the health of an individual, while simultaneously defeating the undesired growth of cancer cells by the administration of effective amount of rapamycin to inhibit such undesired growth.

As described herein, p53 has apoptotic characteristics and effectively keeps cancer growth in check by preventing cells from growing uncontrollably. In a somewhat similar manner, rapamycin also may be employed to regulate growth (e.g. by inhibiting growth of particular cells). Thus, the combination of rapamycin and p53 expression via cells of an individuals microbiome provides two agents that are critical components in cell growth and apoptosis events at the core of cancer treatments. Effective administration of cells (or microbes) of a person's microbiome via the purposeful administration of such cells (which have been modified, preferably via CRISPR-Cas systems) to express therapeutically effective amounts of either or both p53 and rapamycin, is believed to provide an effective treatment for various cancerous conditions.

It is noted that caloric restriction would seem to negatively affect the growth of an organism and detrimentally affect the protein expression that would otherwise ensue in a well-fed individual. Rapamycin is a growth inhibitor, and thus, one would similarly conclude that the employment of such an agent would reduce the expression of proteins, such as those that are employed to build muscle. Moreover, p53 is an agent that generates cell death via apoptosis, and thus, would be viewed as an anti-growth factor in terms of cell survival. And yet all three of these agents are considered instrumental in both the aging process as well as in cancer. As cancer and aging are linked on certain levels, so too are the above referenced agents. The employment of these agents, especially by their purposeful expression via an individual's modified microbiome, provides a unique and effective way in which to combat both cancer and aging. Various embodiments of the present invention are directed to a method for treating, inhibiting, or reducing aging, an age-related symptom, and/or an age-related disease (e.g. cancer) in a subject which comprises administering to the subject a therapeutically effective amount of a compound that has anti-aging characteristics, with administration being preferably via an individual's own microbiome. Included, but not limited to such a list of compounds is rapamycin, p53 and tomatidine.

The administration of such compounds/agents via an individual's microbiome is believed to positively affect the extending of the lifespan of an individual, and especially effective in delaying the onset of age-related diseases and conditions, such as cancer, thus extending the healthspan of the individual from what it otherwise would have been if such administration was not performed. The particular effective amount of such agents/compounds, such as rapamycin (including analog or derivatives thereof) depend upon the disease to be treated, the length of duration desired and the particular characteristics of the individual's microbiome—and which of the one or more various microbiomes of the person may be the source of the administration. In certain embodiments where the agent/compound comprises rapamycin or an analog thereof, administration of rapamycin may be performed to affect about 0.001 mg to 30 mg total per day as an effective dose, preferably at least about 0.1 mg per day, with a preferred blood level of rapamycin in the subject being about 0.5 ng per mL whole blood after administration of the composition after a 24 hour period. By administering antibiotics that target the particular microbes that produce such agents/compounds (e.g. rapamycin) one can address overproduction by such microbes by killing the microbes producing such agents. Various other embodiments are directed to the skin microbiome of a person so as to address diseases of the skin, including but not limited to skin cancer. The lactic acid bacteria *Streptococcus thermophilus* has been found to increase ceramide production in the skin. Ceramides are known to play an essential role in structuring and maintaining the water permeability barrier function of skin. With aging, the total ceramide content of skin, along with the skin's ability to function as a barrier, decreases. Certain embodiments are directed to ceramide supplementation via a subject's microbiome to improve skin barrier function.

Certain embodiments are directed to a method of treating bladder cancer in a subject in need of such treatment, such method comprising administering to a microbiome of a subject with bladder cancer an effective amount of a bacterial composition comprising *Bacillus* calmette-guerin, with the bacterial composition adapted to produce tomatidine and rapamycin. Preferably, the bacterial composition comprises bacteria modified via a clustered regularly interspaced short palindromic repeats (CRISPR) CRISPR associated protein (Cas) system to express one or both of tomatidine and rapamycin. Certain embodiments are focused on treating metastatic bladder cancer. The microbiome employed may be the gut, oral, bladder or skin microbiome. Certain embodiments further include employing a microbe selected from the group consisting of *Streptococcus, Actinomyces, Veillonella, Fusobacterium, Porphromonas, Prevotella, Treponema, Nisseria, Haemophilis, Eubacteria, Lactobacterium, Capnocytophaga, Eikenella, Leptotrichia, Peptostreptococcus, Staphylococcus,* and *Propionibacterium*. One preferred embodiment involves administering a bacterial composition to the subject so that at least 0.1 mg of rapamycin is provided to the subject each day. Preferably, the bacterial composition is modified via a CRISPR-Cas system to express one of rapamycin and/or tomatidine, with preferred bacterial compositions including one of a *Chlamydia, Shigella flexneri, Mycoplasma bacteria,* and *H. pylori*. In other preferred embodiments, the method comprises administering to a microbiome of a subject with bladder cancer an effective amount of a bacterial composition comprising a bacteria that has been modified to express a therapeutically effective amount of tomatidine and rapamycin, with the bacteria selected from the group consisting of *Streptococcus, Actinomyces, Veillonella, Fusobacterium, Porphromonas, Prevotella, Treponema, Nisseria, Haemophilis, Eubacteria, Lactobacterium, Capnocytophaga, Eikenella, Leptotrichia, Peptostreptococcus, Staphylococcus, Propionibacterium, Chlamydia, Shigella flexneri, Mycoplasma bacteria, H. pylori,* and *Streptomyces hygroscopicus*. The bacteria employed may be of a species found in the subject's gut microbiome and may further have been modified using a CRISPR-Cas system to produce one of tomatidine or rapamycin. A therapeutically effective amount of a bacterial composition may also include *Streptomyces hygroscopicus* in an amount effective to provide a therapeutically effective amount of rapamycin to the subject. In particular embodiments, especially directed to addressing bladder cancer, the bacterial composition comprises *Bacillus* calmette-guerin, and even more preferably, where the *Bacillus* calmette-guerin also produces at least one of p53, rapamycin or tomatidine, and especially where the method maintains or increases the muscle mass of the subject. As described in more detail in the detailed description of various embodiments, still other agents, such as methylene blue, metformin, resveratrol (3,4',5-trihydroxystilbene; $C_{14}H_{12}O_3$), p53 protein, spermidine, diallyl trisulfide, apigenin, cyclopamine, sulforaphane, curcumin and glucosamine are employed via the production by microbes of an individual's microbiome to achieve the objective of delaying aging, and thus, in delaying and treating the onset of cancers.

One aspect of the present invention is directed to the use of human specific species of bacteria that are then modified to enhance one or more characteristics deemed beneficial to the skin microbiome and health of the individual, including treating skin cancers. Many embodiments employ bacteria that have been modified via a CRISPR-Cas9 and/or Cpf1 system to either repress the expression of a particular protein or lipid, or to increase the production of beneficial microbial secretions. Clustered Regularly Interspaced Short Palindromic Repeats from *Prevotella* and *Francisella* 1 or CRISPR/Cpf1 is a DNA-editing technology analogous to the CRISPR/Cas9 system. One objective is to avoid modifying an individual's human genome, but instead, to significantly affect the health of humans by employing modifications to the skin microbiome. Use of human specific strains of bacteria, whether they are commensal or pathogenic, including bacteria that are modified to alter their native pathogenicity, is one preferred aspect of many embodiments of the present invention.

Certain aspects of the present invention are directed to a method for altering the microbiome of an individual's skin by administering to a region of the skin of an individual an effective amount of a bacterial formulation. In one preferred embodiment, the individual is a newborn and the step of administering is performed within the first 6 hours of the newborn's birth. Such a bacterial formulation may be a lotion, ointment or gel adapted to be rubbed onto the newborn's skin. The bacteria included in the bacterial formulation may vary to address particular concerns or diseases. For example, the bacterial formulation may include bacteria selected from the group consisting of *Nitrosomonas eutropha* and *Propionibacterium*. More particularly, the equilibrium of a bacterial population of the region of the skin of the individual is modified to increase the number of *Propionibacterium* bacteria and to decrease the number of *Staphylococcus* bacteria on the individual's skin in such region. In other embodiments, the bacterial formulation includes the bacteria *Staphylococcus aureus* that has been modified by employing a CRISPR-Cas or Cpf1 system to interfere with *S. aureus* virulence regulation involving the Agr quorum-sensing signaling molecule. In several embodiments, the bacterial formulation comprises a bacteria that has a tropism specific for the human species. In others, the bacterial formulation comprises at least two of the bacteria selected from the group consisting of: *Prevotella; Lactobacillus johnsonii; Bacteroides fragilis, Lactobacillus ruminus* and *L. infantitis*. In certain embodiments the bacteria is an ammonia oxidizing bacteria. In other embodiments, the region of the skin to which the bacterial formulation is applied is the scalp. In various embodiments, rather than using a wild-type bacteria, the bacteria employed is one that has been modified by CRISPR-Cas or CRISPR-Cpf1 to delete a functional virulence factor from the bacteria. In particular embodiments, the method includes administering to the skin a bacteria that produces tomatidine. In others, the bacteria produces p53. Thus, in some embodiments, the method involves use of bacteria wherein a CRISPR-Cas or CRISPR-Cpf1 system is employed to insert a gene for the production of tomatidine and/or p53 into at least one of the bacteria in the bacterial formulation. In others, a CRISPR-Cas or CRISPR-Cpf1 system is employed to insert one or more genes into the bacteria comprising the bacterial formulation to facilitate the oxidizing of ammonia by the bacteria. To further enhance the ability of desired bacteria to be maintained on the skin of an individual, certain methods further comprise administering to the individual's skin a prebiotic that comprises a nutrient source for the bacteria that is assimilated by the bacteria, and preferably one that is not digestible by the individual. In particular embodiments, the method further includes administering to the skin an extract derived from a helminth selected from the group consisting of *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus,* and *Trichinella spiralis*. In still others, the bacterial formulation includes at least one arabinogalactan. Yet others include at least one of the following: *L. infantitis,* and *L. johnsonii*. In a particular embodiment, the bacterial formulation includes at least one bacteria modified via a CRISPR-Cas system to express a gene encoding interferon regulatory factor 4.

In particular embodiments, in view of the tropism demonstrated by *S. pyogenes* for humans, and the recognition that such bacterial species is found in both the oral and skin microbiome of humans, *S. pyogenes* is a preferred bacterial species to employ in various embodiments of the present invention.

In still other embodiments, the focus is on interspecies interactions within mixed microbial communities, with the objective being to modify competitive relationships involving nonbiocidal biosurfactants, enzymes, and metabolites produced by bacteria and other microorganisms in a manner such that selection of particular bacterial species can be employed to inhibit initial adhesion, trigger matrix degradation, encourage jamming of cell-cell communications, and induce biofilm dispersion. Nonbiocidal molecules are thus employed to modify competitive interactions within biofilms in a manner that promotes the overall health of an individual's microbiome, especially on the skin.

In certain embodiments, a bacterial formulation is applied to newborns within a critical window of time after birth, preferably within the first 24 hours of the newborn's birth, more preferably within 6 hours of their birth, even more preferably within 3 hours of birth, and most preferably within an hour after their birth. The administration can be by several methods, but preferably is a lotion, ointment or gel that is rubbed onto the newborn's skin, preferably all over his/her entire body. A spray or mist can also be applied that contains the bacterial and microbe formulations as set forth herein. While not bound by theory, the critical window to apply to the newborn's skin the referenced formulations, e.g. microbial mixtures of bacteria beneficial in triggering immune system development, is within a relatively short time period and is necessary to establish immune tolerance to a variety of commensal microbes. The way and content of microbes presented at a time in which a newborn has his/her skin colonized establishes immune tolerance to particular commensal microbes. The influx of highly activated T cells into neonatal skin is believed to occur in such critical window. So a mother of a newborn has a choice: to simply rely upon chance as to what particular microbes might be present during this critical window of the newborn's establishing immune tolerance to particular bacteria and other microbes; or to provide the newborn with a selected formulation containing predetermined microbes such that the newborn's developing immune system can properly react to the microbes in the predetermined formulation, and thus provide the newborn with the opportunity to develop a more expansive immune tolerance profile. It is believed that the mechanism that promotes tolerance is tissue specific, and thus, the skin and the gut may have different ways by which they mediate tolerance to commensal microbes. To establish a healthy status of a newborn's skin as it relates to commensal microbes on its skin, the particular type of microbes, including bacteria, brought into contact with his/her skin is achieved in a certain time period after birth (e.g. within 1 to 24 hours after birth) so that the developing immune system of the infant establishes tolerance to such microbes, thus avoiding allergies, autoimmune diseases and other related diseases, as well as chronic inflammation of the skin.

In certain embodiments of the present invention, the skin microbiome is enhanced via providing microbes able to metabolize lipids, proteins and carbohydrates, and thus, produce acid that aids in maintaining the so-called "acid mantel" of the skin. In preferred embodiments the bacteria that is modified has a very narrow host tropism, such that the bacteria are specific for the human species and thus, their modification poses little if any risk to other animals or organisms.

Other embodiments are directed to combating infections of a person's skin by the bacteria *Staphylococcus aureus*. *Staphylococcus aureus* is a commensal and pathogen of both humans and cattle. In certain embodiments the accessory gene regulator (Agr) system and the virulence regulation of *S. aureus* pathogenesis is modified to delete or to at least reduce the virulence of the bacteria. In such a way, the present invention provides a way to effectively combat *S. aureus* infections. In various embodiments of the present invention, CRISPR-Cas9 and/or Cpf1 systems are employed to render ineffective virulence factors of such bacteria involved with the establishment and propagation of infection. Several molecules have been found to interfere with *S. aureus* virulence regulation, especially those targeting the Agr quorum-sensing signaling molecule. By modification of this bacterial species using CRISPR-Cas and/or Cpf1 it is possible to achieve broad-spectrum inhibitory effects on most *S. aureus* strains and Agr subtypes.

The tropism of individual bacteria for particular host tissues (e.g., skin vs. respiratory tract vs. gastrointestinal tract) is determined by the array of available adhesion-receptor pairs. In preferred embodiments, bacteria having substantial, if not entire, human host specificity are employed. For example, *Salmonella enterica* serovar *Typhi*, known to be the bacteria responsible for typhoid fever, a life-threatening human disease, demonstrates strict human host specificity. In certain embodiments, the virulence factors of such bacteria are compromised by being modified via the CRISPR-Cas or Cpf1 system to render the modified bacteria as non-pathogenic. Similarly, the bacteria *Neisseria*, the causative agent of gonorrhea, is a disease restricted to humans, and thus similar CRISPR-Cas and/or Cpf1 systems may be employed to reduce if not eliminate the virulence factors of such bacteria. Likewise, *Helicobacter pylori* is known to be an etiologic agent of gastritis and peptic ulcer disease in humans. The iron acquisition system of *H. pylori* by the human lactoferrin receptor system is believed to play a major role in the virulence of *H. pylori* infection. The CRISPR-Cas and/or Cpf1 systems may be employed to reduce if not eliminate the virulence factors of this bacteria. Yet another bacteria demonstrating human tropism is *Haemophilus* influenza, a Gram negative species that requires heme and has exclusive human host specificity. In certain embodiments, the CRISPR-Cas and/or Cpf1 systems may be employed to reduce if not eliminate the virulence factors of such bacteria. The distinction between throat and skin group A *Streptococcus* has become blurred and to date there have been few advances in treatment of group A *Streptococcus* skin infections. Certain aspects of the present invention include the modification of skin group A *Streptococcus* to reduce the likelihood, if not prevent, related skin diseases, including eczema, atopic dermatitis, acne, allergic inflammation, skin hypersensitivity, UV-induced skin damage, and skin cancer.

One particular aspect of certain embodiments of the present invention relates to the treatment of acne. Acne is the most common skin disease accounting for a quarter of dermatologists' patient volume. Acne is a chronic disease that can significantly impact an individual's quality of life with social, psychological and emotional impairments. Thus, in various embodiments, bacteria are selected that, once applied to an individual's skin, is able to ameliorate acme. Such bacteria include preferably ammonia oxidizing bacteria, preferably provided to a person's skin in combination with a pharmaceutically acceptable excipient. In certain embodiments, bacteria are employed to achieve topical nitric oxide release at or near the surface of the skin and addition of urea or ammonium salts to the skin provides additional substrates that these bacteria utilize to form nitrite. While not intending to be limited thereby, such ammonia oxidizing bacteria may be selected from the group consisting of *Nitrosomonas, Nitrosococcus, Nitrosospira, Nitrosocystis, Nitrosolobus, Nitrosovibrio*, and combinations thereof. In some instances, the ammonia oxidizing bacteria is *Nitrosomonas eutropha* (*N. eutropha*). Such ammonia-oxidizing bacteria are employed to improve skin health and are able to convert ammonia to nitrite, an anti-microbial compound, and nitric oxide. Various aspects of the present invention are directed at restoring and maintaining the delicate balance of the skin microbiome.

The present invention in various embodiments is directed to a variety of consumer products including cosmetic products such as skin care products (bath preparations, skin washing and cleaning products, skin care products, eye cosmetics, lip care products, nail care products, intimate hygiene preparations, foot care), those with special effects (sunscreens, tanning agents, deodorants, anticholinergics, depilatories, shaving, fragrance), those for oral or dental hygiene and those for hair care (shampoos, conditioners, etc.)

One objective of the present invention is to achieve various health and cosmetic benefits by providing a healthy, balanced skin microbiome. Modified bacteria that are beneficial to the skin, especially those modified using CRISPR-Cas systems, are used to enhance the beneficial characteristics of skin microbiomes in a manner that purposefully exposes skin to microbes, rather than the conventional use of anti-bacterial agents to kill bacteria—including beneficial bacteria—on a person's skin. The adherence to the skin of problem flora, such as pathogenic bacteria and yeast, has been associated with numerous ailments, including skin infections, diaper rash, urinary or vaginal infections, and malodors. Use of the present invention addresses such issues in a novel and non-obvious manner.

Other embodiments are directed to prebiotic agents for use on skin. In preferred embodiments, CRISPR-Cas and/or Cpf1 modified bacteria, especially those demonstrating total or substantial tropism for humans, are employed in one or more of the above referenced products, with certain features, namely, virulence factors reduced if not eliminated. In such a manner, there is a competitive inhibition of undesired bacteria with the modified bacteria as set forth herein. In certain embodiments, the cleansing of one's skin to effectively reduce by at least about 50%, more preferably about 30%, and most preferably to reduce by at least about 25%, of native bacteria on an individual's skin portion to be addressed, is performed prior to purposefully contacting the individual's skin with one or more bacteria, and in particular, bacterial species that have been modified via employment of a CRISPR-Cas and/or Cpf1 system to reduce if not effectively compromise the virulence factors of such bacteria, and more preferably a bacteria that has a host specificity exclusive to humans.

In one particular embodiment, bacteria are modified via a CRISPR-Cas system to express a gene identified for grey hair—interferon regulatory factor 4 (IRF4). This gene is involved in regulating production and storage of melanin, the pigment that determines hair, skin and eye color. Hair greying is caused by an absence of melanin in hair. Thus, on various embodiments, bacteria are modified to express IRF4 and topical application of such bacteria to an individual's scalp provides for the prevention of hair turning grey as it otherwise would without such application of such bacteria. In still other embodiments, bacteria are modified to express levels of melanin to maintain hair color when such modified bacteria are contacted with the scalp of an individual.

Particular aspects of the present invention are directed to a method for reducing the likelihood of developing cancer in an individual human being by providing in the gut of an individual a population of beneficial bacteria selected from the group consisting of *Lactobacillus* species. To maintain such bacteria, it is preferred that the individual be administered at least 6 grams per day of fiber. Moreover, the number and/or level of particular bacteria, namely, *Roseburia* and *Faecalibacterium prausnitzii*, are increased in the individual's gut microbiome. Then the individual is administered an immune checkpoint inhibitor. It is believed that the checkpoint inhibitor's desired function is enhanced due to the presence of the bacterial population stated above. The immune checkpoint inhibitor may be selected from the group of nivolumab, pembrolizumab, pidilizumab, AMP-224, AMP-514, STI-A1110, TSR-042, RG-7446, BMS-936559, MEDI-4736, MSB-0020718C, AUR-012 and STI-A1010. In certain embodiments, the bacteria have been modified by using a clustered regularly interspaced short palindromic repeats (CRISPR) CRISPR associated protein (Cas) system or a CRISPR from *Prevotella* and *Francisella* 1 (Cpf1) system to remove a virulence factor. Any of the later CRISPR systems can also be employed for such purpose. Moreover, still other embodiments employ the provision to an individual human being's gut of a population of *Akkermansia muciniphila* bacteria. Similarly, administering at least 6 grams per day of fiber to the individual maintains a therapeutically effective amount of the *Akkermansia muciniphila* bacteria in the gut, and thus, when the individual human being is administered an immune checkpoint inhibitor, the function and positive results of such cancer treatment is enhanced.

Yet further embodiments include the increase in the levels of *Roseburia* in the gut of the individual human being. Other embodiments similarly involve increasing the levels of *Faecalibacterium prausnitzii* in the gut of the individual human being. Still others involve increasing the levels of bacterial species selected from the group consisting of *Bifidobacterium, Prevotella, Lachnospira*, and *Shigella*. It should be understood that in combating cancer, other embodiments involve administering to an individual human being bacteria that have been modified using a CRISPR-Cas system to produce p53. Such bacteria may be selected from the following in certain preferred embodiments: *Streptococcus, Actinomyces, Veillonella, Fusobacterium, Porphyromonas, Prevotella, Treponema, Neisseria Haemophilus, Lactobacillus, Capnocytophaga, Eikenella, Leptotrichia, Peptostreptococcus, Propionibacterium, Chlamydia, Shigella flexneri, Mycoplasma bacteria, H. pylori*, and *Streptomyces hygroscopicus*.

One will appreciate that this Summary of the Invention is not intended to be all encompassing and that the scope of the invention nor its various embodiments, let alone the most important ones, are necessarily encompassed by the above description. One of skill in the art will appreciate that the entire disclosure, as well as the incorporated references, figures, etc. will provide a basis for the scope of the present invention as it may be claimed now and in future applications.

BRIEF DESCRIPTION OF THE DRAWINGS

FIG. 1 is a picture of *Faecalibacterium prausnitzii*.
FIG. 2 is a picture of *Akkermansia muciniphila*.

FIG. 3 is a picture of *Roseburia*.
FIG. 4 is a picture of *Clostridium*.
FIG. 5 is a picture of *Veillonella*.
FIG. 6 is a picture of *Prevotella*.
FIG. 7 is a picture of *Propionibacterium*.
FIG. 8 is a picture of *Pseudomonas aeroginosa*.
FIG. 9 is a picture of *Klebsiella*.
FIG. 10 is a picture of *Shignella*.
FIG. 11 is a picture of *Acinetobacter baumannii*.

DETAILED DESCRIPTION OF PREFERRED EMBODIMENTS OF THE INVENTION

"CRISPR" (Clustered Regularly Interspaced Short Palindromic Repeats) loci refers to certain genetic loci encoding components of DNA cleavage systems, for example, used by bacterial and archaeal cells to destroy foreign DNA. A CRISPR locus can consist of a CRISPR array, comprising short direct repeats (CRISPR repeats) separated by short variable DNA sequences (called spacers), which can be flanked by diverse Cas (CRISPR-associated) genes. The CRISPR-Cas system, an example of a pathway that was unknown to science prior to the DNA sequencing era, is now understood to confer bacteria and archaea with acquired immunity against phage and viruses. Intensive research over the past decade has uncovered the biochemistry of this system. CRISPR-Cas systems consist of Cas proteins, which are involved in acquisition, targeting and cleavage of foreign DNA or RNA, and a CRISPR array, which includes direct repeats flanking short spacer sequences that guide Cas proteins to their targets. Class 2 CRISPR-Cas are streamlined versions in which a single Cas protein bound to RNA is responsible for binding to and cleavage of a targeted sequence. The programmable nature of these minimal systems has facilitated their use as a versatile technology that is revolutionizing the field of genome manipulation.

As used herein, an "effector" or "effector protein" is a protein that encompasses an activity including recognizing, binding to, and/or cleaving or nicking a polynucleotide target. An effector, or effector protein, may also be an endonuclease. The "effector complex" of a CRISPR system includes Cas proteins involved in crRNA and target recognition and binding. Some of the component Cas proteins may additionally comprise domains involved in target polynucleotide cleavage.

The term "Cas protein" refers to a polypeptide encoded by a Cas (CRISPR-associated) gene. A Cas protein includes proteins encoded by a gene in a cas locus, and include adaptation molecules as well as interference molecules. An interference molecule of a bacterial adaptive immunity complex includes endonucleases. A Cas endonuclease described herein comprises one or more nuclease domains. A Cas endonuclease includes but is not limited to: the novel Cas-alpha protein disclosed herein, a Cas9 protein, a Cpf1 (Cas12) protein, a C2c1 protein, a C2c2 protein, a C2c3 protein, Cas3, Cas3-HD, Cas 5, Cas7, Cas8, Cas10, or combinations or complexes of these. A Cas protein may be a "Cas endonuclease" or "Cas effector protein", that when in complex with a suitable polynucleotide component, is capable of recognizing, binding to, and optionally nicking or cleaving all or part of a specific polynucleotide target sequence.

CRISPR-Cas systems have been classified according to sequence and structural analysis of components. Multiple CRISPR/Cas systems have been described including Class 1 systems, with multi-subunit effector complexes (comprising type I, type III, and type IV), and Class 2 systems, with single protein effectors (comprising type II, type V, and type VI). A CRISPR-Cas system comprises, at a minimum, a CRISPR RNA (crRNA) molecule and at least one CRISPR-associated (Cas) protein to form crRNA ribonucleoprotein (crRNP) effector complexes. CRISPR-Cas loci comprise an array of identical repeats interspersed with DNA-targeting spacers that encode the crRNA components and an operon-like unit of cas genes encoding the Cas protein components. The resulting ribonucleoprotein complex recognizes a polynucleotide in a sequence-specific manner. The crRNA serves as a guide RNA for sequence specific binding of the effector (protein or complex) to double strand DNA sequences, by forming base pairs with the complementary DNA strand while displacing the noncomplementary strand to form a so called R-loop. RNA transcripts of CRISPR loci (pre-crRNA) are cleaved specifically in the repeat sequences by CRISPR associated (Cas) endoribonucleases in type I and type III systems or by RNase III in type II systems. The number of CRISPR-associated genes at a given CRISPR locus can vary between species.

Different cas genes that encode proteins with different domains are present in different CRISPR systems. The cas operon comprises genes that encode for one or more effector endonucleases, as well as other Cas proteins. Some domains may serve more than one purpose, for example Cas9 comprises domains for endonuclease functionality as well as for target cleavage, among others. The Cas endonuclease is guided by a single CRISPR RNA (crRNA) through direct RNA-DNA base-pairing to recognize a DNA target site that is in close vicinity to a protospacer adjacent motif (PAM). Class I CRISPR-Cas systems comprise Types I, III, and IV. A characteristic feature of Class I systems is the presence of an effector endonuclease complex instead of a single protein. A Cascade complex comprises a RNA recognition motif (RRM) and a nucleic acid-binding domain that is the core fold of the diverse RAMP (Repeat-Associated Mysterious Proteins) protein superfamily.

Type I CRISPR-Cas systems comprise a complex of effector proteins, termed Cascade (CRISPR-associated complex for antiviral defense) comprising at a minimum Cas5 and Cas7. The effector complex functions together with a single CRISPR RNA (crRNA) and Cas3 to defend against invading viral DNA. Type I systems are divided into seven subtypes.

Type III CRISPR-Cas systems, comprising a plurality of cas7 genes, target either ssRNA or ssDNA, and function as either an RNase as well as a target RNA-activated DNA nuclease. Type IV systems, although comprising typical type I cas5 and cas7 domains in addition to a cas8-like domain, may lack the CRISPR array that is characteristic of most other CRISPR-Cas systems.

Class II CRISPR-Cas systems comprise Types II, V, and VI. A characteristic feature of Class II systems is the presence of a single Cas effector protein instead of an effector complex. Types II and V Cas proteins comprise an RuvC endonuclease domain that adopts the RNase H fold. Type II CRISPR/Cas systems employ a crRNA and tracrRNA (trans-activating CRISPR RNA) to guide the Cas endonuclease to its DNA target. The crRNA comprises a spacer region complementary to one strand of the double strand DNA target and a region that base pairs with the tracrRNA (trans-activating CRISPR RNA) forming a RNA duplex that directs the Cas endonuclease to cleave the DNA target, leaving a blunt end. Spacers are acquired through a not fully understood process involving Cas1 and Cas2 proteins. Type II CRISPR/Cas loci typically comprise cas1 and cas2 genes in addition to the cas9 gene. Type II CRISR-Cas loci can encode a tracrRNA, which is partially complementary to the repeats within the respective CRISPR array, and can comprise other proteins such as Csn1 and Csn2. The presence of cas9 in the vicinity of cas1 and cas2 genes is the hallmark of type II loci. Type V CRISPR/Cas systems comprise a single Cas endonuclease, including Cpf1 (Cas12) that is an active RNA-guided endonuclease that does not necessarily require the additional trans-activating CRISPR (tracr) RNA for target cleavage, unlike Cas9. Type VI CRISPR-Cas systems comprise a cas13 gene that encodes a nuclease with two HEPN (Higher Eukaryotes and Prokaryotes Nucleotide-binding) domains but no HNH or RuvC domains, and are not dependent upon tracrRNA activity. The majority of HEPN domains comprise conserved motifs that constitute a metal-independent endoRNase active site. Because of this feature, it is thought that type VI systems act on RNA targets instead of the DNA targets that are common to other CRISPR-Cas systems. To comply with written description and enablement requirements, incorporated herein by the following references are the following patent publications: 2014/0349405 to Sontheimer; 2014/0377278 to Elinav; 2014/0068797 to Doudna; 20200190494 to Hou, et. al.; and 2020/0199555 to Zhang; U.S. Pat. No. 9,585,920 to Kovarik; US Pat. Publication No. 20170106026 to Kovarik, and U.S. Pat. No. 9,457,077 to Kovarik; US Pat. Publication No. 20170021011 to Kovarik; US Pat. Publication No. 20170173085 to Kovarik.

In certain embodiments, it may be advantageous to genetically modify a gut mucosal-associated bacteria with polynucleotides and as taught herein to express or overexpress the polynucleotides as taught herein or to produce or overproduce the polypeptides, such as butyrate and acetate, directly into the vicinity of, or within the gut mucosal barrier of a human. In a preferred embodiment, the gut mucosal-associated bacteria may by any bacteria from the species *F. prausinitzii, Prevotella intermedia,* and/or *Akkermansia muciniphilla*. Such overproduction may be realized by genetic modification tools involving recombinant DNA technologies, genome editing such as by using tools based on CRISPR/cas-like systems, or by classical mutation selection systems.

In an embodiment, the genetically modified host cell may be any bacteria, particularly one which is not from a species of bacteria that naturally occurs or lives in the vicinity of or within the gut mucosal barrier of a mammal. Non-limiting examples of such bacteria include any beneficial isolated intestinal bacterial strains, e.g. probiotic bacteria, particularly strains selected from the genera *Lactococcus, Lactobacillus*, or *Bifidobacterium* may be used. In addition, strict anaerobic intestinal bacteria may be used such as those belonging to the genera known to occur in the human intestinal tract. As described herein, in various embodiments, strictly anaerobic bacteria are encapsulated or microencapsulated to avoid contact with oxygen, and are delivered to a human such that the encapsulation is dissolved or fractured to release such bacteria in a portion of the body, e.g. gut, where it can thrive.

Certain embodiments employ the bacterium *Flavobacterium akiainvivens*, which was discovered in 2012 on the plant *Wikstroemia oahuensis*, or "akia," which is a flowering shrub endemic to Hawaii. That bacterium has been found on that plant and no other. The bacterium forms 2- to 3-millimeter diameter colonies that range from cream to off-white in color and wet to mucoid in viscosity, and (it) was isolated from decaying *Wikstroemia oahuensis* collected on the island of Oahu.

Certain embodiments are directed to the targeted manipulation of the gut microbiome for therapeutic applications, such as the manipulation of the gut microbiome achieved by altering the microbiota population and composition, or by modifying the functional metabolic activity of the microbiome to promote health and restore the microbiome balance. There has been recent progress in the engineering of gut commensals, which also presents great potential for biomedical applications. Specifically, in *Bacteroides thetaiotaomicron*, components for tunable gene expression were developed and characterized and expected functional outputs were observed in mice after administration of these engineered *B. thetaiotaomicron*. Thus, one aspect of various embodiments is to harness such engineered commensals, especially *F. prausntizii* for the overproduction of butyrate, for therapeutic purposes.

*F. prausntizii* was first isolated in 1922 by C. Prausnitz. Morphologically, *F. prausntizii* is a Gram-negative, non-motile and non-sporeforming rod with a diameter of 0.5 to 0.9.times.2.4 to 14.0.mu.m. *F. prausntizii* is a strictly anaerobic bacterium that produces butyrate, formate, D-lactate and $CO_2$ but no hydrogen as fermentation products and *F. prausntizii* growth is inhibited by acidic pH and bile salts. The amount of *F. prausntizii* in the healthy human gut is linked to diet. Inulin-derived prebiotics have been shown to significantly increase *F. prausntizii* concentration in the gut. *F. prausntizii* is statistically linked to eight urinary metabolites: dimethylamine, taurine, lactate, glycine, 2-hydroxyisobutyrate, glycolate, 3,5-hydroxylbenzoate and 3-aminoisobutyrate. It is believed that *F. prausntizii* has pronounced anti-inflammatory effects. While not bound by theory, *F. prausntizii* may induce an increased secretion of an anti-inflammatory cytokine interleukin 10, and a decreased secretion of pro-inflammatory cytokines like interleukin 12 and tumor necrosis factor—a production. It is further believed that *F. prausntizii* has the ability to suppress inflammation, and it is hypothesized that this is due to metabolite(s) secreted by *F. prausntizii*, including but not limited to butyrate. The number of *F. prausntizii* is significantly higher in the gut of healthy subjects as compared to IBD and it is believed that *F. prausntizii* is crucial to gut homeostasis and disease protection.

*F. prausntizii* is one of the most abundant bacteria in a healthy human gut and is believed to have a positive effect on the human gut health. *F. prausntizii* belongs to the *Clostridium leptum* group (*Clostridium* cluster IV), belonging to phylum Firmicutes (Lineage: Bacteria; Firmicutes; Clostridia; Clostridiales; Ruminococcaceae; *Faecalibacterium; Faecalibacterium prausnitzii*). *F. prausntizii* has been previously called *Fusobacterium prausnitzii* (also cited as *F. prausntizii*), with it only distantly being related to Fusobacteria and more closely related to members of *Clostridium* cluster IV.

Moderate butyrate levels can prevent high-fat-diet-induced insulin insensitivity through epigenetic regulation, and mitochondrial beta-oxidation. *F. prausntizii* is one of the unique organisms that reduce various autoimmune diseases, especially type-1 diabetes via the modulation of gut epithelium homeostasis and immune system. Studies associated with gut microbiota and type-1 diabetes have a lower proportion of butyrate-producing organisms, such as Firmicutes and *Clostridium*, which protects against autoimmune diabetes. While not bound by theory, *F. prausntizii* is believed to regulate the development of autoimmune diabetes via butyrate dependent complementary pathways. An abundant quantity of butyrate can lower the gut barrier function and enhance cell apoptosis, with high levels of butyrate stimulating GLP-1 secretion and enhancing insulin sensitivity through cAMP signals, such as PKA and Epac, which inhibit gastric emptying. Due to the inhibition of gastric emptying, butyrate can be excreted slowly and accumulates, influencing the anti-inflammatory potential, pH, and oxidative stress.

Butyrate is the major product of carbohydrate fermentation in the colon. Butyrate modulates several processes and is a known anti-proliferative agent. In cultured cell lines, butyrate inhibits DNA synthesis and cell growth, mainly by inhibiting histone deacetylase. Butyrate is also suggested to regulate the citric acid cycle, fatty acid oxidation, electron transport and TNF-.alpha. signaling. Animal studies have indicated that butyric acid may have antineoplastic properties, which means that it may protect against colon cancer. As dietary fiber is protective against colon cancer because carbohydrates entering the large bowel stimulate the production of butyrate. Butyrate has also been suggested to provide protection against ulcerative. *F. prausntizii* is an important producer of butyrate, and the decrease of *F. prausntizii* has been correlated to lower concentrations of fecal butyrate in healthy human subjects and it is believed that *F. prausntizii* plays an important role in the protection of the colon. While not bound by theory, the benefits of butyrate are thought to depend on several aspects, such as time of exposure and butyrate amount. Increased butyrate production by *F. prausntizii* is therefore a desired outcome and employment of CRISPR systems to achieve the same, employing the known genes involved in butyrate by *F. prausntizii* is one important embodiment of the present invention.

Studies have shown that there was a statistically significant reduction in the *F. prausntizii* abundance during both fiber-free and fiber-supplemented diets, but it is postulated that the reduction during the fiber-supplemented diet was due to the use of pea fiber, which is not believed to support the growth of *F. prausntizii*, and thus, with the proper fiber being employed, the increase in butyrate production is achieved. In situations where there is insufficient fiber for the beneficial bacteria to consume, the bacteria end up eroding the mucus of the gut and leads to epithelial access by mucosal pathogens.

The relative abundance of Bacteroidetes and Firmicutes has been linked to obesity, with the Firmicutes ratio being significantly higher in obese individuals. It is believed that a high number of *F. prausntizii* leads to higher energy intake, because *F. prausntizii* is responsible for a significant proportion of fermentation of unabsorbed carbohydrates in the gut.

*F. prausntizii* cultivation has proven difficult because the bacterium is a strictly obligatory anaerobe that does not tolerate any oxygen. As described herein, encapsulation of *F. prausntizii* is achieved such that it can be effectively delivered such that the encapsulated structure can degrade or be fractured at an appropriate time and place to release such bacteria to a human to derive beneficial results, e.g. the increased production of butyrate. For example, microencapsulation, in a xanthan and gellan gum matrix, and a subsequent freeze-drying protocol can be employed to achieve this result.

In other embodiments, the bacterial composition employed includes both *F. prausntizii* and *Akkermansia muciniphila*, another abundant member of the human gut microbiota. It is further believed that *Faecalibacterium prausnitzii* plays a vital role in diabetes and can be used as an intervention strategy to treat dysbiosis of the gut's microbial community that is linked to the inflammation, which precedes autoimmune disease and diabetes.

The microbiota in adults is relatively stable until the persons get 60 years old. Gut alterations lead to elevated gut permeability and reduced gut mucosal immunity, contributing to the development of various cancers, autoimmune disorders, inflammatory bowel diseases, metabolic syndrome and neurodegenerative diseases. The resultant elevated intestinal permeability is a consequence of reduced expression of tight junction proteins that favors the uncontrolled passage of antigens and enables the translocation of bacterial lipopolysaccharide to the gut connective tissues and to the blood circulation, causing insulin resistance and metabolic endotoxemia.

The gastrointestinal tract pH normally ranges between 5 and 5.5 in the ileum and the colon has a range from 6.6 to 7.0, which is one of the main factors in constructing the shape of the microbial communities in the colon. Diet compositions containing fermentable polysaccharides are regulators of the intestinal pH, which facilitates a more acidic environment through the end-products of SCFAs in the gut.

Stool pH becomes more alkaline with the increase in age and differs significantly between genders with higher consumption of animal protein being one possible mechanism for higher pH. Such alkalinity is generally caused due to its alkaline metabolites produced by proteolytic putrefactive bacteria, such as *Bacteroides, Propionibacterium, Streptococcus, Clostridium, Bacillus*, and *Staphylococcus*.

An individual generally represents a unique collection of genera and sub-species and it may be different based on the diet (vegetarian or Western with high protein or fat), the age of the host organism, genetic and environmental factors. Diet greatly influences the diversity of the microbiota in the gut and the microbiota is genetically well equipped to utilize various nutritional substrates to maintain a normal gut microbiota pattern. An adequate SOFA (butyrate) production level is essential for gut integrity and butyrate-producing bacteria, such as *Eubacterium, Fusobacterium, Anaerostipes, Roseburia, Subdoligranulum*, and *Faecalibacterium*, but especially, *F. prausntizii*, have the potential of anti-inflammatory effect and help to reduce bacterial translocation, improve the organization of tight junctions and stimulate the secretion of mucin to maintain the integrity of the gut, with beneficial effects against inflammation in the gut.

Inflammation is one of the major pathophysiological factors leading to insulin resistance and progressively causes type-2 diabetes. *F. prausntizii* counts significantly decreased in diabetic individuals with negative correlation to glycated hemoglobin HbA1c values. Along with *Akkermansia muciniphila*, *F. prausntizii* is abundantly found in individuals with normal glucose tolerance compared to the pre-diabetic subjects. *F. prausntizii* can convert acetate into butyrate using butyryl-CoA: Acetate CoA-transferase (BUT) pathways, thereby providing a balanced pH in the gut.

With the guidance provided herein, as well as the numerous references incorporated by reference herein, one of skill in the art will understand the feasibility of using engineered bacteria to directly manipulate the functional output of the microbiota without major modulation of the microbiota population and composition. Components in the normal diet and/or employing prebiotics and engineered probiotics are therefore harnessed to render a targeted effect on the host through modulating the functional output of the microbiome.

*F. prausntizii* is a multi-skilled commensal organism and a chief member of human microbiota. It is broadly distributed in the digestive tract of mammals and also in some insects. It is rich in the hind gut rather than in the stomach, as well as jejunum. The consumption of a higher quantity of animal meat, animal fat, sugar, processed foods, and low fiber diet (the typical westernized diet) reduces the count of *F. prausntizii*, while a high-fiber (vegetables and fruits) and low meat diet enhance the count of *F. prausntizii*. It is known to consume a variety of diet containing polysaccharides, such as the prebiotic inulin, arabinoxylans, apple pectin, oligofructose, resistant starch, fructan supplement, pectins and some host-derived carbon sources (including d-glucosamine and N-Acetyl-d-glucosamine). Meta-analyses also show that the increased consumption of fiber significantly reduces the risk of mortality.

The discovery of the clustered regularly interspaced short palindromic repeats (CRISPR) and the CRISPR-associated nuclease 9 (Cas9) system, has led to an array of strategies to manipulate the gut microbiome with precision. Engineered phage (with the CRISPR-Cas9 system) can be employed to target pathogenic bacteria, or remove a population of bacteria that aids pathogenic bacterial growth, thereby fine-tuning and restoring the balance of the gut microbiome. CRISPR/Cas9 can also be used to manipulate and differentiate genetically heterogeneous bacteria, even of the same species. Unlike conventional drugs, the CRISPR/Cas9 system targets specific bacteria at the gene level to selectively remove pathogens, virulence factors, genes of undesired expressed proteins, etc. and can further be used as an antimicrobial adjuvant to improve antibiotic treatment. Citorik et. al. demonstrated how CRISPR/Cas9 can be delivered using bacteriophages, targeting the ndm-1 gene, which codes for the broad-spectrum carbapenemase, New-Delhi metallo-.beta.-lactamase. Ndm-1 targeting CRISPR/Cas9 specifically eliminated *E. coli* harboring the gene without affecting wild-type, or other, *E. coli* strains present in a synthetic consortium of microbes. Other examples include the re-sensitization of bacteria to antibiotics and immunization of bacteria to incoming plasmids conferring antibiotic resistance using temperate phages. Yosef et al. used CRISPR/Cas9 to target ndm-1 and ctx-M-15, which expresses a broad-spectrum beta-lactamase, and effectively selected the transduced bacteria that were antibiotic-sensitive. Thus, CRISPR/Cas9 may be employed to manipulate the gut microbiome by discriminating at the gene level to change the characteristics and functional output of the gut microbiome for therapeutic applications.

In particular embodiments of the present invention, the bacterial formulation may include bacteria selected from the group consisting of *Nitrosomonas eutropha* and *Propionibacterium*. More particularly, the equilibrium of a bacterial population of the region of the skin of the individual is modified to increase the number of *Propionibacterium* bacteria and to decrease the number of *Staphylococcus* bacteria on the individual's skin in such region. In other embodiments, the bacterial formulation includes the bacteria *Staphylococcus aureus* that has been modified by employing a CRISPR-Cas or Cpf1 system to interfere with *S. aureus* virulence regulation involving the Agr quorum-sensing signaling molecule. In several embodiments, the bacterial formulation comprises a bacteria that has a tropism specific for the human species. In others, the bacterial formulation comprises at least two of the bacteria selected from the group consisting of: *Prevotella; Lactobacillus johnsonii; Bacteroides fragilis, Lactobacillus ruminus* and *L. infantitis*. In certain embodiments the bacteria is an ammonia oxidizing bacteria. In other embodiments, the region of the skin to which the bacterial formulation is applied is the scalp. In various embodiments, rather than using a wild-type bacteria, the bacteria employed is one that has been modified by CRISPR-Cas or CRISPR-Cpf1 to delete a functional virulence factor from the bacteria. In particular embodiments, the method includes administering to the skin a bacteria that produces tomatidine. In others, the bacteria produces p53. Thus, in some embodiments, the method involves use of bacteria wherein a CRISPR-Cas or CRISPR-Cpf1 system is employed to insert a gene for the production of tomatidine and/or p53 into at least one of the bacteria in the bacterial formulation. In others, a CRISPR-Cas or CRISPR-Cpf1 system is employed to insert one or more genes into the bacteria comprising the bacterial formulation to facilitate the oxidizing of ammonia by the bacteria. To further enhance the ability of desired bacteria to be maintained on the skin of an individual, certain methods further comprise administering to the individual's skin a prebiotic that comprises a nutrient source for the bacteria that is assimilated by the bacteria, and preferably one that is not digestible by the individual. In particular embodiments, the method further includes administering to the skin an extract derived from a helminth selected from the group consisting of *Capillaria hepatica, Dicrocoelium dendriticum, Ascaris lumbricoides, Enterobius vermicularis, Trichuris trichiura, Ancylostoma duodenale, Necator americanus, Strongyloides stercoralis, Haemonchus contortus,* and *Trichinella spiralis*. In still others, the bacterial formulation includes at least one arabinogalactan. Yet others include at least one of the following: *L. infantitis,* and *L. johnsonii*. In a particular embodiment, the bacterial formulation includes at least one bacteria modified via a CRISPR-Cas system to express a gene encoding interferon regulatory factor 4.

As for lotions of the present invention, in preferred embodiments, there is an objective to limit if not preclude the use of phthalates, which are extremely toxic and are believed to also be human carcinogens. Thus, in preferred embodiments of the present invention, such lotions do not employ such toxic agents, and in particular agents toxic to bacterial species for which the inventors suggest be used, e.g. those modified to reduce pathogenicity, virulence factors, etc, so as to establish a population of such modified bacteria on a person's skin, and in such a manner, reduce the incidence of skin infections and diseases. Thus, lotions, creams, gels, etc. that include such toxic agents, including but not limited to phthalates, are not employed, but rather, lotions that provide an environment for the bacteria as set forth herein to survive and to thus be available to provide benefits to the skin of individuals to which they are applied, are particularly preferred.

Healthy, normal skin exhibits a slightly acidic pH in the range of 4.2-5.6, which aids in the prevention of pathogenic bacterial colonization, regulation of enzyme activity, and maintenance of a moisture-rich environment; however, after the age of 70, the pH of skin rises significantly, stimulating protease activity. Thus, one objective of several embodiments of the present invention is directed to lowering the pH of the skin of an individual, especially those at about the age of 70, so as to encourage a skin environment conducive to the proliferation of one or more bacteria that have been modified to promote skin health and to reduce the ability of undesired bacteria from colonizing the skin of the person. Probiotic metabolism frequently produces acidic molecules, lowering the pH of the surrounding environments seen with Lactobacilli producing free fatty acids (FFAs) and conjugated linoleic acid (CLA) during the fermentation process. Thus, the use of probiotics is employed to restore the normal skin pH and consequently return protease activity levels closer to those seen in young, healthy skin.

The main microbes that reside on human skin can be divided into four phyla: Firmicutes, Actinobacteria, Proteobacteria, and Bacteroidetes. *Staphylococcus* spp. and *Corynebacterium* spp. are the dominant bacteria at the genus level. Significantly fewer *Corynebacterium* spp. have been observed in cachexia patients compared to healthy subjects. These results suggest that the presence of cancer and cachexia alters human skin bacterial communities. Understanding the changes in microbiota during cancer cachexia may lead to new insights into the syndrome.

Competitive inhibition is relied upon in various embodiments to advance the repopulation of skin with beneficial microbes. In one embodiment, repopulating an individual's skin with beneficial bacteria, preferably in balanced percentages and having preferred species provided, can be used in conjunction with an antimicrobial composition. Preferably, an antimicrobial is first administered to suppress or eradicate the resident populations of bacteria on a person's skin, including any abnormal organisms or pathogenic bacteria, then the normal flora is repopulated by the administration of at least one of the modified bacteria as described herein, including those modified using CRISPR-Cas and/or Cpf1 systems to delete certain portions of genes or to add certain genes to facilitate the colonization of a person's skin with beneficial bacteria that maintain the general health of a person's skin.

In various embodiments, cosmetics are provided that provide for a medium favorable for maintaining a desired physico-chemical balance of the skin without favoring the development of pathogenic microorganisms. To achieve this objective, certain oligosaccharides that are metabolized by several beneficial strains of the skin microflora, such as *Micrococcus kristinae, Micrococcus sedentarius, Staphylococcus capitis, Corynebacterium xerosis* and *Lactobacillus pentosus*, are employed in formulations, in conjunction with one or more of the modified bacteria as described herein. In particular embodiments, oligosaccharides are employed in formulations for the skin that include one or more of *Lactobacillus pentosus, Micrococcus kristinae, Gardnerella vaginalis, Propionibacterium avidum* and *Propionibacterium granulosum*. As stated herein above, it is often beneficial to further acidify the culture medium, and this can be achieved, for example, by employing Lactobacilli to produce in particular lactic acid to achieve pH reducing effects.

In certain embodiments, the present invention is directed to cosmetic compositions having at least one oligosaccharide chosen from the group consisting of gluco-oligosaccharides, fructo-oligosaccharides, and galacto-oligosaccharides and mixtures thereof. In addition to the oligosaccharide constituent, the cosmetic compositions of particular embodiments of the invention may contain other ingredients, but caution is warranted as one objective is to avoid incorporating ingredients whose properties would interfere with the development of the beneficial skin microflora and the preservation of acidic conditions. Thus, it is advisable to avoid incorporating bactericidal ingredients in proportions which would annihilate the endogenous microflora, or ingredients which confer a pronounced basic character on the composition. For example, in preferred embodiments, reduction if not elimination of ionic surface-active agents, such as sodium lauryl sulfate, is advisable, as well as other well known agents having bactericidal properties. Instead, use of a non-ionic surface-active agent such as an alkyl glucoside or a dialkyl ester may be employed in various embodiments. Preferably, cosmetic compositions of the invention contain an acidic buffer which adjusts the pH of the composition to about pH 4 to 7 range, preferably about 5 to 6.5 pH. At such range, especially on the lower side, mutualistic flora such as Staphylococci, Micrococci, *Corynebacterium* and Propionibacteria preferably grow but not transient bacteria such as Gram negative bacteria like *Escherichia* and *Pseudomonas* or Gram positive ones such as *Staphylococcus aureus* or *Candida albicans*.

Certain other embodiments are directed to the rebalancing of the skin microbiota using antimicrobials with selective action. For example, in certain embodiments a balance of species and characteristics is sought to provide skin formulations that maintain a well-balanced bacterial flora, and especially one that includes one or more of the modified bacteria as described herein. Thus, one particular aspect of various embodiments is directed to the provision of embodiments targeted to reduce undesired body odor (and in various embodiments, actively provides microbes that generate desired odors and reduces the effects of malodors by other bacteria) which can be gender specific.

In various formulations of the present invention, the use of bacteria able to generate lactic acid to serve as a moisturizing factor, still others that produce hyaluronic acid to improve skin hydration and elasticity, and that include sphingomyelinase to generate ceramide to enhance skin barrier function, are preferred compositions. One aspect of the present invention is directed to restoring homeostasis to treat certain skin diseases by remedying the dysbiosis in the skin habitat by establishing a desired colony of various diverse bacteria, especially those modified as described herein to establish and maintain a healthy skin condition on an individual's skin.

In one embodiment of the present invention, bacteria species are employed that have been modified via CRISPR-Cas systems to reduced malodor without the employment of aluminum or zirconium salts. Such modified bacteria suppress malodor and counteract or suppress sweat malodor. Even more preferred bacteria have been modified to express compounds of a pleasant and desirable scent. Such bacteria can thus provide amounts of a perfume scent that is pleasant to a person and that can at least partially mask the unpleasant body odor smells produced by a person. Splicing in such "perfume" genes into bacteria using the CRISPR-Cas system is one way to accomplish this objective. Use of such bacteria on a person's skin, and in particular under armpits where the particular type of bacteria is selected to grow and out-complete other microbes in such a moister environment (as compared to elbows, etc.) can be used to enhance the desired smells of one's body while limiting the amount of traditional antiperspirants and deodorants conventionally employed. Still other embodiments include the use of bacteria that utilize as their food source the very bacteria that produce malodors. In such a fashion the desired bacteria feed off of the products produced by undesired bacteria on a person's skin, and in particular under an individual's arm, so that undesired body odor is reduced and without the use of traditional chemicals and compounds as previously discussed.

To further comply with written description and enablement requirements, the following patents and patent publications are also incorporated herein by this reference in their entireties: are the following: U.S. Pat. No. 8,815,538 to Lanzalaco, et al.; 20150374607 to Lanzalaco, et al.; 20150361436 to Hitchcock et al.; 20150353901 to Liu et al.; U.S. Pat. No. 5,518,733 to Lamothe, et al.; 20150259728 to Cutliffe et al. U.S. Pat. No. 8,685,389 to Baur; 20140065209 to Putaala et al.; U.S. Pat. No. 8,481,299 to Gueniche; WO 2011029701 to Banowski; 20150071957 to Kelly; 20150202136 to Lanzalaco; 20150017227 to Kim; U.S. Pat. No. 7,820,420 to Whitlock; 20150202136 to Lanzalaco et al.; U.S. Pat. No. 5,518,733 to Lamothe, et al.; U.S. Pat. No. 8,815,538 to Lanzalaco et. al; U.S. Pat. No. 8,951,775 to Castiel; WO 2006/07922; U.S. Pat. No. 9,234,204 to Qvit-Raz et al.; U.S. Pat. No. 8,758,764 to Masignani, et al.; U.S. Pat. No. 9,028,841 to Henn et al.; 20160008412 to Putaala et al., 20150064138 to Lu; 20150017227 to Kim; United States Patent Application No. 20160314281 to Apte; 20160151427 to Whitlock et al.; 20140044677 to Raz et al.; 20160168594 to Zhang et al. U.S. Pat. Nos. 7,267,975; 9,288,981; United States Patent Application No. 20160122806; U.S. Pat. No. 9,234,204 to Noga Qvit-Raz; US20120301452; 20160271189 to Cutcliffe; US Pat. Applic. No. 2008242543; 20160040216 to Wilder; and United States Patent Application No. 20160089315 to Kleinberg, et al., 20070148136 to Whitlock et al., 20190059314 to Aharoni; 20200009268 to Scholz and 20200009185 to Shin;

In certain embodiments, one aspect of the present invention is directed to the treatment of acne by using probiotic treatments that include effective amounts of *Staphylococcus epidermidis* and/or *Lactobacillus plantarum* to inhibit *P. acnes* growth, which are believed to produce succinic acid, shown to inhibit *P. acnes* growth. CRISPR-Cas and/or Cpf1 systems are used to modify such bacteria in a manner that reduces the occurrence of acne, such as by altering the expression of genes so that the amount of succinic acid on a person's skin is increased.

Certain aspects of the present invention relate to a composition including ammonia oxidizing bacteria to increase production of nitric oxide and/or nitric oxide precursors in close proximity to a person's skin. More specifically, applying a composition of an ammonia oxidizing bacteria to skin during or after bathing to metabolize urea and other components of perspiration into nitrite and ultimately into Nitric Oxide (NO) results in a natural source of NO. One aspect of the present invention causes topical nitric oxide release at or near the surface of the skin where it can diffuse into the skin and have local as well as systemic effects. This naturally produced nitric oxide can then participate in the normal metabolic pathways by which nitric oxide is utilized by the body. Adding urea or ammonium salts to the skin provides additional substrates that these bacteria utilize to form nitrite. As used herein, the phrase near the surface is defined as adjacent to or in close proximity to, but need not be in contact with the surface.

In still other embodiments, CRISPR systems are used to modify the genera *Propionibacterium, Corynebacterium* and *Staphylococcus*, and in particular *S. epidermidis*, which are among the most common groups on a person's skin, with such modifications making such species more amenable to growth on the skin, thus providing for competitive inhibition of non-modified bacteria on the skin. As one of skill in the art will appreciate, a suitable topical composition comprising a population of the above bacteria can be, in various embodiments, a cream, lotion, emulsion, gel, ointment, liquid or spray. In one embodiment, the topical composition is formulated to provide at least about 10.sup.2 bacteria per cm.sup.2. In another aspect, a method of treatment is provided, wherein a composition as described herein is topically applied to the skin and in certain embodiments, topically applying includes topically applying to a mucosal surface (nasal, vaginal, rectal, oral surfaces) of a person. A suitable lotion may also include amounts of sugars that the various *Lactobacillus* microorganisms may assimilate to survive and thrive. These sugars and life bacteria-supporting compounds are known to those in the art and as otherwise referenced in various incorporated writings. In still other embodiments, pulverized compositions of helminth collections and bacteria preferably obtained from Amish-soils, may be employed in various administrative modes, including but not limited to lotions, creams, and other topical applications.

Because skin cells turn over every 4 weeks, differentiating from stem cells deep within the epidermis and hair follicles, they eventually slough off from the upper layer as cornified (enucleated, dead) cells. The skin microbiome is vastly different from the gut microbiome, which consists primarily of members of Firmicutes and Bacteroidetes divisions. The skin is also different from the gut in that there is a low level of interpersonal variation of skin microbiomes, which is not the case in gut studies. Regardless, there is a low level of deep evolutionary lineage diversity, with only six of the more than 70 described bacterial divisions associated with the skin, and approximately the same number for the gut, which compares to a vast array of bacteria in soil.

A subject of the invention is also the topical use of an effective amount of at least one probiotic microorganism according to the invention, especially of the *Lactobacillus* and/or *Bifidobacterium* sp. Genus, and in particular of the *Lactobacillus paracasei* ST11 strain, to reduce the likelihood of seborrhoeic dermatosis associated with oily skin or skin with an oily tendency. Microorganisms suitable for this aspect of the invention include an ascomycetes, such as *Saccharomyces, Yarrowia, Kluyveromyces, Torulaspora, Schizosaccharomyces pombe, Debaromyces, Candida, Pichia, Aspergillus* and *Penicillium*, bacteria of the genus *Bifidobacterium, Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*, and mixtures thereof.

As ascomycetes is particularly suitable for particular embodiments of the present invention, one may desire the use of *Yarrowia lipolitica* and *Kluyveromyces lactis*, as well as *Saccharomyces cereviseae, Torulaspora, Schizosaccharomyces pombe, Candida* and *Pichia*, all of the same preferably modified via CRISPR-Cas or Cpf1 systems to reduce virulence factors associated with the same. Specific examples of probiotic microorganisms also suitable for the invention include: *Bifidobacterium adolescentis, Bifidobacterium animalis, Bifidobacterium bifidum, Bifidobacterium breve, Bifidobacterium lactis, Bifidobacterium longum, Bifidobacterium infantis, Bifidobacterium pseudocatenulatum, Lactobacillus acidophilus* (NCFB 1748); *Lactobacillus amylovorus, Lactobacillus casei* (Shirota), *Lactobacillus rhamnosus* (strain GG), *Lactobacillus brevis, Lactobacillus crispatus, Lactobacillus delbrueckii*(subsp *bulgaricus, lactis*), *Lactobacillus fermentum, Lactobacillus helveticus, Lactobacillus gallinarum, Lactobacillus gasseri, Lactobacillus johnsonii* (CNCM 1-1225), *Lactobacillus plantarum, Lactobacillus reuteri, Lactobacillus salivarius, Lactobacillus alimentarius, Lactobacillus curvatus, Lactobacillus casei* subsp. *casei, Lactobacillus sake, Lactococcus lactis, Enterococcus (faecalis, faecium), Lactococcus lactis* (subsp *lactis* or *cremoris*), *Leuconostoc mesenteroides* subsp *dextranicum, Pediococcus acidilactici, SporoLactobacillus inulinus, Streptococcus salvarius* subsp. *thermophilus, Streptococcus thermophilus, Staphylococccus carnosus, Staphylococcus xylosus, Saccharomyces (cerevisiae* or else *boulardii), Bacillus (cereus* var *toyo* or *subtilis), Bacillus coagulans, Bacillus licheniformis, Escherichia coli* strain nissle, *Propionibacterium freudenreichii*, and mixtures thereof. In other embodiments, probiotic microorganisms for use in the invention are derived from the group of lactic acid bacteria, such as, in particular, *Lactobacillus* and/or *Bifidobacterium*. In particular, various embodiments use lactic acid bacteria such as *Lactobacillus johnsonii, Lactobacillus reuteri, Lactobacillus rhamnosus, Lactobacillus paracasei, Lactobacillus casei* or *Bifidobacterium bifidum, Bifidobacterium breve, Bifidobacterium longum, Bifidobacterium animalis, Bifidobacterium lactis, Bifidobacterium infantis, Bifidobacterium adolescentis, Bifidobacterium pseudocatenulatum*, and mixtures thereof. Most preferably for particular embodiments, CRISPR modified bacteria of the following are employed: *Lactobacillus johnsonii, Lactobacillus paracasei, Bifidobacterium adolescentis* and *Bifidobacterium longum*, respectively deposited according to the Treaty of Budapest with the Institut Pasteur (28 rue du Docteur Roux, F-75024 Paris cedex 15) on 30 Jun. 1992, 12 Jan. 1999, 15 Apr. 1999 and 15 Apr. 1999 under the following designations: CNCM 1-1225, CNCM I-2116, CNCM 1-2168 and CNCM 1-2170, and the *Bifidobacterium lactis* (Bb 12) (ATCC27536) or *Bifidobacterium longum* (BB536) genus. The *Bifidobacterium lactis* (ATCC27536) strain can be obtained from Hansen (Chr. Hansen A/S, 10-12 Boege Alle, P.O. Box 407, DK-2970 Hoersholm, Denmark); *Lactobacillus paracasei* ST11 strain deposited according to the Treaty of Budapest with the Institut Pasteur (28 rue du Docteur Roux, F-75024 Paris cedex 15) on 12 Jan. 1999 under the designation CNCM 1-2116, and/or a fraction thereof and/or a metabolite thereof.

According to one variant embodiment, the invention relates to the use, in addition to a first probiotic microorganism, as defined above, especially of the *Lactobacillus* and/or *Bifidobacterium* sp. genus, of at least an effective amount of at least a second microorganism, distinct from said first microorganism. Such a second microorganism may be an ascomycetes, such as *Saccharomyces, Yarrowia, Kluyveromyces, Torulaspora, Schizosaccharomyces pombe, Debaromyces, Candida, Pichia, Aspergillus* and *Penicillium*, bacteria of the *Bacteroides, Fusobacterium, Melissococcus, Propionibacterium, Enterococcus, Lactococcus, Staphylococcus, Peptostrepococcus, Bacillus, Pediococcus, Micrococcus, Leuconostoc, Weissella, Aerococcus, Oenococcus, Lactobacillus* or *Bifidobacterium* genus, and mixtures thereof.

In other embodiments, CRISPR-Cas and or Cpf1 systems are used to modify at least one of *Enterobacter aerogenes, Acinetobacter baumannii*, and *Klebsiella pneumoniae*, which are three gram negative bacteria commonly found on the skin, and which utilize fatty acids in a manner that affects bacterial phenotype. The modifications to such bacteria include those effective in enhancing the beneficial traits of such bacteria for a person's skin and the reduction of respective virulence factors of the bacteria. In such a manner, one aspect of the present invention is to maintain a microbiome in a healthy, balanced state and/or returning a microbiome to a balanced state by providing certain desirable microorganisms with sufficient nutrients to thrive, and thereby outcompete and/or kill the undesirable bacteria. It has been found that *Corynebacterium jeikeium* ("*C. jeikeium*"), *Staphylococcus epidermidis* ("*S. epidermidis*"), and *Propionibacterium acnes* ("*P. acnes*"), present on both the face and forearms of humans, can be used to address dry skin conditions and diseases on such tissues. Modifications of virulence factors of pathogenic bacteria associated with such conditions, as well as combining such modified bacteria with other commensal microorganisms, is one aspect of the present invention. Such bacteria include: Alpha proteobacteria, Beta proteobacteria, Gamma proteobacteria, Propionibacteria, Corynebacteria, Actinobacteria, Clostridiales, Lactobacillales, *Staphylococcus, Bacillus, Micrococcus, Streptococcus*, Bacteroidales, Flavobacteriales, *Enterococcus*, and *Pseudomonas*.

Various embodiments of the present invention are directed to a method for reducing the likelihood of the onset of a disease, such as cancers, by administering to a subject a therapeutically effective amount of a composition comprising a probiotic microorganism, rather than attempting to alter the eukaryotic genome of the individual. It is believed that by merely modifying a person's microbiome, whether it be their gut, oral or skin microbiome, it is possible to treat, if not protect such individuals from a vast array of previously devastating diseases of man. For example, *Helicobacter* species have been associated with enhanced carcinogenesis including liver cancer, colon cancer, and mammary carcinoma. Probiotic formulations containing lactic acid bacteria have been shown to reduce the incidence of chemically mediated hepatocellular carcinoma and colon cancer. Bacteria that have been modified using a CRISPR-Cas system to purposefully excise or interfere with virulence factors of particular pathogenic bacteria, and the employment of such modified bacteria to adjust the population of a person's microbiome, is an effective way to treat a vast number of historically difficult diseases.

The balance between health and disease is imperiled by infections. When immunity is lowered, the human body is less able to eradicate cancer cells, which would otherwise be kept in check. In certain embodiments, a mushroom component is also employed to achieve desired health effects. For example, in various embodiments, the mushroom mycelium is used to protect against viruses that cause disease in humans, such as those mushrooms derived or obtained from *Antrodia, Fomes, Fomitopsis, Ganoderma, Inonotus, Schizophyllum, Phellinus, Piptoporus, Trametes* and other taxa in the Polyporaceae. Ethyl alcohol/water extraction techniques are employed on living mycelium to obtain antiviral compounds and that are effective to reduce viruses that cause inflammation and immune deactivation which are contributory to oncogenesis. Such extracts reduce the pathogenicity of viruses and by doing so, reduce cancer risk and also significantly enhance the benefits of other anticancer drugs to increase the quality of life of cancer patients. Used in combination with the various other aspects of the present invention, including the beneficial modified bacterial species as described herein, a person's overall health is improved by reducing the chances of infection, inflammation and cancer, by improving and adjusting the microbiome of individuals and by having certain mushroom derived compounds administered, (some of which can be inserted into the genome of bacteria via the CRISPR-Cas system) such that beneficial compounds are administered to individuals to prevent and treat various diseases, such as but not limited to, cancer.

In particular embodiments, a method of the present invention involves a method of improving the health of a person's skin microbiome by identifying a skin region to be treated in terms of age, ethnicity, region of the body and age of the person and then applying a skin commensal prebiotic agent adapted to address the skin region; wherein the prebiotic comprises at least one microbe that has been modified by a CRISPR-Cas or Cpf1 system to add or delete a gene that enhances the health of a person's skin.

Other embodiments include a method of improving the health of a person's skin microbiome, comprising: providing a first type of bacteria to a person's skin that produces an agent that another second bacterial species requires for growth; after applying said first bacteria to the skin of a person, then applying the second bacteria to the person's skin, wherein both the first and the second bacteria comprise at least one microbe that has been modified by a CRISPR-Cas or Cpf1 system to add or delete a gene that enhances the health of a person's skin. In still others, the virulence factor of the first bacteria is modified via CRISPR-Cas to impede the interaction of bacterial adhesions and keratinocyte receptors. One can modify the expression of at least one gene by employing a CRISPR-Cas system to decrease the pathogenesis of a skin infection. Moreover, one can employ a second bacteria whose growth on a person's skin is enhanced by at least 2-fold when in the presence of the first bacteria, wherein the second bacteria is modified via CRISPR-Cas to have an essential growth required component deleted from its genome, and wherein the first bacteria has been modified via CRIPSR-Cas to add the same essential growth component that the second bacteria requires for growth.

Existing antibiotic therapies non-specifically kill the majority of skin-residing bacteria, disrupting the homeostasis of skin resident microflora. For example, benzoyl peroxide (BPO) is one of the most frequently used topical medications. BPO strongly suppresses the growth of *S. epidermidis*. *S. epidermidis* contributes to the skin resident microflora-based defense of the skin epithelium. The imbalance of microflora is believed by the present inventor to contribute to the pathogenesis of skin inflammatory diseases, such as atopic dermatitis, rosacea and acne vulgaris etc. Thus, in various embodiments, such antibiotic therapies are not employed but instead, beneficial bacteria are administered to a person's skin in a manner that beneficial results are achieved (e.g. reduction in malodors, generation of desired odors by bacterial production of scents, etc.) CRISPR-Cas systems are preferably employed to modify species of bacteria already found on an individual's skin such that the disturbance of the "normal" population of a particular person is not disturbed in a fashion that could lead to disease or discomfort.

Various embodiments include providing two or more bacteria species that are normally found on a person's skin, and modifying the same to remove virulence factors via CRISPR; including in such bacteria beneficial genes for the production of emollients, lipids, scents, etc. and using competitive inhibition to foster the growth of bacteria purposefully exposed to the skin surface so that pathogenic bacteria are not permitted to establish and grow. In certain embodiment, CRISPR is employed to insert a gene for the production of tomatidine in a bacteria such that, especially in the gut microbiome, but preferably also in the oral and skin microbiome, tomatidine is expressed. Tomatidine has the effect of increasing and enhancing muscle performance and in maintaining the weight, especially muscle mass, of an individual.

*Staphylococcus aureus* is the most pathogenic species of the *Staphylococcus* genus, responsible for food poisoning, suppurative localized infections and physical septicemia (graft, cardiac prostheses). Ogston (1881) coined the genus *Staphylococcus* to describe grapelike clusters of bacteria (staphylogrape, Gr.) recovered in pus from surgical abscesses. The species proves to be an opportunistic pathogen in certain locations or under certain circumstances and is found in the commensal flora (in 15% to 30% of healthy individuals in the nasal fossae). *S. aureus* has pathogenic capacities, in particular an invasive capacity, a capacity to multiply and to spread in the organism, and also a toxic capacity. *S. aureus* has a great capacity for developing antibiotic-resistant mutants. In one embodiment, modified *Staphylococcus epidermidis* is used to produce enhanced amounts of anti-microbial peptides that inhibit *S. aureus* biofilm formation, with preferred embodiments employing CRISPR-Cas systems to achieve such modifications.

In various embodiments, due to the inclusion of bacteria-hostile formulations in over-the-counter lotions and related products, the use of conventional lotions is not suggested for employment in conjunction with the administration of many embodiments of the present invention. Lotions presently available are believed to be counterproductive to the fostering the beneficial growth of beneficial bacteria on a person's skin. E.g. salicylic acid is bacteriostatic that limits the growth of bacteria by interfering with bacterial protein production by down regulating fitness and virulence factor production of bacteria. As it is known that gram positive and gram negative bacteria prefer slightly basic conditions pH 7.5 and warm temperatures 37 degrees Celsius (98.6 degrees Fahrenheit), the establishment and maintenance of slightly acidic conditions on one's skin is a preferred objective and is achieved by the fostering of certain bacteria that produce lactic acid on a person's skin.

All gram negative bacteria are disease producing. As such, one aspect of the present invention is directed to reducing the number of gram negative bacteria on a person's skin by adjusting the overall local pH of the skin tissue region by providing bacterial species that are selected to synergistically grow together and establish a desired pH level that discourages the growth of gram negative bacteria on the skin. Caution is called for, however, as the pH should not get too low, as fungi, yeast, and molds prefer acid conditions (pH 5.5-6) at room temperature to multiply. In this regard, the pH is preferably maintained, either by bacterial species producing lactic acid at amounts sufficient to achieve such levels, or by other pH adjustment methods, in order to hinder the growth and progression of pyogenic cocci, spherical bacteria that cause various suppurative (pus-producing) infections. Included are the Gram-positive cocci *Staphylococcus aureus*, *Streptococcus pyogenes* and *Streptococcus pneumoniae*, and the Gram-negative cocci, *Neisseria gonorrhoeae* and *N. meningitidis*. In terms of their phylogeny, physiology and genetics, these genera of bacteria are unrelated to one another. They share a common ecology, however, as parasites of humans. The Gram-positive cocci are the leading pathogens of humans. It is estimated that they produce at least a third of all the bacterial infections of humans, including strep throat, pneumonia, otitis media, meningitis, food poisoning, various skin diseases and severe types of septic shock. The Gram-negative cocci, notably the Neisseriae, cause gonorrhea and Meningococcal meningitis. Again, the reduction of virulence factors of such bacteria via CRISPR-Cas or Cpf1 systems reduces the incidence of infections caused by such bacteria and leads to methods and systems for establishing and maintaining a healthy skin microbiome, free of disease.

In yet other embodiments, bacteria are modified to express certain compounds that deter mosquitoes from alighting on an individual's skin. In certain embodiments bacteria are modified to produce amounts of DEET, with such bacteria being contacted to an individual's skin. In still other embodiments other known insect repellents such as eucalyptol, linalool, and thujone, are expressed by such bacteria to deter insects. In still other embodiments, bacteria are modified to express a protein member of the ionotropic receptor family, IR40a, which is a DEET receptor. In addition, other repellent proteins structurally related to DEET may be employed to repel insects, such as mosquitoes and flies.

One aspect of various embodiments is directed to the expression of particular phytochemicals by CRISPR-Cas modified bacteria to ameliorate a human disease. Phytochemicals exert their antibacterial activity through different mechanisms of action, such as damage to the bacterial membrane and suppression of virulence factors, including inhibition of the activity of enzymes and toxins, and bacterial biofilm formation. These antibacterial effects of phytochemicals may be due to the presence of one or more of alkaloids, sulfur-containing phytochemicals, terpenoids, and polyphenols and also may involve a synergistic effect when used in combination with conventional antibiotics, thus modifying antibiotic resistance.

Treatments for various types of cancer are desired that relate to the production of competently folded p53 tumor support factor. There has been a long felt but unmet need for a way to inexpensively administer desired amounts of p53 protein to an individual in need thereof. The present invention in several of its aspects addresses this concern, for example, by the expression of p53 by human microbiome bacteria. In certain embodiments of the present invention, a method for treating cancer cachexia involves the administering to the microbiome of a subject in need thereof an effective amount of a bacterial combination that expresses p53 protein and tomatidine, such cancer being for example, one of breast cancer, bladder cancer, kidney cancer, throat, oral, brain cancer, or colorectal cancer. In certain embodiments, the cancer is a metastatic cancer; and the microbiome is one or more of the gut microbiome, the oral microbiome (including the nasal microbiome) or the skin microbiome. Other embodiments involve mucosally administering to the subject an effective amount of a bacteria that has been modified to express a particular protein or drug or compound, especially those that are anti-cancer agents, such as one of tomatidine and p53, with the bacteria selected from the group consisting of—*Streptococcus, Actinomyces, Veillonella, Fusobacterium, Porphromonas, Prevotella, Treponema, Neisseria, Haemophilus*, Eubacteria, Lactobacterium, *Capnocytophaga, Eikenella, Leptotrichia, Peptostreptococcus, Staphylococcus, Streptococcus thermophilus* and *Propionibacterium*. Still other embodiments include the provision of *Streptomyces hygroscopicus* in an amount effective to produce therapeutically effective amounts of rapamycin to the subject. Providing the genes sufficient to make rapamycin and including them in a suitable microbe, preferably one of the bacteria listed herein, is one method for providing rapamycin to an individual in a manner such that the "bugs as drugs" administration can be achieved. One of ordinary skill in the art will appreciate how to select the genes responsible for the generation of rapamycin so as to achieve expression thereof in a fashion that does not kill the microbe being employed to manufacture therapeutically sufficient and desired amounts of rapamycin. The genetic sequence of the genes involved in the production of rapamycin by *Streptomyces hygroscopicus*.

Incorporated by reference herein are the following to address written description and enablement issues: US Pat. Publication No. 20190388471 to June; 20190000815 to Melin; 20180258100 to Gregory; 20170027914 to Qi; 20130310416 to Blagosklonny.

It should be appreciated that a therapeutically effective amount is preferably an amount sufficient to elicit any of the listed effects of natural tomatidine, rapamycin and/or p53, for example, including, but not limited to, the power to treat cancer cachexia in a fashion demonstrated by a result indicating the maintenance of muscle mass in the individual treated. In preferred embodiments, the mucosal administration is oral administration and the subject individual maintains or increases muscle mass. In most preferred embodiments, the bacterial composition has been modified via a CRISPR-Cas or CPf1 system to express a desired protein or compound, such as tomatidine, p53, rapamycin, etc., and in other embodiments, produces both tomatidine and p53 protein. Other embodiments include a bacterial composition that includes one of a *Chlamydia* species, or *Shigella flexneri, Mycoplasma bacteria*, and *H. pylori*.

In the 1920s, Dr Otto Warburg first suggested the significant difference in energy metabolism between malignant cancer cells and adjacent normal cells. Tumor cells mainly adopt the glycolysis as energy source to maintain tumor cell growth and biosynthesis under aerobic conditions. Investigation on energy metabolism pathway in cancer cells has aroused the interest of cancer researchers all around the world. In recent years, plentiful studies suggest that targeting the peculiar cancer energy metabolic pathways, including glycolysis, mitochondrial respiration, amino acid metabolism, and fatty acid oxidation may be an effective strategy to starve cancer cells by blocking essential nutrients. Natural products (NPs) are considered as the "treasure trove of small molecules drugs" and have played an extremely remarkable role in the discovery and development of anticancer drugs. And numerous NPs have been reported to act on cancer energy metabolism targets. Tomatidine is such a natural product whose employment in treating various cancers and related cancer cachexia is part of various aspects of the present invention.

Certain embodiments are directed to a method of treating bladder cancer in a subject in need of such treatment, such method comprising administering to a microbiome of a subject with bladder cancer an effective amount of a bacterial composition comprising *Bacillus* calmette-guerin, with the bacterial composition adapted to produce at least one of tomatidine, p53 and rapamycin. Preferably, the bacterial composition comprises bacteria modified via a clustered regularly interspaced short palindromic repeats (CRISPR) CRISPR associated protein (Cas) system to express one or both of tomatidine and rapamycin, and in other embodiments, also p53. Certain embodiments are focused on treating metastatic bladder cancer. The microbiome employed may be the gut, oral, bladder or skin microbiome. Certain embodiments further include employing a microbe selected from the group consisting of *Streptococcus, Actinomyces, Veillonella, Fusobacterium, Porphromonas, Prevotella, Treponema*, Nisseria, Haemophilis, Eubacteria, Lactobacterium, Capnocytophaga, Eikenella, Leptotrichia, *Peptostreptococcus, Staphylococcus*, and *Propionibacterium*. One preferred embodiment involves administering a bacterial composition to the subject so that at least 0.1 mg of rapamycin is provided to the subject each day. Preferably, the bacterial composition is modified via a CRISPR-Cas system to express one of rapamycin and/or tomatidine, with preferred bacterial compositions including one of a *Chlamydia, Shigella flexneri, Mycoplasma bacteria*, and *H. pylori*. In other preferred embodiments, the method comprises administering to a microbiome of a subject with bladder cancer an effective amount of a bacterial composition comprising a bacteria that has been modified to express a therapeutically effective amount of tomatidine and rapamycin, with the bacteria selected from the group consisting of *Streptococcus, Actinomyces, Veillonella, Fusobacterium, Porphromonas, Prevotella, Treponema*, Nisseria, Haemophilis, Eubacteria, Lactobacterium, *Capnocytophaga, Eikenella, Leptotrichia, Peptostreptococcus, Staphylococcus, Propionibacterium, Chlamydia, Shigella*

*flexneri, Mycoplasma bacteria, H. pylori*, and *Streptomyces hygroscopicus*. The bacteria employed may be of a species found in the subject's gut microbiome and may further have been modified using a CRISPR-Cas system to produce one of tomatidine or rapamycin. A therapeutically effective amount of a bacterial composition may also include *Streptomyces hygroscopicus* in an amount effective to provide a therapeutically effective amount of rapamycin to the subject. In particular embodiments, especially directed to addressing bladder cancer, the bacterial composition comprises *Bacillus* calmette-guerin, and even more preferably, where the *Bacillus* calmette-guerin also produces at least one of p53, rapamycin or tomatidine, and especially where the method maintains or increases the muscle mass of the subject. As described in more detail in the detailed description of various embodiments, still other agents, such as methylene blue, metformin, resveratrol (3,4',5-trihydroxystilbene; $C_{14}H_{12}O_3$), p53 protein, spermidine, diallyl trisulfide, apigenin, cyclopamine, sulforaphane, curcumin and glucosamine are employed via the production by microbes of an individual's microbiome to achieve the objective of delaying aging, and thus, in delaying and treating the onset of cancers.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. It is important, therefore, that the claims be regarded as including any such equivalent construction insofar as they do not depart from the spirit and scope of the present invention.

Checkpoint inhibition, namely PD1/PD-L1 pathway inhibition, has shown impressive results in many tumor types. One aspect of the present invention relates to the provision of checkpoint inhibitors in conjunction with bacterial formulations modified to express p53 and/or tomatidine. As the immune system is critically involved in the development, structural nature and progression of certain cancers, an inflammatory environment is believed to be related to tumor development. Chronic inflammation occurs due to tumor environment stress and the tumor microenvironment resembles an inflammation site, with metastatic sites creating a cytokine milieu conducive to tumor growth. In particular embodiments of the present invention, controlling cytokines is desired at particular sites of an individual's body, rather than systemic control of cytokines. Cytokines of the TNF family regulate a wide range of different immune defense mechanisms, both of the innate and the adaptive types. However, when acting in excess, they can cause significant damage. The ligands of the TNF family are cell-bound transmembrane proteins and thus exert their effects largely by affecting only cells that are located adjacently to the ligand-producing cell. Selective suppression of the ligand producing cells in situations where the ligand plays a pathogenic role forms one aspect of various embodiments of the present invention, such as where destruction of cells producing a cytokine may be preferable over mere attempts to achieve direct blocking of the function of the cytokine molecules. Destruction of cytokine-producing cells prevents further synthesis of the cytokines and provides durable protection. Blocking circulating cytokines affects the whole body. Destruction of cytokine-producing cells, in contrast, may be restricted to a particular site in the body while maintaining beneficial effects of the cytokine at other sites. Using the methods and systems as described herein, the direct and local administration of agents, such as p53, statins, tomatidine, rapamycin, etc. can be employed to achieve the desired non-systemic administration of such agents to tissues.

In some embodiments, methods further comprise administering to the subject an immune checkpoint inhibitor via cells within an individual's microbiome. Use of CRISPR-Cas systems to modify desired bacteria or other microbes to produce desired amounts of such inhibitors is thus one aspect of the preset invention. In some embodiments, the immune checkpoint inhibitor is a protein or polypeptide that specifically binds to an immune checkpoint protein. In some embodiments, the immune checkpoint protein is selected from the group consisting of CTLA4, PD-1, PD-L1, PD-L2, A2AR, B7-H3, B7-H4, BTLA, KIR, LAG3, TIM-3 or VISTA. In some embodiments, the polypeptide or protein is an antibody or antigen-binding fragment thereof. In some embodiments, the immune checkpoint inhibitor is an interfering nucleic acid molecule. In some embodiments, the interfering nucleic acid molecule is an siRNA molecule, an shRNA molecule or an antisense RNA molecule. In some embodiments, the immune checkpoint inhibitor is selected from the group consisting of nivolumab, pembrolizumab, pidilizumab, AMP-224, AMP-514, STI-A1110, TSR-042, RG-7446, BMS-936559, BMS-936558, MK-3475, CT O11, MPDL3280A, MEDI-4736, MSB-0020718C, AUR-012 and STI-A1010. In some embodiments, the immune checkpoint inhibitor is administered before the bacterial formulation. In some embodiments, the immune checkpoint inhibitor is administered at least one day before the bacterial formulation. In some embodiments, the immune checkpoint is administered at about the same time as the bacterial formulation. In some embodiments, the immune checkpoint inhibitor is administered on the same day as the bacterial formulation. In some embodiments, the immune checkpoint inhibitor is administered after the bacterial formulation. In some embodiments, the immune checkpoint inhibitor is administered at least one day after the bacterial formulation. In some embodiments, the immune checkpoint inhibitor is administered by injection. In some embodiments, the injection is an intravenous, intramuscular, intratumoral or subcutaneous injection.

Therefore, in some embodiments, the invention is directed to a system and method of treating cancer in a human subject comprising administering to the subject an immune checkpoint inhibitor via the expression thereof by an individual's microbiome, and includes, for example, expression using bacteria of the genera *Bifidobacterium*. Using CRISPR-Cas systems, one is able to achieve expression of genes and gene products in prokaryotic cells that provide desired amounts of checkpoint inhibitors to a person so as to effectively treat various forms of cancer. In such a manner, aspects of the present invention take advantage of the commensal relationship between the human host and the microbiome for the targeted delivery of nucleic acid therapies. In certain embodiments, employing the methods set forth herein one is able to deliver nucleic acids to program bacteria for expression of therapeutic proteins and RNA molecules in vivo at sites of greatest significance for a particular disease, thus providing for higher local concentrations of therapeutic products while reducing off-target effects.

One aspect of the present invention is the targeting of the gut microbiota-dependent trimethylamine-N-oxide (TMAO) formation as a therapeutic strategy to reduce thrombotic risk. One aspect of various embodiments is therefore to "drug the microbiome" for clinical purposes, including the maintenance of cardiovascular health. In one embodiment, choline analog inhibitors are selectively transported into gut microbes, thus limiting systemic drug exposure in the host. Choline accumulation is sensed as nutrient overload within gut microbes and promotes the induction of the cut gene cluster, encoding CutC/D itself as well as a choline transporter As a result, a positive feedback loop is established, whereby both the choline TMA lyase substrate (choline) and substrate analog (the drug inhibitor) are actively pumped and sequestered into the microbe. In turn, this event reduces choline availability to neighboring microbes, further contributing as a secondary mechanism to the reduction of TMA formation. The suppression of TMAO levels by choline TMA lyase inhibitors suppresses clot formation and provides for a potent antithrombotic effect of these compounds. Importantly, bleeding was not observed upon administration of the drugs, which represents a key and uncommon advantage for their as antiplatelet therapy. Modification of the gut microbiota composition to trigger a shift in the proportions of microbial communities such that an increase in the *Akkermansia* genus is observed that is believed to play a protective role in obesity and metabolic health. Thus, various aspects of the present invention include the shift of microbial composition to one that produces less TMAO and thus counteracts thrombotic risk, thus preventing or treating diseases through microbiome targeting Modulating the microbiome can be achieved in different ways, ranging from probiotics and prebiotics to fecal microbiome transplants, thus, the use of bacteria as drugs can be seen as an effective way to treat various diseases.

To comply with written description and enablement requirements, all references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material. Incorporated herein by this reference are the following US patent publications: 20170079947 to Richards; 20140296139 to Cohen et al.; 20160175327 to Adams et. al.; 20100081681 to Blagosklonny and 20120283269 to Blagosklonny; U.S. Patent Publication Nos. 20140030332 to Baron, et al., 20070123448 to Kaplan et al.; 20160000841 to Yamamoto, et al.; 20160095316 to Goodman et al.; 20160158294 to Von Maltzahn; 20140294915 to Kovarik; U.S. Pat. No. 8,034,601 to Boileau et al.; 20130225440 to Freidman, et al., 20150071957 to Kelly et al., 20160151428 to Bryann et al.; 20160199424 to Berry et al.; 20160069921 to Holmes, et al.; 20160000754 to Stamets; U.S. Pat. No. 9,044,420 to Dubensky, Jr, et al.; 20160120915 to Blaser et. al.; 2014/0349405 to Sontheimer; 2014/0377278 to Elinav; 2014/0045744 to Gordon; 2013/0259834 to Klaenhammer; 2013/0157876 to Lynch; 2012/0276143 to O'Mahony; 2015/0064138 to Lu; 2009/0205083 to Gupta et al.; 201/50132263 to Liu; and 2014/0068797 to Doudna; 2014/0255351 to Berstad et al.; 2015/0086581 to Li; PCT/US2014/036849 and WO 2013026000 to Bryann; U.S. Pat. Publication No. 2015/0190435 to Henn; 2012/0142548 to Corsi et al.; U.S. Pat. Nos. 6,287,610, 6,569,474, U.S. 2002/0009520, U.S. 2003/0206995, U.S. 2007/0054008; and U.S. Pat. No. 8,349,313 to Smith; U.S. Pat. No. 9,011,834 to McKenzie; 20150004130 to Faber et. al, 20160206666 to Falb; 20160206668 to Kort et al; and WO2015069682A2 to Asesvelt, et. al.; 20160199424 to Berry et al.; 20130326645 to Cost et al.; 2012/0276149 to Littman; U.S. Pat. No. 9,314,489 to Kelly et al.; U.S. Pat. Publication No. 2016/0024510 to Bikard et al.; U.S. Pat. Publication No. 2018/0015131 to Gajewski et al.; U.S. Pat. Publication No. 2018/0371405 to Barrangous et al. and U.S. Pat. Publication No. 2018/0140698 to Clube et al.

Other aspects of the present invention relate to the reduction of the likelihood of, treatment and/or prevention of cancer by interrupting a microbial carcinogenic pathway, and by enhancing an individual's survival. Various embodiments of the present invention use microbiota modifications to improve the efficacy of existing treatments, by modifying a patient's microbiome to address the treatment and prolonged survival of cancer victims.

Preferably, the modified bacteria employed in the present invention are administered orally to a patient in order to deliver the therapeutic directly to the site of inflammation in the gut. The advantage of this approach is that it avoids systemic administration of immunosuppressive drugs and delivers the therapeutic directly to the gastrointestinal tract. The viability and stability of such modified bacteria is enhanced to support the production of such microbes of desired agents, and by doing so, a method is provided that reduces gut inflammation, enhances gut barrier function, and/or treats autoimmune disorders. Preferably, such modified bacteria are capable of producing therapeutic anti-inflammation and/or gut barrier enhancer molecules, particularly in the presence of reactive nitrogen species, and more preferably the bacteria are functionally silent until they reach an environment containing local reactive nitrogen species (RNS), wherein expression of the therapeutic molecule is induced. In certain embodiments, the genetically engineered bacteria are non-pathogenic and may be introduced into the gut in order to reduce gut inflammation and/or enhance gut barrier function. For example, in some embodiments, the bacteria are under the control of a RNS-responsive regulatory region and a corresponding RNS-sensing transcription factor such that a desired product, e.g. butyrate is produced, which induces the differentiation of regulatory T cells in the gut and/or promotes the barrier function of colonic epithelial cells. Use of such modified bacteria, especially those modified via CRISPR-cas systems, provides a way to generate a desired therapeutic effect in a manner that lowers the safety issues associated with systemic exposure.

Various embodiments of the present invention are directed to the field of Oncology, and in particular, embodiments directed to a method of ameliorating, treating, or preventing a malignancy in a human subject wherein the steps of the method assist or boost the immune system in eradicating cancerous cells. In certain embodiments, the administration of beneficial bacteria to an individual's microbiome that have been modified so as to produce effective amounts of desired compositions, compounds, agents, etc, is done to address cancerous conditions. In several embodiments, the administration of such beneficial bacteria and microbes to an individual's microbiome invokes either an active (or a passive) immune response to destroy, weaken or render less invasive certain cancerous cells. Various other embodiments are drawn to the co-administration of biological adjuvants (e.g., interleukins, cytokines, *Bacillus* Comette-Guerin, monophosphoryl lipid A, etc.) in combination with conventional therapies for treating cancer. In particular, the co-administration of various pre-biotic compositions to enhance and sustain the desired effects of the beneficial modified bacteria forms another aspect of the present invention. In this regard, incorporation by reference of U.S. Patent publication No. 20160213702 to Maltzahn et al. is included as part of the written description of various aspects of the present invention. For example, in view of the fact that the microbiota of humans is complex and varies by individual depending on genetics, age, sex, stress, nutrition and diet, modifying the numbers and species of gut, oral, vaginal and skin microbiota can alter community function and interaction with the host. A number of probiotic bacteria known in the art, as well as some foods considered to be 'prebiotic' that contain substances that promote the growth of certain bacteria and that stimulate beneficial microbiota shifts to improve human health, can be employed in concert with the modified bacteria as described herein to effect desired cancer treatment regimens. For example, the administration of glycans in an amount effective to modulate the abundance of the bacterial taxa can be used to achieve better outcomes for cancer patients.

One application of the present invention is to provide a CRISPR-Cas modified bacteria, such as a lactobacteria, to a person diagnosed with cancer, so as to facilitate the production of agents in a manner that is effective to preserve muscle mass and function in such individual. Other embodiments include CRISPR-Cas modified bacteria that express levels of tumor suppressor factors, such as p53, in a manner that provides an effective, therapeutic amount to an individual via the production of such factors by one or more of the individual's microbiome (e.g. gut, oral, skin, vaginal, etc.) By having the individual's microbiome responsible for administration of such factors, instead of attempting to administer such factors via more traditional routes, such as injection, pills, etc., it is believed that a better result can be attained in a much more natural fashion.

Moreover, in view of the ability to further modify bacteria in various ways to provide desired factors at particular times, or in conjunction with particular agents, it is possible to fine tune the administration of desired factors, such as p53, so as to reduce any under or over production thereof. For example, rendering particular modified bacteria sensitive to a predetermined antibiotic can thus provide a way to reduce the numbers of any given modified bacteria in a manner to control the populations of such bacteria in an individual's microbiome, and hence, control the level of production of factors produced by such bacteria. To comply with written description and enablement requirements, incorporated herein by the following references are the following patent publications: U.S. Patent publication Nos. 20140349405 to Sontheimer; 20140377278 to Elinav; 20140045744 to Gordon; 20130259834 to Klaenhammer; 20130157876 to Lynch; 20120276143 to O'Mahony; 20150064138 to Lu; 20090205083 to Gupta et al.; 20150132263 to Liu; and 20140068797 to Doudna; 20140255351 to Berstad et al.; 20150086581 to Li; PCT/US2014/036849 and WO 2013026000 to Bryan; 20160199424 to Berry et al.; 20130326645 to Cost et al.

CRISPR-based genetic editing tools offer an efficient way to manipulate expression levels of multiple genes and to provide a solution towards the "multivariate modular metabolic engineering" to optimize the drug synthesis pathways with modular, multiplex regulation using only a few core proteins (e.g., dCas9) that are guided to specific sequences by guide RNAs.

In still other embodiments of the present invention, modifying bacteria so as to administer them to a person's microbiome is performed in a manner so that particular agents, factors or proteins derived from mushrooms, are rendered possible, with desired mushroom derived components believed to have anti-cancer characteristics, either alone or when used in conjunction with other agents. In particular, by assessing initially the particular bacterial constituents of an individual's microbiome and then administering to such individual a similar species of microbe, but one which has been modified, preferably via employment of a CRISPR-Cas system, one is able to effectively administer to such individual various desired anti-cancer treatments in a way that is believed to be far less disruptive, efficient and dependable as compared to other routes of administration. The modification of specially designed bacteria that reside in a person's body is believed to alleviate the concerns regarding genetic alteration of the human genome, as what is being modified is a microbiome that is present in a person's body—but is not directly involved in the human genome itself. There are a myriad of ways to combine various triggering factors to turn on or off particular productions of agents, factors or proteins that may be included in such modified microbiome species. The present invention in various embodiments is directed to at least those embodiments where cancer therapeutic agents can be administered by the microbiome of the individual that has cancer so as to effectively treat the cancer and/or remedy the symptoms resulting from the disease.

One aspect of the present invention is directed to the employment and modification of an individual's microbiome to address muscle mass retention and as a corollary thereof, to address the counterpart of obesity by lessening the amount of fat storage by such individual. In certain embodiments, the provision of effective amounts of tomatidine is rendered available to an individual. Still other embodiments also involve the reduction in the amount of acetate levels in an individual's body, which in turn lowers the amount of insulin the individual will produce, which has the effect of keeping fat cells from storing more energy in the form of fat. The reductions in the amount of acetate available in an individual's body further reduces the amount of the hormone ghrelin, thus reducing the hunger drive of the individual. Thus, the modification of an individual's microbiome influences various aspects of their metabolism in a manner that not only retains and maintains the ability to nurture muscle tissue, but to also reduce obesity by affecting the amount of fat that the body stores. While not bound by theory, it is believed that the gut bacteria of an individual is a substantial source of acetate production. The production of acetate by gut microbes is believed to send signals to the brain of the individual to initiate the production of insulin, conveyed via the vagus nerve. Fine tuning of the amount and type of gut microbes (e.g. via the use of antibiotics to initially reduce the kind and numbers of undesired bacteria, followed by purposeful inoculation of an individual's gut microbiome with modified microbes, e.g. via CRISPR-Cas insertion of particular factors, proteins, etc.) is an effective way to address not only muscle wasting issues, but also obesity issues of individuals.

While there are many gut bacteria that produce acetate, particular bacteria are preferably selected and even more preferably are modified using CRISPR-Cas systems to address the levels of acetate production once such bacteria are introduced to an individuals' microbiome. Preferably the gut microbiota are members of two bacterial divisions: the Bacteroidetes and the Firmicutes. The modification of an individual's gut microbiome is directed in a manner such that the typical increase seen in the relative abundance of the Firmicutes and a corresponding division-wide decrease in the relative abundance of the Bacteroidetes in obese individuals, is addressed. Obese people have more Firmicutes and almost 90% less Bacteroidetes than the lean people. Preferably, the administration of modified Bacteroidetes is achieved to more substantially reflect gut populations in more lean individuals, and by doing so, reducing the amount of acetate produced by the overall gut microbiome. Such a shift in the population of gut microbes to favor Bacteroidetes over Firmicutes, whether or not coupled with the administration of tomatidine, is one aspect of the present invention's objective of achieving a greater proportion of muscle mass than fat that would otherwise occur in any given individual. In still other embodiments, addressing the acetate production by especially Firmicutes, which has an increased capacity for fermenting polysaccharides relative to the lean-associated microbiome, is another way to achieve this objective, and addresses the significant obesity issues especially prevalent in Western societies.

In yet another embodiment, bioadhesive strips are provided that have encapsulated structures are filled with desired agents, including but not limited to tomatidine and/or microbes, especially bacteria that are found in an individual's oral microbiome, such that effective amounts of the agents can be administered to treat particular diseases including muscle atrophy. Preferably, the bacteria comprise bacteria that are found in the communities of healthy mouths, including, for example, *Streptococcus*, *Actinomyces*, *Veillonella*, *Fusobacterium*, *Porphromonas*, *Prevotella*, *Treponema*, *Neisseria*, *Haemophilus*, Eubacteria, Lactobacterium, *Capnocytophaga*, *Eikenella*, *Leptotrichia*, *Peptostreptococcus*, *Staphylococcus*, and *Propionibacterium*. Such strips may be manufactured to have desired dissolvable aspects thereto and that further have encapsulated portions that house desired agents, such as but not limited to tomatidine, p53 protein, and other agents able to treat cancer symptoms.

Some bacterial pathogens actively inhibit p53 protein and induce its degradation, resulting in alteration of cellular stress responses. For example, in gastric epithelial cells infected with *Helicobacter pylori*, a bacterial pathogen that commonly infects the human stomach, gastric cancer is more common. In addition to *H. pylori*, a number of other bacterial species also inhibit p53, providing further evidence that host-bacteria interactions reveal that bacterial infections are associated with tumorigenesis. Inhibition of p53 may provide certain benefits to bacteria, for example, it is believed that the inhibition of p53 may allow bacteria to subvert the host cell cycle control and apoptosis mechanisms, resulting in inhibition of cell death and survival of host cells damaged by infection.

In certain embodiments, CRISPR-Cas systems are employed to interfere with the p53 degradation abilities of particular bacteria that are known to degrade or otherwise interfere with the ability of p53 to function. As such in certain embodiments, the bacterial species is selected from the group consisting of a *Chlamydia* species, *Shigella flexneri*, *Mycoplasma* bacteria, and *H. pylori*.

The methods described herein are useful for treating and/or preventing (i.e., reducing the likelihood or risk of occurrence) different diseases, disorders, and conditions such as cancers and infectious diseases. Cancer remains the second most frequent cause of death in industrialized societies. Conventional therapies like surgery, radiotherapy, or chemotherapy remain the backbone of cancer therapy to date. Since the late 1980s, oncologists were successfully using the vaccine variant of *Mycobacterium bovis* BCG (Bacille Calmette-Guerin) as agent to prevent relapses of bladder cancer after surgical removal of the primary tumor. Although the exact mode of action of the bacteria is not fully understood, they might enhance the immune response against the cancer cells by, for example, activation of natural killer cells.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material. Incorporated herein by this reference are the following US patent publications: US Patent Publication Nos. 20140030332 to Baron, et al., and 20070123448 to Kaplan et al.; 20160000841 to Yamamoto, et al.; 20160095316 to Goodman et al.; 20160158294 to Von Maltzahn; 20140294915 to Kovarik; U.S. Pat. No. 8,034,601 to Boileau et al.; 20130225440 to Freidman, et al., 20150071957 to Kelly et al., 20160151428 to Bryann et al.; 20160199424 to Berry et al.; 20160069921 to Holmes, et al.; 20160000754 to Stamets; and U.S. Pat. No. 9,044,420 to Dubensky, Jr, et al.

While the provision of microbes, preferably bacteria, to a person suffering from cancer is via their gut microbiome, other microbiomes may be employed, e.g. other than the microbes that colonize the gastrointestinal (GI) tract, as there exist microbiomes on the skin, and in other epithelial and tissue niches such as the oral cavity, nasal passages, eye surface and vagina. Each of these microbiomes may be targeted for delivery of therapeutic agents to address cancer issues, including muscle atrophy associated with cancer. The gastrointestinal tract (as well as the other mentioned microbiomes) harbors an abundant and diverse microbial community, including diverse strains of bacteria. Hundreds of different species may form a commensal community in the GI tract in a healthy person, and this complement of organisms evolves from the time of birth to ultimately form a functionally mature microbial population. A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity.

In one embodiment of the present invention, a method and system and composition is provided to populate a person's microbiome, preferably their oral or gut microbiome, to restore, maintain or promote health of the individual and/or to alter a dysbiosis. For example, periodontal disease, a common chronic inflammatory disorder, has been associated with increased risk of postmenopausal breast cancer, particularly among former smokers who quit in the past 20 years. There is a need to design microbial compositions so that they possess a plurality of beneficial properties that would enhance the utility and commercialization of a microbial composition, especially those modified to produce desired agents, such as tomatidine. The human gut microbiota contains more than 500-1000 different phylotypes belonging essentially to two major bacterial divisions, the Bacteroidetes and the Firmicutes. The enhanced metabolic activities of the colonized gut ensure that otherwise indigestible dietary components are degraded with release of byproducts providing an important nutrient source for the host. Similarly, the immunological importance of the gut microbiota is well-recognized and is exemplified in germfree animals which have an impaired immune system that is functionally reconstituted following the introduction of commensal bacteria. T cell development and differentiation may require colonization by specific commensal microorganisms.

In yet further aspects of the present invention, the treatment of cancer and cancer cachexia can be addressed by administering to an individual a desired amount of a bacteria modified (preferably via CRISPR-Cas systems) to produce predetermined levels of tomatidine and/or p53 protein. Inclusion of DNA in microbes to produce certain p53 protein in a person's microbiome is one way in which to administer amounts to a person's body in a manner that can be tolerized to such amounts. Effective ways to ensure that the type, amount, and timing of desired administration is achieved is made possible by the ability to promptly address the survival of these modified microbiomes by use of antibiotics, or any number of other ways to either increase or decrease the efficiency of such modified microbes. Such a system and method addresses concerns with respect to proper timing of amounts that the person is being properly exposed to due to effective ways to control the administration of such factors, proteins, drugs, etc. via one's microbiome.

The particular protein degradation pathway which seems to be responsible for much of the muscle loss seen in a muscle undergoing atrophy is the ATP-dependent, ubiquitin/proteasome pathway. In this system, particular proteins are targeted for destruction by the ligation of at least four copies of a small peptide called ubiquitin onto a substrate protein. In skeletal muscle, the E3 ubiquitin ligases atrogin-1 and MuRF1 are known to play essential roles protein degradation and muscle atrophy.

The bone is a common site of metastasis for several malignancies. The impact of metastasized tumor cells in the bone disrupts the balance between the activities of the osteoclasts and osteoblasts. Radiographically, bone lesions are classified as being osteolytic (bone loss) or osteosclerotic (bone formation) or mixed.

Osteopontin is expressed by tumor cells and stimulates osteoblast differentiation. Osteopontin is a pro-inflammatory cytokine and is implicated in the progression of liver tumors, as well as other tumors. Tumor cells with a competent Hedgehog pathway are more potent at inducing osteoblast differentiation. The Hedgehog pathway plays an essential function in regulating cell fate and in developmental patterning in humans and is important in the formation of the skeleton. During skeletogenesis and endochondral ossification, Hedgehog pathway signaling coordinates growth and differentiation. Reactivation of the Hedgehog pathway has been implicated in a wide variety of cancers and carcinogenesis.

Tumor cells initially enhance the differentiation of osteoblasts that in turn, express osteoclastogenesis enhancing factors. Later, as the osteoblasts get eliminated, an environment is created that stimulates osteoclast differentiation and activity. Thus, an active Hedgehog pathway signaling in the tumor cells facilitates the generation of an osteoclast-stimulating milieu by initially kick starting osteoblast development. Tumor cells can alter the balance between the activities of osteoblasts and osteoclasts via Hedgehog pathway signaling. For example, breast cancer cells express Hedgehog pathway ligands and the Hedgehog pathway signaling propels breast cancer progression. Administration of pharmacological Hedgehog pathway inhibitors can inhibit Hedgehog pathway signaling in breast cancer cells and Hedgehog pathway proteins and genes have also been implicated in esophageal cancer, stomach cancer, prostate cancer, ovarian cancer, biliary tract cancer, glial cell cancer, multiple myeloma, colon cancer and melanoma. While not bound by theory, tomatidine is believed to interfere with the Hedgehog pathway and may inhibit the actions of the pro-inflammatory cytokine Osteopontin.

Hedgehog pathway signaling in the tumor cells is essential to the development of osteolytic metastases. Soluble factors, that include Osteopontin (OPN) and other Hedgehog pathway ligands, are secreted by tumor cells, and are thought to enhance osteoblast differentiation and mineralization activity. Tumor cells initiate osteoblast differentiation and the expression of osteoclastogenic factors is seen as an early event, followed by elimination of osteoblasts later. Thus, the overall microenvironment in cancer progression appears to shift in favor of osteoclastogenesis. An active Hedgehog pathway signaling and expression of OPN are important attributes for a tumor cell to activate osteoclast differentiation and resorptive activity.

Blocking the Hedgehog pathway interferes with the transcription of Osteopontin (OPN). Cyclopamine treatment decreases the activity of the OPN promoter in a dose-dependent manner. In contrast, tomatidine, the structural analog of cyclopamine, has apparently no effect on the promoter activity of cyclopamine. This is surprising but reveals that the particular mode of action of tomatidine in the body is as yet not fully known.

Tumors are now recognized as comprising of a mosaic of genetically different and actively mutating cells rather than a single type. Thus, combination drug therapies are being advocated to combat tumor cellular heterogenecity. Employing various methods of the present invention, it is believed that such combination therapies can be achieved by using an individual's own microbiomes, such that one or more drugs, factors, proteins, (e.g. tomatidine and p53) can be provided to an individual through the modification of the individual's microbiome.

In spite of great advances in understanding pathways related to cancer and cancer therapy, there is a need to provide new anticancer treatments that do not cause toxicity to healthy cells and that is effective in treating cancer, and especially the cachexia associated therewith. The present invention provides such a treatment option, and one that is in many ways, more subject to the inherent control aspects of the human body as it relies upon the long established but poorly understood relationship between diseases and the microbiomes of humans.

In still other embodiments of the present invention, embodiments relate to the employment of anti-muscle atrophy characteristics of tomatidine as described herein, but further involve the employment and production of anticancer proteins via the microbiome of an individual, e.g. that are capable of oral administration, and are preferably stable at room temperature, and in some embodiments also have potent antiviral activities that can be useful in a significant percentage of human cancers that are caused by viral infections. One aspect of the present invention is directed to the use of CRISPR-Cas systems to provide a better p53 protein that is much more stable so that its folding is preserved, thus protecting its tumor suppressing function. In particular, the regions where the protein are most vulnerable to mutations that cause improper folding are targeted and revised so as to impede such mis-folding events.

The microbiota inhabiting our bodies influence cancer predisposition and etiology. The largest microbial community in the human body resides in the gut and comprises somewhere between 300 and 1000 different microbial species. The human oral microbiome and the bacteria inhabiting such microbiome are, in certain circumstances, also effective as agents in the treatment of cancer. Various embodiments of the present invention involve the modification of at least two, if not three separate microbiomes of a person to treat certain conditions. For example, the treatment for cachexia may be achieved via modification of an individual's oral microbiome via the delivery of particular bacteria designed to produce therapeutic amounts of tomatidine. The simultaneous provision of bacteria to the individual's gut microbiome that are designed to produce therapeutic amounts of p53 protein can also be achieved, with the two separate microbiomes being employed to address separate but related issues involved in cancer treatments. This particular aspect of the present invention, while simple in nature, is believed to have profound effects in avoiding undesired drug interactions that can complicate treatment regimens. By having different microbiomes of the same individual administer different desired compounds, drugs, factors, proteins, etc. to the person's body, the ability to separately control administration and amounts (as well as to address issues by killing bacteria in one but not the other microbiome) is rendered feasible as a way to administer desired cancer fighting agents to an individual.

Still other aspects of the present invention are directed to the use of antibodies against certain oral bacteria, e.g. *P. gingivalis*—which is a pathogen known to contribute to periodontal disease and that has been associated with the risk of pancreatic cancer, and lung cancer, colorectal cancer and cancers of the stomach, oesophagus, and cancers of the head and neck. Microbes mediate the relationships with these types of cancer and epidemiologic evidence exists that shows the association between the human microbiome and these types of cancer. Particular embodiments relate to an association of the oral microbiome and periodontitis with pancreatic cancer, with a strong positive association being noted between periodontitis at baseline and subsequent risk of fatal pancreatic cancer. Men with periodontal disease have a 64% higher risk of pancreatic cancer compared to those reporting no periodontal disease and have a 4-fold increase in risk of pancreatic cancer. Elevated antibodies to *P. gingivalis* have been associated with a 3-fold increase risk of aerodigestive cancer mortality.

One aspect of the present invention is directed to the use of commensal and symbiotic microbiota that have tumor-suppressive properties. It is believed by the present inventors that the associations between diet and cancer risk is explained by differences in microbiota among the participants and that the employment of probiotics and prebiotics is an effective chemoprevention strategy that can be utilized to promote health and cancer treatment and recovery. Enhancing the microbiota of an individual with particular microbes, such as those modified by CRISPR-Cas systems, to include, for example, the provision of one of p53 protein expression or tomatidine expression, is one of the aspects of various embodiments of the present invention.

While cancer has been largely perceived as an intrinsic problem of body homeostasis, and infection a problem of external environment, the present inventors believe that the effective treatment of both diseases converges in that premalignant cell behavior is a mirror of cellular dysbyosis. Infection, like cancer, is a lack of regulation of important cells of the superorganism of the human body in concert with its integral microbiomes. There appears to be a strong association between the human microenvironment, sustained inflammation, and cancer. Growing evidence has emerged that, for example, the oral microbiome and periodontitis has a profound impact with respect to the pathogenesis and risk of various malignancies.

One aspect of the present invention relates to a paradigm shift from the classic germ theory so prevalent in western medicine during the last century. Viewing the microbiome of a person as an integral part of the human person in terms of health, much as an organ of such individual, is a more correct and useful concept as it relates to understanding cancer and in treating the same. Just as methods for addressing microbe based diseases has advanced recently, the ability to address cancer treatments from a new perspective is critical in advancing effective treatments to avoid if not cure various cancers. There are parallels between infection by microbes and cancer from various perspectives. For example, a single infection can arise from a single microbe, just like a cancer can be initiated by a single cell, and then spread to establish tumors and metastatic disease. In both cases, disruption of homeostasis allows for pathological bacterial expansion and may lead to full blown infection. But not all pathologic microbes lead inevitably to infection, as such a course is arrested by immune system responses. Similarly, precancerous cells and tissues do not always progress to full blown cancer, but rather, the progression of cancer is hindered or halted by the immune system. Premalignant cell behavior is a virtual mirror to microbial dysbiosis. Cancer, like infection, can be viewed as a dysbiosis of a person's microbiome.

Despite the success of colonoscopy screening, colorectal cancer remains one of the most common and deadly cancers, and colorectal cancer incidence is rising in some countries where screening is not routine and populations have recently switched from traditional diets to western diets. Colorectal cancer represents an important disease as one of the major causes of death worldwide.

More than 50,000 people are diagnosed with pancreatic cancer every year, and because the disease is often not diagnosed until an advanced stage, less than 10% of those diagnosed will still be alive in five years. People with two types of periodontal disease have a greater risk of subsequently developing pancreatic cancer, showing that markers of pancreatic cancer can be found in oral microbiome dysbyosis. Oral bacteria is the underlying explanation due to periodontitis being caused by oral bacteria dysbiosis. For example, individuals who have *Porphyromonas gingivalis* in their oral microbiome have an almost 60% greater risk of developing pancreatic cancer relative to those who do not have such bacteria in their oral microbiome. Similarly, individuals with *Aggregatibacter actinomycetemcomitans* present in their oral microbiome have at least a 50% increased relative risk of developing pancreatic cancer. Thus one aspect of the present invention is directed to the establishment of and maintenance of an oral microbiome of an individual such that there are less robust populations of at least one of *Porphyromonas gingivalis* and *Aggregatibacter actinomycetemcomitans* in a person's oral microbiome. One of the major challenges to detecting pancreatic cancer is its late clinical presentation. By the time pancreatic cancer is diagnosed, the cancer is usually well-advanced. Pancreatic adenocarcinoma is a low-incident but highly mortal disease. It accounts for only 3% of estimated new cancer cases each year but is currently the fourth common cause of cancer mortality. By 2030, it is expected to be the 2.sup.nd leading cause of cancer death.

In one aspect of the present invention, a method includes the bacterial analysis of an individual's stool in a non-invasive way for screening for pancreatic cancer. Preferably, a non-invasive, stool-based screening tool for colorectal cancer is employed and a kit is used such that patients can use and send the kit in via mail for evaluation.

Throughout evolution, bacteria progressively acquired virulence factors and the disease-promoting and pro-carcinogenic effects of pathogens depend on these virulence factors, which often comprise adhesion molecules, which confer the ability to adhere to and invade the tissues of the human body. One aspect of the present invention is directed to the modification of such adhesion molecules so that pathogenic bacteria are altered in a manner that reduces their abilities to adhere to tissues of the human body, thus lessening various human diseases.

Chronic and/or excessive consumption of alcohol has been found to be an important risk factor for many cancers, including colorectal cancer. Microbial metabolism may contribute to the toxicity of alcohol, especially in the gastrointestinal tract, where aerobic and facultative anaerobic bacteria convert ethanol to acetaldehyde. Indeed, acetaldehyde is known to be a highly toxic and pro-carcinogenic compound with various negative effects, ranging from DNA damage and impaired DNA excision repair to the degradation of folate. Thus one aspect of various embodiments of the present invention is directed to providing particular bacteria to a person who consumes alcohol in a manner that lessens the risk of cancer via the ability of such bacteria to ameliorate the accumulation of acetaldehyde. The conversion of ethanol to acetaldehyde is inhibited by the use of antibiotics, such as ciprofloxacin, which kills primarily aerobic and facultative anaerobic bacterial populations. Thus, to reduce the undesired effects of alcohol conversion to acetaldehyde, the use of specific antibiotics, followed by the use of probiotics and/or fecal transplantation protocols, is one aspect of the present invention that may be employed to combat colorectal cancer-associated dysbiosis and thus restore eubiosis in chronic diseases, helping to reduce microbiota-induced genotoxicity and activation of inflammatory, proliferative and pro-carcinogenic pathways. The gut microbiota plays a major role in the promotion and progression of colorectal cancer via several mechanisms, including inflammation, metabolism and genotoxicity, and thus, targeting an individual's microbiota is an effective way to treat, if not prevent, colorectal cancer. Particular bacterial species have been identified that are suspected to play a role in colorectal carcinogenesis, including *Streptococcus bovis, Helicobacter pylori, Bacteroides fragilis, Enterococcus faecalis, Clostridium septicum, Fusobacterium* spp. and *Escherichia coli*. Cancer incidence is low in the Ohio Amish and it is believed by the present inventors that the presence of *Prevotella* bacteria as more predominant bacteria in both their oral and gut microbiomes, is related to such lower cancer incidence. The gut microbiota of various livestock species has been reported to contain a high relative abundance of the xylanolytic bacterial species *Prevotella*. The present inventors submit that the environment plays an important role in modulating bacterial community composition and that transmission of gut microbes occurs across host species. Gut microbial communities often contain many *Bacteroides* or their close relatives, *Prevotella*. One aspect of certain embodiments of the present invention is directed to increasing the prevalence of *Prevotella* populations in individuals so as to lessen the chances of cancer developing in such individuals. Still other embodiments are directed to the modification of *Prevotella* bacteria in a manner that makes them less virulent, but that still maintain the beneficial effects of such bacteria in various microbiomes, such as the oral and gut microbiomes, e.g. by reducing the expression of virulence factors of *Prevotella*.

Another aspect of the present invention is directed to expression of particular tumor suppression agents by microbes in an individual's microbiome. Among tumor suppressor agents, the p53 protein is a transcription factor that recognizes and binds to specific DNA response elements and activates gene transcription. P53 is a tumor suppressor that has a role in the maintenance of genomic integrity and as a guardian of DNA. p53 secretion and uptake by cells demonstrates that p53 is a transmissible particle. Stress triggered by ionizing radiation or other mutagenic events leads to p53 phosphorylation and cell-cycle arrest, senescence, or programmed cell death. Tumor suppressors are complex macromolecules normally occurring as multi-domain proteins flanked by disordered segments. The tumor-suppressor p53 is a transcriptional factor that exerts broad anti-proliferative effects, including growth arrest, apoptosis, and cell senescence after cellular stress, and has been described as the most frequently mutated gene in cancer cell. The end regions of tumor suppressor p53 act as molecular antennas for proper activity and interactome signaling. Although classified as a transcription factor, p53 can also mediate apoptosis.

Most human viruses impair p53 activity. For example, in cervical cancer, the human papillomavirus E6 protein targets p53 for degradation. Bacterial infection is known to trigger the p53 pathway and activates p53 isoforms. Another aspect of the present invention is directed to the involvement of p53 aggregates in cancer pathogenesis and progression. The production of competent p53 by bacteria in a person's microbiome is a better way in which to provide sufficient amounts of p53 to suppress tumorgenesis. Thus, one aspect of the present invention relates to the use of CRISPR-Cas to modify bacteria to express p53 proteins, and preferably a more stable p53 protein in that its folding is preserved, thus protecting its tumor suppressing function. The regions where the protein are most vulnerable to mutations that cause improper folding are targeted and revised so as to impede common mis-folding events.

In yet other embodiments, cancer cells are infected with modified bacteria having thermosensors, thus making such cancer cells amenable to some controls incorporated therein, such as by adjusting the temperature to turn on certain genes—with such genes encoding toxins. Alternatively, one is able to shut off the genes by adjusting the temperature, thus selectively killing or modifying the behavior of the cells infected by the bacteria.

The prokaryotic type II CRISPR-Cas9 (clustered regularly interspaced short palindromic repeats-CRISPR-associated 9) system is rapidly revolutionizing the field of genetic engineering, allowing researchers to alter the genomes of a large range of organisms with relative ease. Experimental approaches based on this versatile technology have the potential to transform the field of cancer genetics.

Yet another aspect of the present invention relates to an increased risk of pancreatic cancer in patients with *Helicobacter pylori* (*H. pylori*) and that is also dependent on particular blood types with an association between pancreatic cancer risk and CagA-negative *H. pylori* seropositivity found among individuals with non-O blood type, but not among those with O blood type. The differences in terminal binding antigens in gastrointestinal mucins for individuals with non-O blood type (A and B), influences the binding potential of the *H. pylori*. There is therefore a link between oral disease and pancreatic cancer and the bacteria found in certain types of gum disease is linked to a 2.times. greater risk of developing pancreatic cancer. Pancreatic cancer, which is difficult to detect and kills most patients within six months of diagnosis, is responsible for 40,000 deaths a year in the United States. Antibodies for oral bacteria are indicators of pancreatic cancer risk.

MicroRNAs (miRNAs) are short, noncoding RNAs that regulate target mRNAs via transcript degradation or translational repression. Cell- and tissue-specific miRNA expression profiles are altered in numerous disease states. Inflammatory bowel diseases (IBD) are a major risk factor for the development of colon cancer. The loss of all of the intestinal miRNA results in impaired barrier function and inflammation similar to IBD. Circulating miRNA profiles are known to correlate with miRNA expression changes in diseased tissue. While conventional efforts to treat cancer have focused on the inhibition/destruction of tumor cells, strategies to modulate the host microbiota and miRNAs-induced inflammation offer a new way by which to combat what has been a terribly difficult disease to address. Antibiotic treatment causes disturbance of the microbiota, and probiotics, prebiotics and fecal microbiome transplantation may be employed to restore the dysbiosis caused thereby. An individual's microbiota is tied into certain cancers, including colorectal cancer, by induction of a chronic inflammatory state, leading to the production of toxic metabolites. Microorganisms frequently found in IBD patients include different species that are well known butyrate producing bacteria, which are linked to disease severity. Thus, one aspect of the present invention relates to the modification of an individual's microbiota to reduce the amount of butyrate producing bacteria, or at least the amount of butyrate by the bacteria present in an individual's microbiota, especially their gut microbiome.

Molecular mechanisms modulated by gut microbiota promote inflammation and support colorectal carcinogenesis. Both endogenous and exogenous miRNAs modulate tumor-related inflammation in colorectal cancer. Gut microbiota has an influence on colorectal carcinogenesis and the microbe population living in the human intestine plays a significant role in the development and progression of colorectal cancer. Maintenance of a healthy intestinal epithelia is critical to provide optimal nutrient absorption, as well as an efficient immune barrier. The balance between intestinal microbiota, intestinal epithelium and host immune system is decisive for normal functionality of the intestinal cells. Therefore, changes in any of these three factors may influence the functionality of the intestinal epithelium. The benefits of the body in relation to gut microbiota are related to extraction of the energy from the fermentation of undigested carbohydrates and from the absorption of short-chain fatty acids. Butyrate is the most important of these fatty acids being metabolized by the colonic epithelium and is the favorite energy source of colonocytes. The most important bacteria producing this fatty acid are *Faecalibacterium prausnitzii*, which belongs to the *Clostridium leptum* cluster, and *Eubacterium rectale/Roseburia* spp., which belong to the *Clostridium coccoides*. In healthy colonocytes, butyrate hampers apoptosis and further mucosal atrophy. In colorectal cancer cells, butyrate has been proved to stimulate differentiation, impede cell proliferation, lead to apoptosis and inhibit angiogenesis.

Butyrate protects human colon cells from DNA damage. In addition to butyrate, gut microbiota are also implicated in the constitution of another category of beneficial fatty acids, such as conjugated linoleic acids, having anti-inflammatory and cancer protective properties.

The composition of gut microbiota evolves throughout human life, from birth to old age, and is modulated, temporarily or permanently, by many factors such as dietary components, environment, age, stress, treatment (medical or surgical) and disease. Antibiotic-based therapy represents one of the most important factors with the effect on the composition of the microbiota. This therapy can cause diarrhea which generally is associated with altered intestinal microbiota resulting in enteropathogens overgrowth, loss of mucosal integrity and altered metabolism of vitamins and minerals. The elderly have significantly different microbiota than younger adults.

Individuals can be classified into one of three prevalent variants or "enterotypes" according to the abundance of predominant genera which are *Bacteroides, Prevotella* and *Ruminococcus*. *Bacteroides* enterotypes are related to amino acids, animal proteins and saturated fats, constituents typical to Western diet, while *Prevotella* is connected to carbohydrates and simple sugars, suggesting an interconnection with a carbohydrate-based diet more common of rural societies.

Individuals whose microbiota are mainly *Bacteroides* and commute their dietary patterns to a diet based on high proportions of carbohydrates, will acquire a *Prevotella* enterotype in the long term. Substantial changes in the composition of fecal microbiota are detectable in a few days after carbohydrate intake, demonstrating that diet rapidly and reproducibly alters the human gut microbiome. Numerous studies indicate that fruit, vegetable and a high-fiber intake, particularly of cereals and whole grains, is associated with a decreased risk of colorectal cancer, while diets that are rich in red and processed meat, fat and alcohol are associated with an increased risk of the disease. Higher dietary intakes of animal products may modify gut microbiota and consequently play an important role in carcinogenesis.

One aspect of the present invention is the modification of an individual's gut microbiome such that they harbor far less of the bacteria *Streptococcus bovis, S. bovis* bacteremia, Clostridia, *Bacteroides* and *Helicobacter pylori*, all of which have been involved in the pathogenesis of cancer.

Conversely, bacteria like *Lactobacillus* and *Bifidobacterium* have anticarcinogenic effects, which are believed to involve inactivation of microbial enzymes which are important for pro-carcinogen activation. *L. casei* and *L. acidophilus* decrease the activity of .beta.-glucuronidase, azoreductase, and reflect that the balance of activation and detoxification supports the belief that the microbial community structure plays a significant role in the initiating step of carcinogenesis. One aspect of the present invention relates to the favorable modulation of the gut microbiota structure to reduce the risk of cancer development e.g. by the clinical use of probiotic in the prevention of cancer. In various embodiments, the probiotic supplementation of an individual's microbiome is able to modify microbiota structure by reducing enterobacteria like *Salmonella/Shigella* and increasing lactic acid bacteria and Bifidobacteria to provide a protective role of such probiotics.

Inflammatory bowel diseases (IBD) are induced and preserved by diverse microorganisms and frequently involves signs of global dysbiosis, according to changes in the number, diversity and stability of microbiota. Increasing evidence shows that dysbiosis induces the production of genotoxins and metabolites associated with tumorigenesis and produces disorder of the immune response which promotes and maintains inflammation in IBD leading to colorectal cancer. Microorganisms frequently found in IBD patients include different species of *E. coli*, species of *Chlamydia, Mycobacterium, Clostridia, Candida*, as well as *Proteus mirabilis, Klebsiella pneumonia* and diverse Proteobateria, including *Helicobacter*. Firmicutes and Bacteroidetes decrease in IBD. Different bacterial species contribute to the pathogenesis of IBD, with enhanced activation of transcription factor NF-.kappa.B, an important regulator of inflammatory processes. NF-.kappa.B suppression improves IBD development, and NF-.kappa.B dependent cytokines are key agents which signal from inflammatory cells to tumor cells. In chronic inflammation, proinflammatory cytokines, such as TNF-.alpha., can induce DNA damage through reactive oxygen species (ROS) and nitrogen species, which leads to tumor initiation. TGF-.beta. is a powerful pleiotropic cytokine with immune suppressing and anti-inflammatory properties, inhibiting cell cycle progression and promoting apoptosis. Inflammatory bowel diseases (IBD) are a major risk factor for the development of colon cancer, by a mechanism called in literature colitis-associated cancer (CAC). The increased prevalence of CAC in IBD patients is influenced by disease severity and duration, and by the efficacy of anti-inflammatory therapies It seems that IBD are induced and preserved by various microorganisms and frequently involves signs of global dysbiosis, according to changes in the number, diversity and stability of microbiota. Increasing evidence shows that dysbiosis induces the production of genotoxins and metabolites associated with tumorigenesis and produces disorder of the immune response which promotes and maintains inflammation in IBD leading to cancer.

Potassium diazoacetate, a stable form of nitrosated glycine, has been found to initiate mutations in the p53 gene, supporting the hypotheses that NOC linked to glycine subscribes to p53 mutations in humans. High levels of polyamines are toxic and are associated with several diseases, including cancer, and oxidative stress that results from polyamine catabolism is the underlying mechanism of toxicity. Several pathogens, including *Shigella flexneri, Streptococcus pneumoniae, Salmonella enterica* and *H. pylori*, utilize polyamines to increase their virulence. One aspect of the present invention is to reduce the virulence of various bacteria found in a person's microbiota by employing CRISPR-Cas systems (or similar systems) to modify, if not remove the virulence abilities of various microbes to produce virulence factors.

Chronic inflammation can deeply alter local immune response and cause the liberation of nitric oxide. ROS can be produced by the gut microbiota or generated by immune cells during inflammation. Gastrointestinal bacteria generate nitric oxide from nitrate and nitrite. ROS are potent mutagens that lead to DNA breaks, point mutations, and protein-DNA crosslinking and influence chromosomal instability and the risk of cancer.

MicroRNA (miRNAs) are small (21-25 nucleotide) non-coding RNAs (ncRNAs) that regulate the translation and stability of their specific mRNA targets. The aberrant expression of microRNAs is related to the initiation and progression of various cancers, with MiRNAs acting as tumor suppressors or oncogenes. Inflammation determines changes in expression of miRNAs, primarily through the actions of proinflammatory cytokines. The role of miRNAs is believed to be in the initiation and progression of human cancer, as well as in involvement with immune responses, inflammation, cell proliferation and cell death, all of which are known to be regulated by NF.kappa.B. The overexpression of certain miRNAs is believed to lead to the repression of tumor suppressor genes that promote tumor survival and cell migration through NF-.kappa.B activation. While the gut microbiota interacts directly with the host through the production of metabolites, peptides and other molecules, how microbiota regulates miRNA expression and contributes to the maintenance of intestinal homeostasis and to IBD pathogenesis is still largely unknown. miRNAs play a role in colonic carcinogenesis and their reduction by butyrate is an important mechanism of its anti-cancer effects.

p53 is altered in many tumors. Various treatment strategies have focused on targeting p53. About 50% of human tumors have TP53 gene mutations. Because formation of a tetrameric structure is critical for protein-protein interactions, DNA binding, and the post-translational modification of p53, a small destabilization of the tetrameric structure results in dysfunction of tumor suppressor activity.

p53 tumor suppression protein is sometimes called "the guardian of the genome" as it is a key component of the cellular mechanisms controlling cellular responses to various cellular stresses. p53 is activated and primarily functions as a transcriptional regulator of expression of multiple effector proteins and miRNAs, which, in turn, regulate key cellular processes such as apoptosis, cellular proliferation, and autophagy. Since regulation of cellular stress responses is tightly intertwined with metabolic regulation, there is an interplay between p53 and multiple pathways involved in regulation of metabolism and cellular homeostasis that is complex and not fully understood. Approximately 50% of all human cancers have mutant p53, with approximately 75% of such cancers having a single amino acid residue missense mutation in the DNA-binding core domain. The p53 protein recognizes and binds to specific DNA response elements and activates gene transcription. The p53 gene is the most frequently mutated gene in cancer and is a transcriptional factor that exerts broad anti-proliferative effects, including growth arrest, apoptosis, and cell senescence.

Certain embodiments of the present invention are directed to a method that restores p53 via its expression by an individual's microbiome, such that tumors can be treated. Such methods involve a step of exposing cancer cells to bacteria that produce p53 proteins. p53 tumor suppressor has been identified as a protein interacting with the large T antigen produced by simian vacuolating virus 40 (SV40) Inhibition of p53 can be achieved by bacterial pathogens which actively inhibit p53 protein and induce its degradation, resulting in alteration of cellular stress responses. This phenomenon was initially characterized in gastric epithelial cells infected with *Helicobacter pylori*, a bacterial pathogen that commonly infects the human stomach and is strongly linked to gastric cancer. Besides *H. pylori*, a number of other bacterial species inhibit p53.

Various embodiments of the present invention are directed towards the direct interplay between bacterial pathogens and tumor suppression mechanisms that protect an individual from cancer development. Various pathogenic bacteria actively inhibit the major tumor suppression pathway mediated by p53 protein that plays a key role in the regulation of multiple cellular stress responses and prevention of cancerogenesis. Bacterial degradation of p53 was first discovered in the context of *Helicobacter pylori* infection, which is currently the strongest known risk factor for adenocarcinoma of the stomach. This phenomenon, however, is not limited to *H. pylori*, and many other bacterial pathogens inhibit p53 using various mechanisms. Inhibition of p53 by bacteria is linked to bacterial modulation of the host cellular responses to DNA damage, metabolic stress, and, potentially, other stressors.

Inactivation of p53 is a hallmark of tumorigenic changes. More than half of all tumors carry p53 mutations, rendering the p53 gene (tp53) the most mutated gene in human tumors. p53 can also be inhibited by mutation-independent mechanisms Inhibition of wild-type p53 by the SV40 virus was one of the first reported examples.

One aspect of the present invention is directed to bacterial inhibition of p53. Recent studies have found that it is not only viruses, but also some pathogenic bacteria, that actively inhibit p53 and induce its degradation. This phenomenon was initially described in gastric cells co-cultured with *Helicobacter pylori*. *H. pylori* is a gram-negative, spiral-shaped pathogen that lives in the stomachs of approximately half of the world's population. The infection is typically acquired during childhood and causes lifelong chronic infection. Because of the association between *H. pylori* infection and the incidence of gastric cancer, the International Agency for Research on Cancer (IARC) has classified this bacterium as a Group 1 carcinogen. *H. pylori* infection is considered to be the strongest known risk factor for gastric cancer, and epidemiological studies have estimated that, in the absence of *H. pylori*, 75% of gastric cancers would not occur.

*H. pylori* is able to dampen activity of p53 protein by inducing its rapid degradation. One particular aspect of certain embodiments of the present invention is directed to modifying *H. pylori*, preferably via use of a CRISPR-Cas system, such that its abilities to degrade p53 are reduced. The supplantation of such modified *H. pylori*, preferably just after a round of antibiotic treatment to reduce the numbers of native resident *H. pylori* in an individual's body, is done to then provide a competitive advantage of such modified bacteria and thus, will result in the reduction of p53 degradation, assisting in the treatment of the cancerous condition of the individual. Older people with gastric precancerous lesions, who are infected with *H. pylori*, may be particularly vulnerable to degradation of p53. *H. pylori* inhibits p53 through multiple mechanisms, implying that inhibition of p53 activity is an important factor for successful infection. The bacteria not only induce degradation of p53, but also alter the expression profile of p53 isoforms. Other bacteria induce degradation of p53 using a similar mechanism to that of *H. pylori*. As such, the method as set forth herein can be employed with other bacteria, as one of skill in the art will appreciate. For example, the intracellular bacterial pathogen *Chlamydia trachomatis* as well as other *Chlamydia* species, induce degradation of p53 by activating HDM2 protein. Degradation of p53 by *Chlamydia* contributes to cancerogenesis in the female genital tract and inhibition of p53 through the HDM2-dependent mechanism is employed by enteropathogen *Shigella flexneri*, which causes bacillary dysentery in humans. Certain bacteria can inhibit transcription of the p53 gene. Such inhibition of p53 may provide certain benefits to bacteria, such as allowing bacteria to subvert the host cell cycle control and apoptosis mechanisms, resulting in inhibition of cell death and survival of host cells damaged by infection. In the case of *H. pylori*, expression of the CagA virulence factor is sufficient to inhibit p53 and extend short and long term survival of gastric epithelial cells that underwent DNA damage. Thus, one embodiment of the preset invention is directed to the modification of *H. pylori* to remove or reduce the efficacy of the CagA virulence factor such that an individual pretreated with antibiotics to reduce resident *H. pylori*, followed by administration of *H. pylori* to such an individual where modifications to such modified strain has been made (e.g. via CRISPR tools) results in a better treatment method for particular types of cancer. The p53 pathway is known to affect immune response. Among direct transcription targets of p53 are a number of proteins regulating innate immunity and cytokine and chemokine production. p53 is also known to affect NF-.kappa.B activity and pro-inflammatory signaling.

One aspect of certain embodiments of the present invention is directed to the role of immunomodulatory function involved in the bacterial inhibition of p53. Some bacteria have evolved to inhibit p53 and do so via multiple mechanisms, including protein degradation, transcriptional inhibition, and post-translational modifications. p53 inhibition affects the host immune response, permitting bacteria to thrive and establish themselves. p53 has a role in controlling the bacterial infections and the inhibition of p53 confers certain selective advantages to bacteria but causes an increase in the risk of tumor development, especially when there exist conditions of prolonged chronic infections.

Numerous bacterial pathogens have also been shown to inactivate the major tumor suppressor p53 during infection. Such inactivation impedes the protective response of the host cell and affects the downregulation of host cell metabolism to interfere with intracellular bacterial replication, highlighting the crucial role of p53 in host—pathogen interactions.

Yet other aspects of the present invention are directed to the links between poor oral health and periodontal disease with an increased risk for cancers. The present inventors believe that periodontal disease contributes to the development of systemic inflammation and if left untreated, a chronic, smoldering inflammatory response occurs in response to periodontal microbial pathogens and their products, such as endotoxin. Infection will ultimately stimulate the production of pro-inflammatory cytokines and mediators such as IL-1.beta., IL-6, TNF-.alpha. and MMPs. IL-6, in particular, has tumor-inducing actions, by promoting growth and proliferation, in both healthy and malignant cells. IL-1 promotes tumor growth and metastasis by inducing matrix metalloproteinase activity and other growth factors.

Intestinal bacteria are implicated in several types of cancer. *Helicobacter* species have been associated with enhanced carcinogenesis including liver cancer, colon cancer, and mammary carcinoma. Many human viruses are known to impair p53 activity. In cervical cancer, the human papillomavirus E6 protein targets p53 for degradation. Bacterial infection has been shown to trigger the p53 pathway and to activate p53 isoforms. Resveratrol has been shown to inhibit carcinogenesis through the induction of p53-dependent cell death.

In one aspect of the present invention, using CRISPR-Cas, a more stable p53 protein is constructed in terms of the stability of its folding being preserved, thus protecting its tumor suppressing function. According to the present invention, the regions where the p53 protein are most vulnerable to mutations that cause improper folding are therefore targeted and revised so as to impede common mis-folding events. Using such an improved, stable form of p53, and having it expressed in an individual's microbiome, is an important aspect of the present invention as approximately 50% of all human cancers have mutant p53. Tumor initiation and maintenance depend upon inactivation of p53. Thus, certain embodiments of the present invention are directed to a method that restores effective amounts of p53 to a person via an individual's microbiome so that p53 can deter cancer cell proliferation and shrink tumor volume. One way in which to accomplish this objective is to have gut microbes produce amounts of p53 such that effective amounts thereof are available to deter cancers. Another route is to provide a modified version of p53 that is more stable and thus, less susceptible to being degraded by bacteria.

More than half of all tumors carry p53 mutations, rendering the p53 gene (aka tp53) the most mutated gene in human tumors. p53 can also be inhibited by mutation-independent mechanisms. Viruses, as well as some pathogenic bacteria, actively inhibit p53 and induce its degradation. This phenomenon was initially described in gastric cells co-cultured with *Helicobacter pylori*, a gram-negative, spiral-shaped pathogen that lives in the stomachs of approximately half of the world's population. The infection is typically acquired during childhood and causes lifelong chronic infection. *H. pylori* infection is considered to be the strongest known risk factor for gastric cancer, and epidemiological studies have estimated that, in the absence of *H. pylori*, 75% of gastric cancers would not occur. *H. pylori* is able to dampen activity of p53 protein by inducing its rapid degradation. One aspect of certain embodiments of the present invention is therefore directed to the provision of modified *H. pylori* bacteria to an individual such that such modified bacteria, lacking its native form ability to dampen the activity of p53, is used to populate the microbiome (e.g. gut microbiome) of an individual so that cancers associated with *H. pylori* are reduced. Moreover, *H. pylori* modified via CRISPR-Cas to express p53 protein, is one method for ensuring that cancer rates in individuals remain low. The population of an individual's microbiome with such modified bacteria is one way in which to alter the conventional microbiome of the person in a manner that lessens the risk of cancer.

As it is known that older people with gastric precancerous lesions, who are infected with *H. pylori*, may be particularly vulnerable to degradation of p53, the treatment of such individuals with modified *H. pylori* bacteria can alter the course of various diseases, including cancer. *H. pylori* inhibits p53 through multiple mechanisms. In the case of *H. pylori*, expression of the CagA virulence factor is sufficient to inhibit p53 and extend short and long term survival of gastric epithelial cells that have DNA damage Inhibition of p53 through the HDM2-dependent mechanism is employed by enteropathogen *Shigella flexneri*, which causes bacillary dysentery in humans. Thus, treatment of such disease states with modified bacteria able to produce desired amounts of competent (e.g. effective, non-mutated, but more stable p53 proteins) is one aspect of the present invention. Thus, in addition to cancer treatments, the modification of certain bacteria to address the levels of p53 expressed thereby is an important aspect of various embodiments of the present invention. For example, down-regulation of p53 protein has been reported in studies of *Neisseria gonorrhoeae*, which is responsible for the sexually transmitted gonorrhea that may increase the risk of genital neoplasms. *N. gonorrhoeae* causes strong genotoxic stress and induces both single and double strand DNA breaks, which is believed to be associated with and can inhibit transcription of the p53 gene.

The p53 pathway is known to affect immune response and among direct transcription targets of p53 are a number of proteins regulating innate immunity and cytokine and chemokine production. p53 is also known to affect NF-.kappa.B activity and pro-inflammatory signaling. One aspect of certain embodiments of the present invention therefore involve the role of immunomodulatory function involved in the bacterial inhibition of p53 which affects the host immune response and permits bacteria to thrive.

In certain embodiments, the use of CRISPR-Cas or cpf1 system is employed to achieve targeted gene deletion for tailoring bacteria for cancer therapy. The above discussion with respect to modifying p53 protein production, e.g. so as to render p53 proteins more stable and less susceptible to degradation, is an example of how CRISPR-Cas systems can be employed to achieve this objective. A bacterial strain is preferably designed by the use of CRISPR-Cas systems in a way that the microorganism is both attenuated and optimized at the same time. For example, auxotrophic/attenuated bacteria may express a complementing gene under an inducible promoter, such that their activation depends on presence of, for example, arabinose or anhydrotetracycline, and thus, such bacteria can be inducibly complemented.

In some embodiments, Gram-negative bacteria, like *Salmonella*, are employed as active delivery vehicles and preferably, instead of depending upon lysis to deliver the contents of the bacterium, a controlled release of a therapeutic compound is facilitated in a manner that achieves continuous expression and release of a therapeutic compound (e.g. such as tomatidine or p53) with a desired high concentration over a period of time to effect cancer reduction, muscle atrophy treatment, etc. One objective is to deliver therapeutic compounds actively and directly to the site of interest by using bacteria of the individual's inherent microbiome. Thus, one aspect of the present invention is directed to the exploitation of the unique tumor colonizing property of bacteria to achieve drug delivery via bacterial mediated tumor therapy. In certain preferred embodiments, use of bioluminescent bacteria are employed to follow the course of the microorganisms into the tumor. While applicable for a number of cancers, in one embodiment, a CRISPR-Cas or cpf1 modified bacterium is used in the treatment of pancreatic cancer with *Listeria monocytogenes*. Thus, in certain embodiments, bacteria are designed to deliver therapeutic compounds like chemotherapeutic drugs directly into the cancerous tissue. In various embodiments, bacteria that reside in an individual's microbiome (e.g oral, gut, vaginal, skin, etc.) are employed as vector systems that provide therapeutic compounds to cancer sites, including solid tumors and in a manner that is far more efficacious than, and that overcomes, the limitations of conventional therapies.

Yet another example of cancer treatments employed using the present invention is the treatment of esophageal adenocarcinoma (EA), which has increased 6-fold in the U.S. since the 1970s, as well as pancreatic cancers. No one knows why. High antibody levels for one of the more infectious periodontal bacterium strains of *Porphyromonas gingivalis* have been associated with a two-fold risk for pancreatic cancer. Individuals with high levels of antibodies for some kinds of harmless "commensal" oral bacteria were associated with a 45-percent lower risk of pancreatic cancer. Thus, one aspect of the present invention is directed to the reduction in pancreatic cancer via modification of an individual's microbiome, and in particular their oral and gut microbiomes. Administration of modified oral and gut bacteria having desired characteristics as described herein is one way in which to reduce the incidence of pancreatic cancer.

Yet another aspect of the present invention is directed to the use of human specific species of bacteria that are then modified to enhance one or more characteristics deemed beneficial to the microbiome of an individual, including bacteria that have been modified via a CRISPR-Cas9 and/or Cpf1 systems (CRISPR-Cas12a) to either repress the expression of a particular protein or lipid, or to increase the production of beneficial microbial secretions, including but not limited to tomatidine and p53 protein. One objective of such embodiments is to avoid modifying an individual's human genome in order to treat a disease state. One can avoid modifying the human genome and still significantly affect the health of humans by instead employing modifications to the skin, oral and gut microbiomes. Use of human specific strains of bacteria, whether they are commensal or pathogenic, including bacteria that are modified to alter their native pathogenicity, is one preferred aspect of many embodiments of the present invention. In particular, in view of the tropism demonstrated by *S. pyogenes* for humans, and the recognition that such bacterial species is found in both the oral and skin microbiome of humans, *S. pyogenes* is a preferred bacterial species to employ in various embodiments of the present invention to treat various disease states.

In various embodiments, re-cultivated human intestinal microbiota obtained by cultivation of a stool sample in a cultivation medium is employed to promote the proliferation of select bacteria, including at least two of the following Phyla: Bacterioidetes, Firmicutes, Proteobacteria and Actinobacteria, and more preferably at least two of the following: *Faecalibacterium, Lachnospira, Veillonella, Rothia; Lactobacillus johnsonii* and *Prevotella*. In other embodiments, one or more of the following microorganisms is employed: *Bifidobacterium lognum, B. infantis* BCRC 14602; *Prevotella; Ruminococcus, Bifidobacterium infantis, Lactobacillus acidophilus, Bacteroides fragilis, B. longum* bv. *infantis* isolate UCD272; *B. infantis* BCRC; *B. longum* bv. *infantis*, AY151398; and *Lactobacillus ruminus; L. lactis, L. lactis cremoris, L. plantaru*, and *L. raffinolactis; Faecalibacterium, Lachnospira, Veillonella*, and *Rothia; Lactobacillus johnsonii, Lactobacillus crispatus, Lactobacillus brevis, Lactobacillus buchneri, Lactobacillus casei, Lactobacillus delbrueckii, Lactobacillus fermentum, Lactobacillus helveticus, Lactobacillus kefir, Lactobacillus paracasei, Lactobacillus plantarum, Lactobacillus rhamnosus, Lactobacillus salivarius, Streptococcus thermophilus, Lactococcus lactis, Lactococcus plantarum, Lactococcus raffinolactis, Leuconostoc lactis, Leuconostoc mesenteroides, Enterococcus faecalis*, and *Enterococcus faecium; Enterococcus faecalis; Lactobacillus reuteri*, and *Lactobacillus paracasei*. In certain embodiments, the method includes the use of a mixed culture of bacterial cells of three to eight species of lactic acid bacteria. In particular mixed cultures, the following may be included: *Saccharomyces cerevisiae, Lactobacillus delbrueckii, Lactobacillus acidophilus, Lactobacillus plantarum, Lactobacillus fermentum, Lactobacillus casei, Lactobacillus rhamnosus, Lactococcus lactis* and *Streptococcus thermophilus; Enterococcus faecium; Bacillus coagulans; Leuconostoc, Pediococcus, Lactobacillus casei, Lactobacillus plantarum, Lactococcus lactis* subspecies *lactis, Lactococcus lactis* subspecies *cremoris; Lactobacillus plantarum; Pediococcus pentosaceus; Streptococcus thermophilus; Lactobacillus paracasei; Lactobacillus plantarum, Lactobacillus gasseri* and *Lactobacillus salivarius; Lactobacillus acidophilus* PM-A0002, *Lactobacillus gasseri, Lactobacillus salivarius, Lactobacillus acidophilus* PM-A0013; *Leuconostoc mesenteroides; Lactobacillus bulgaricus, Lactobacillus rhamnosus, Lactobacillus acidophilus, Lactobacillus paracasei; Bifidobacterium bifidum; Lactobacillus brevis; Enterococcus durans, Leuconostoc mesenteroides; Lactobacillus crispatus*. Still other embodiments of the invention may comprise extracts obtained from one or more of the following species: *Lactobacillus fermentum, Lactobacillus rhamnosus, Lactobacillus plantarum, Lactobacillus johnsonii, Lactobacillus helveticus, Lactobacillus casei defensis, Lactobacillus casei* ssp. *casei, Lactobacillus paracasei, Lactobacillus bulgaricus, Lactobacillus paracasei, Lactobacillus acidophilus, Lactobacillus reuteri, Lactobacillus salivarius*, and *Lactobacillus lactis*. In some embodiments, at least one strain from each of the above species of bacteria is used, while in other embodiments, one or more specific strains from the list above may be removed or substituted with one or more different strains. In particular, some embodiments of the present invention comprise an extract obtained from one or more of the following bacterial strains: *Lactobacillus fermentum* 1-3929, *Lactobacillus rhamnosus* 71.38, *Lactobacillus plantarum* 71.39, *Lactobacillus johnsonii* 103782, and *Lactobacillus helveticus* 103146; *Lactobacillus fermentum* 1-3929, *Lactobacillus rhamnosus* 71.38, *Lactobacillus plantarum* 71.39, *Lactobacillus johnsonii* 103782, and *Lactobacillus helveticus* 103146. The following bacteria species may also be employed: *Lactobacillus acidophilus* PM-A0002 deposit number M 207038, *Lactobacillus gasseri* PM-A0005 deposit number M 207039, *Lactobacillus salivarius* PM-A0006 deposit number M 207040, *Lactobacillus johnsonii* PM-A0009 deposit number M 207041 and *Lactobacillus acidophilus* PM-A0013 deposit number M207042. Certain other embodiments of the present invention include a combination of particular bacterial strains, selected from the group consisting of *Prevotella; Lactobacillus johnsonii; Bacteroides fragilis, Lactobacillus ruminus*, and at least one of *B. longum* bv. *infantis* isolate UCD272 or *B. longum* bv. *infantis*, AY151398. In more preferred embodiments, the gut microbiome of an individual is modified by providing in preferably a pill form a collection of microbes that include at least two of the following Phyla: Bacterioidetes, Firmicutes, Proteobacteria and Actinobacteria, and more preferably at least two of the following: *Faecalibacterium, Lachnospira, Veillonella, Rothia; Lactobacillus johnsonii* and *Prevotella*.

As one of ordinary skill in the art will appreciate, one must give value to their existence by behaving as if one's very existence were a work of art. You must have chaos within you to give birth to a dancing star. And those who were seen dancing were thought to be insane by those who could not hear the music. To live is to suffer, to survive is to find some meaning in the suffering. No one can construct for you the bridge upon which precisely you must cross the stream of life, no one but you yourself alone. There will always be rocks in the road ahead of us. They will be stumbling blocks or stepping stones; it all depends on how you use them. The center is everywhere. Bent is the path of eternity.

In still other embodiments, interspecies interactions within mixed microbial communities is involved, with the objective being to modify competitive relationships involving nonbiocidal biosurfactants, enzymes, and metabolites produced by bacteria and other microorganisms in a manner such that selection of particular bacterial species can be employed to do one or more of inhibit initial adhesion, trigger matrix degradation, encourage jamming of cell-cell communications, and induce biofilm dispersion. Nonbiocidal molecules are thus employed to modify competitive interactions within biofilms in a manner that promotes the overall health of an individual's microbiome.

In certain embodiments, particularly designed to address the proper developmental biology of a human's immune system, so important in early and later life ability to thwart cancerous conditions, a bacterial formulation is applied to newborns within a critical window of time after birth, preferably within the first 24 hours of the newborn's birth, more preferably within 6 hours of their birth, even more preferably within 3 hours of birth, and most preferably within an hour after their birth. The administration can be by several methods, but preferably is a lotion, ointment or gel that is rubbed onto the newborn's skin, preferably all over his/her entire body. A spray or mist can also be applied that contains the bacterial and microbe formulations as set forth herein. While not bound by theory, the critical window to apply to the newborn's skin the referenced formulations, e.g.

microbial mixtures of bacteria beneficial in triggering immune system development as further described herein, is within a relatively short time period and is necessary to establish immune tolerance to a variety of commensal microbes. The manner in such and the content of microbes presented at a time in which a newborn has his/her skin, oral cavity and gut microbiome colonized establishes immune tolerance to particular commensal microbes. The influx of highly activated T cells into neonatal skin and gut is believed to occur in such critical window. So a mother of a newborn has a choice: to simply rely upon chance as to what particular microbes might be present during this critical window of the newborn's establishing immune tolerance to particular bacteria and other microbes; or to provide the newborn with a selected formulation containing predetermined microbes such that the newborn's developing immune system can properly react to the microbes in the predetermined formulation, and thus provide the newborn with the opportunity to develop a more expansive immune tolerance profile. The mechanism that promotes tolerance is tissue specific, and thus, the skin, oral cavity and the gut may have different ways by which to mediate tolerance to commensal microbes. For example, to establish a healthy status of a newborn's skin as it relates to commensal microbes on its skin, the particular type of microbes, including bacteria, brought into contact with his/her skin is achieved in a certain time period after birth (e.g. within 1 to 24 hours after birth) so that the developing immune system of the infant establishes tolerance to such microbes, thus avoiding allergies, autoimmune diseases and other related diseases, as well as chronic inflammation of the skin.

In certain embodiments of the present invention, the skin/oral and gut microbiome is enhanced via providing microbes able to metabolize lipids, proteins and carbohydrates, and thus, with respect to the skin microbiome, produce acid that aids in maintaining the so-called "acid mantel" of the skin. In preferred embodiments the bacteria that is modified has a very narrow host tropism, such that the bacteria are specific for the human species and thus, their modification poses little if any risk to other animals or organisms.

Other embodiments are directed to combating infections of a person's skin by the bacteria *Staphylococcus aureus*. Patients with malignancies represent a population at high risk for drug-resistant infections. *S. aureus* is a significant cause of morbidity and mortality in pediatric oncology patients. *Staphylococcus aureus* is a commensal and pathogen of both humans and cattle. In certain embodiments the accessory gene regulator (Agr) system and the virulence regulation of *S. aureus* pathogenesis is modified to delete or to at least reduce the virulence of the bacteria. In such a way, the present invention provides a way to effectively combat *S. aureus* infections. In various embodiments of the present invention, CRISPR-Cas9 and/or Cpf1 systems are employed to render ineffective the virulence factors of such bacteria involved with the establishment and propagation of infection. Several molecules have been found to interfere with *S. aureus* virulence regulation, especially those targeting the Agr quorum-sensing signaling molecule. By modification of this bacterial species using CRISPR-Cas and/or Cpf1 it is possible to achieve broad-spectrum inhibitory effects on most *S. aureus* strains and Agr subtypes.

The tropism of individual bacteria for particular host tissues (e.g., skin vs. respiratory tract vs. gastrointestinal tract) is determined by the array of available adhesion-receptor pairs. In preferred embodiments, bacteria having substantial, if not entire, human host specificity are employed. For example, *Salmonella enterica* serovar *Typhi*, known to be the bacteria responsible for typhoid fever, a life-threatening human disease, demonstrates strict human host specificity. In certain embodiments, the virulence factors of such bacteria are compromised by being modified via the CRISPR-Cas or Cpf1 system to render the modified bacteria as non-pathogenic. Similarly, the bacteria *Neisseria*, the causative agent of gonorrhea, is a disease restricted to humans, and thus similar CRISPR-Cas and/or Cpf1 systems may be employed to reduce if not eliminate the virulence factors of such bacteria. Likewise, *Helicobacter pylori* is known to be an etiologic agent of gastritis and peptic ulcer disease in humans. The iron acquisition system of *H. pylori* by the human lactoferrin receptor system is believed to play a major role in the virulence of *H. pylori* infection. The CRISPR-Cas and/or Cpf1 systems may be employed to reduce if not eliminate the virulence factors of this bacteria. Yet another bacteria demonstrating human tropism is *Haemophilus* influenza, a Gram negative species that requires heme and has exclusive human host specificity. The precise way in which to employ CRISPR-Cas systems is relatively straightforward and is described in great detail in various references that are incorporated herein for written description and enablement purposes. In certain embodiments, the CRISPR-Cas and/or Cpf1 systems may be employed to reduce if not eliminate the virulence factors of such bacteria. The distinction between throat and skin group A *Streptococcus* has become blurred and to date there have been few advances in treatment of group A *Streptococcus* skin infections. Certain aspects of the present invention include the modification of skin group A *Streptococcus* to reduce the likelihood, if not prevent, related skin diseases, including eczema, atopic dermatitis, acne, allergic inflammation, skin hypersensitivity, UV-induced skin damage, skin cancer.

The present invention in various embodiments is directed to a variety of consumer products including cosmetic products such as skin care products (bath preparations, skin washing and cleaning products, skin care products, eye cosmetics, lip care products, nail care products, intimate hygiene preparations, foot care), those with special effects (sunscreens, tanning agents, deodorants, anticholinergics, depilatories, shaving, fragrance), those for oral or dental hygiene and those for hair care (shampoos, conditioners, etc. One objective of the present invention is to achieve various health and cosmetic benefits by providing a healthy, balanced skin, oral and gut microbiome. Other embodiments are directed to prebiotic agents for use with those microbiomes. In preferred embodiments, CRISPR-Cas and/or Cpf1 modified bacteria, especially those demonstrating total or substantial tropism for humans, are employed in one or more of the above referenced products, with certain features, namely, virulence factors, reduced if not eliminated. In such a manner, there is a competitive inhibition of undesired bacteria with the modified bacteria as set forth herein.

In certain embodiments, the cleansing of one's skin to effectively reduce by at least about 50%, more preferably about 30%, and most preferably to reduce by at least about 25%, of native bacteria on an individual's skin portion to be addressed, is performed prior to purposefully contacting the individual's skin with one or more bacteria species that have been modified via employment of a CRISPR-Cas and/or Cpf1 system to reduce if not effectively compromise the virulence factors of such bacteria, and more preferably a bacteria that has a host specificity exclusive to humans. Similarly, treatment of the oral and gut microbiome can be addressed by such an initial reduction in the native bacterial and other microbe populations of an individual, followed by repopulation of such microbiomes with desired modified bacteria, especially those modified via CRIPSR-Cas systems.

The adherence to the skin of problem flora, such as pathogenic bacteria and yeast, has been associated with numerous ailments, including skin infections, diaper rash, urinary or vaginal infections, and malodors. Various products are commercially available to clean the surface of skin and to remove problem flora therefrom. Many presently available products include an antibacterial agent, such as an organic acid, which can be used in combination with the surfactant to kill bacteria located on the skin's surface. Also, various antibacterial soaps and cleansers are available to cleanse hands and kill flora adhered to the skin's surface. These antibacterial soaps are generally highly effective in killing bacteria located on the skin.

Various embodiments of the present invention stand in contrast to accepted methods of dealing with skin and bacteria issues (which largely solely involve killing bacteria, etc.—such as described in Kimberly Clark's U.S. Pat. No. 8,110,215 to Koenig, et al.) In contrast, various embodiments of the present invention are directed to modification of various bacteria on a person's skin (and in still other embodiments to the gut and oral microbiome) so as to reduce the pathogenicity thereof and to rely upon competitive inhibition of such modified bacteria on the skin to further reduce the presence of pathogenic bacteria on an individual's skin.

As for lotions of the present invention, in preferred embodiments, there is an objective to limit if not preclude the use of phthalates, which are extremely toxic and are believed to also be human carcinogens. Thus, in preferred embodiments of the present invention, such lotions do not employ such toxic agents, and in particular, agents toxic to bacterial species for which the inventors suggest be used, e.g. those modified to reduce pathogenicity, virulence factors, etc., so as to establish a population of such modified bacteria on a person's skin, and in such a manner, reduce the incidence of skin infections and diseases. Thus, lotions, creams, gels, etc. that include such toxic agents, including but not limited to phthalates, are not employed, but rather, lotions that provide an environment for the bacteria as set forth herein to survive and to thus be available to provide benefits to the skin of individuals to which they are applied, are particularly preferred.

Healthy, normal skin exhibits a slightly acidic pH in the range of 4.2-5.6, which aids in the prevention of pathogenic bacterial colonization, regulation of enzyme activity, and maintenance of a moisture-rich environment; however, after the age of 70, the pH of skin rises significantly, stimulating protease activity. Thus, one objective of several embodiments of the present invention is directed to lowering the pH of the skin of an individual, especially those at about the age of 70, so as to encourage a skin environment conducive to the proliferation of one or more bacteria that have been modified to promote skin health and to reduce the ability of undesired bacteria from colonizing the skin of the person. Probiotic metabolism frequently produces acidic molecules, lowering the pH of the surrounding environments seen with Lactobacilli producing free fatty acids (FFAs) and conjugated linoleic acid (CLA) during the fermentation process. Thus, the use of probiotics is employed to restore the normal skin pH and consequently return protease activity levels closer to those seen in young, healthy skin.

The main microbes that reside on human skin can be divided into four phyla: Firmicutes, Actinobacteria, Proteobacteria, and Bacteroidetes. *Staphylococcus* spp. and *Corynebacterium* spp. are the dominant bacteria at the genus level. Significantly fewer *Corynebacterium* spp. have been observed in cachexia patients compared to healthy subjects. The presence of cancer and cachexia alters human skin bacterial communities. Understanding the changes in microbiota during cancer cachexia has lead to new insights into the syndrome. Especially with tomatidine administration and enhanced bacteria, the provision of such modified bacteria to a person's microbiomes, including the gut, oral and skin microbiomes, provides a way to address numerous issues arising from cancer cachexia.

Competitive inhibition is relied upon in various embodiments of the present invention to advance the repopulation of skin, oral cavity and gut environments with beneficial microbes. For example, and using the skin microbiome as one specific case, in one embodiment, repopulating an individual's skin with beneficial bacteria, preferably in balanced percentages and having preferred species provided, can be used in conjunction with an antimicrobial composition. Preferably, an antimicrobial is first administered to suppress or eradicate the resident populations of bacteria on a person's skin, including any abnormal organisms or pathogenic bacteria, then the normal flora is repopulated by the administration of at least one of the modified bacteria as described herein, including those modified using CRISPR-Cas and/or Cpf1 systems to delete certain portions of genes or to add certain genes to facilitate the colonization of a person's skin with beneficial bacteria that maintain the general health of a person's skin.

The term "therapeutically effective amount" as used herein means the amount contained in the composition administered that is of sufficient quantity to achieve the intended purpose, such as, in the case of cachexia, an amount that is able to reduce muscle wasting activities that cause a loss of muscle weight in an individual.

It is preferred in many embodiments that antimicrobial treatments are completed before the administration of modified bacteria—selected as being desirable to maintain skin, oral or gut micriobiome health, including but not limited to modified bacteria of the following: Firmicutes (mainly *Streptococcus* and *Staphylococcus*) and Actinobacteria (mainly *Corynebacterium* and *Propionibacterium*). By employing such modified bacteria, one is able to establish and maintain the reduction if not preclusion of various skin diseases, including skin cancer. One objective of certain aspects of the present invention is to provide a method and system that, by using health promoting strains from the microbiome in topical probiotics, it is possible to treat and to further reduce the risk of skin cancer. One of skill in the art will appreciate similar objectives in the treatment of the oral and gut microbiomes for diseases that affect the same.

Repair of tissue wounds is a fundamental process to re-establish tissue integrity and regular function. Infection is a major factor that hinders wound healing. Multicellular organisms have evolved an arsenal of host-defense molecules, including antimicrobial peptides (AMPs), aimed at controlling microbial proliferation and at modulating the host's immune response to a variety of biological or physical insults. Certain embodiments of the present invention are directed to the use of AMPs as endogenous mediators of wound healing. Thus, one aspect of several embodiments of the present invention is directed to genetically manipulating bacterial species native to the skin. *Staphylococcus epidermidis*, which is found in abundance on human skin, can cause immune tolerance in some—but in others, inflammation and activation of T cells against the bacteria. The present inventors submit that the immune system may set up tolerance to commensal bacteria only early in life, during a time where there is an influx of regulatory T cells unique to the skin, e.g. during the first week after birth. This colonization of the skin by regulatory T cells—immune cells that dampen the responses of effector T cells—is believed to be required for tolerance to *S. epidermidis*. There is an abrupt wave of regulatory T cell infiltration into neonatal skin that occurs at a defined period and this window dictates the achievement of commensal-specific tolerance.

One aspect of the present invention is directed to the introduction of tolerance to commensal bacteria during the time the developmental window is still open, thus providing the individual with life-long protection from a variety of diseases. Still other embodiments, however, are directed to introducing tolerance following the closing of the developmental window, e.g. after the first week after birth, so that individuals can purposefully be induced to have commensal-specific tolerance as an adult. Understanding which microbes cause infection and which are tolerated and the critical time frames where the immune status is set is one aspect of the present invention.

Skin bacterial communities are influenced by ethnicity, lifestyle and/or geographic location. Skin bacterial communities that are particularly employed in the modifications as set forth herein include: Firmicutes, Proteobacteria and Actinobacteria); Firmicutes (mainly *Streptococcus* and *Staphylococcus*) and Actinobacteria (mainly *Corynebacterium* and *Propionibacterium*), while still other preferred bacteria include *L. acidophilus* NCFM, *L. salivarius* Ls-33, *Bifidobacterium lactis* 420, *L. acidophilus* La-14 and *Propionibacterium jensenii* P 63.

In various embodiments, cosmetics are provided that provide for a medium favorable for maintaining a desired physio-chemical balance of the skin without favoring the development of pathogenic microorganisms. To achieve this objective, certain oligosaccharides that are metabolized by several beneficial strains of the skin microflora, such as *Micrococcus kristinae, Micrococcus sedentarius, Staphylococcus capitis, Corynebacterium xerosis* and *Lactobacillus pentosus*, are employed in formulations, in conjunction with one or more of the modified bacteria as described herein, including those modified to produce tomatidine and/or p53 proteins.

Pathogenic strains such as *Staphylococcus aureus, Gardnerella vaginalis* and *Propionibacterium acnes* do not typically metabolize, or very slightly metabolize, certain oligosaccharides. In certain embodiments, sugar sources are provided in amounts and in association with beneficial bacteria, whether they be those modified as described herein, or those that are naturally non-pathogenic in nature, so as to achieve the colonization of the skin in a fashion to provide the health benefits sought.

Yet another aspect of the present invention is directed to the treatment of brain cancer, which is the leading cause of cancer-related death in patients younger than age 35 and accounts for roughly 10% of all cancers diagnosed in North America. Treatment of brain tumors is complicated by the fact that there are more than 120 different types, which range from low grade astrocytomas to high grade glioblastomas (GBM). Malignant gliomas, such as GBM, are by far the most common brain cancer found in adults and one of the most difficult to treat. Even with aggressive single and multimodal treatment options such as surgery, chemotherapy, radiation and small molecule inhibitors, the survival has remained unchanged over the past three decades with a median survival of less than one year after diagnosis. Reasons for the failure of conventional treatments is multifactorial including the highly infiltrative/invasive nature of GBM, limitation of drug delivery through the blood brain barrier and neural parenchyma, and genetic heterogeneity resulting in intrinsic resistance to available treatments and the rise of aggressive resistant clones.

To address such brain tumors, one aspect of the present invention is directed to the delivery of tomatidine and/or p53 directly to tumors through interstitial therapy, where a surgeon implants small e.g. dime-sized strips having the agent as desired, e.g. tomatidine, p53, etc. and the preferably biodegradable strips that comprise such agents are delivered directly into the tumor so that they may release desired concentrations of the agent(s) locally over a period of days or weeks, prior to safely dissolving. Such strips can be customized to treat a variety of solid tumor disease of the breast, lung, colon, kidney and skin. The inventors incorporate by reference various novel technologies relating to the use of strips, such as oral strips as described in U.S. Pat. No. 9,010,340 and Ser. No. 14/611,458. One of skill in the art will appreciate the modifications to such strips to employ their use in the various cancer treatment regimens as described herein.

In one particular aspect of the present invention, the Zika virus is employed in the treatment of brain cancer due to its ability to target human brain cells. Employing such targeting in combination with the other aspects of the present invention as described herein, including the production of tomatidine and/or p53 by an individual's microbiomes, offers new hope for an effective treatment of particular brain cancers. Zika virus is a member of the Flaviviridae family, which includes West Nile Virus, St. Louis encephalitis virus, Kunjin virus, yellow fever virus, Dengue virus, and Japanese encephalitis virus. Cellular apoptosis (cell death) and necrosis follow infection for many of these viruses, and appears to be dependent upon several factors, such as viral load, host factors, and specific viral protein induced apoptosis/necrosis pathways, many of which have yet to be fully defined. The expression of BAX is regulated by the tumor suppressor p53. The majority of BAX is found in the cytosol, but upon initiation of apoptotic signaling, BAX undergoes a conformational shift and becomes mitochondrial membrane associated.

Still another aspect of the present invention is directed to the use of particular mushroom extracts to combat cancer, especially when combined with tomatidine to address the muscle atrophy commonly associated with cancer. Use of particular compounds derived from mushrooms, especially those produced by modified bacteria resident in an individual's microbiome and that are provided via the use of CRISPR-Cas or Cpf1 systems, is a new way to address treatment of many cancer types. For example, the small-molecule neoalbaconol (NA) from *Albatrellus confluens* possesses the ability to inhibit cell growth of many cancer cells. Neoalbaconol is a natural compound extracted from the mushroom *Albatrellus confluens*, and induces necroptosis. Neoalbaconal inhibits proliferation in various tumor cell lines, especially in breast cancer and nasopharyngeal carcinoma. Neoalbaconal targets PDK1 to inhibit the downstream PI3-K/Akt pathway and blocks the generation of ATP in a time-dependent manner. Cholangiocarcinoma (CCA) is a lethal malignancy with poor prognosis that makes up 10-25% of all primary liver cancer diagnosed worldwide. *Albatrellus confluens*, mainly distributed in Southwest China, is a member of the Polyporaceae family. Several compounds with anticancer potential have been isolated from this fungus and NA has proven to be efficacious in inhibiting the growth of a broad spectrum of tumor cell lines.

Dosage administration for mice would be NA treatment (100 mg/kg/day)—and thus, for humans, would be commensurate with the person's size being treated. When combined with tomatidine, an effective treatment for cancer and one that addresses muscle atrophy associated with cancer. Preferably, at least about 5 mg of tomatidine every day is provided to an individual via the production thereof by gut microbes in such individual. Systemic administration of one or more disclosed compounds (e.g., by parenteral injection or by oral consumption) can be used to reduce fat, increase the muscle to fat ratio, increase the muscle mass and reduce the fat, and prevent an increase in fat in an animal.

It is known that most human viruses impair p53 activity. For example, in cervical cancer, the human papillomavirus E6 protein targets p53 for degradation. Bacterial infection triggers the p53 pathway and to activate p53 isoforms and the p53 R249S variant is often observed in liver cancer as being associated with aflatoxin B1 food contamination.

In one aspect of the present invention, CRISPR tools are employed to insert into cancer cells particular sequences that encode for the expression of toxins. Appropriate promoters are used to then "turn on" the expression of such genes, thus enabling amounts of toxins to be made by the cancer cell, destroying itself. In other words, this is similar in concept to "infecting" a cancer cell with a particular DNA or RNA insert, whether in the nuclear DNA or in the mitochondrial DNA (or RNA of the cell) and by activating promoters to effectively "turn on" the production of the protein (e.g. a toxin), one can control the destruction of the cell. Similarly, stretches of DNA can be inserted into cancer cells such that when a later infection with a predetermined bacterial species occurs, the normal immune response of the individual's resident immune system will target such DNA stretches, and the targeting step itself can be used to provide the cancer cells with suitable components that ultimately reduce the growth of cancerous tissue and/or kill such cells. Other systems employ CRISPR tools to ensure that cancer cells, when attempting to counter the infection by a virus, results in turning on destructive machinery that selectively kills the cancer cell in the process.

Yet other embodiments that are directed to the treatment of throat cancers employ factors of the disease causing bacteria *Streptococcus pyogenes*. For example, in one embodiment, the hyaluronic acid capsule of *Streptococcus pyogenes*, along with its M proteins, which are a major factor behind its virulence due to their role in the attachment to host tissues. Host immunity to *Streptococcus pyogenes* results from the development of antibodies specific to M protein and the hyaluronic acid capsule of *Streptococcus pyogenes* is chemically similar to human connective tissue, which allows it to go unrecognized as an antigen by the host's body. Adhesion of *Streptococcus pyogenes* to the host cell is the first step in pathogenesis, and the invasion process into the host cells takes place in very short order.

*S. pyogenes* adhesion to human cells depends on the presence of cell surface adhesions including the M protein. The cell wall associated M protein is a major virulence factor of *S. pyogenes*, which can bind directly to the extracellular matrix components (e.g. fibrinogen).

*S. pyogenes* possesses an arsenal of countermeasures against attacks from the host, including resistance of phagocytosis that is mediated by the hyaluronic acid capsule.

In various embodiments of the invention as described herein, components of CRISPR-Cas or Cpf1 systems are involved in the regulation of bacterial gene expression. As Cas proteins have proven to be great biotechnology tools, these novel functions are used in various embodiments of the present invention for gene regulation of bacteria that comprise the human microbiome. In particular, a particular class of riboswitches, called thermosensors can sense temperature changes and can be used effectively with especially gram-positive bacteria, in contrast to Gram negative bacteria, which use translational attenuation.

Still another aspect of the present invention is directed to the production of rapamycin, a small molecule drug derived from *Streptomyces hygroscopicus*, by bacteria in a person's microbiome. Much of the role and function of mTOR has been ascertained with rapamycin, a known macrolide antibiotic produced by *Streptomyces hygroscopicus*. The mechanistic target of rapamycin (mTOR) is an evolutionarily conserved serine/threonine kinase that is ubiquitously expressed in immune cells. mTOR integrates multiple environmental signals to regulate diverse cellular processes including protein translation, cell growth, proliferation, metabolism, migration, and survival. Bacterial pathogens including *Listeria monocytogenes* (*L. monocytogenes*) and *Staphylococcus aureas* can also activate mTOR to promote IL-10 production and increase their survival in the host.

Isolated from *Streptomyces hygroscopicus* var. Ascomycetes, pimecrolimus is a calcineurin inhibitor which inhibits T-cell stimulation by antigen-presenting cells, blocking both T helper cell 1 (Th1) cytokines such as IL-2 and interferon (IFN-.gamma.) and T helper cell 2 (Th2) cytokines including IL-4 10. It also inhibits mast cell release of hexosaminidase, tryptase, and histamine. Topical pimecrolimus, like topical glucocorticoids, improves the atopic dermatitis-like skin lesions and barrier impairment (important for asthma development in atopic dermatitis patients), by suppressing thymic stromal lymphopoietin-(TSLP-) related allergic inflammation. TSLP is an epithelial cell-derived IL-7-like cytokine which has an important role in allergic inflammatory immune response, particularly in dendritic cell-mediated allergic inflammation in allergic asthma and atopic dermatitis, since it converts human epidermal Langerhans cells into antigen-presenting cells which than induce proallergic T-cells.

Pimecrolimus is used in the treatment of Atopic dermatitis (the only one indication approved by the FDA), but it has been effectively used to treat erosive oral and genital lichen planus, vulvar lichen sclerosus, Fox-Fordyce disease, intertriginous psoriasis, seborrheic dermatitis, erosive circinate balanitis, discoid lupus erythematosus, vulvar pruritus, vitiligo, and GVHD. Pimecrolimus has similar efficacy as low to moderately potent topical corticosteroid creams for mild to moderate Atopoic dermatitis during the first 5 to 6 years of life, with similar rates of adverse events.

Topical calcineurin inhibitors are primarily used in the treatment of Atopic dermatitis, which is not defined as a genetically predisposed dry hypersensitive skin any more, but as acute eczematous skin, which emphasizes the crucial role in skin barrier integrity and extrinsic Atopic dermatitis. Topical therapy includes basic therapy that enhances the restoration and maintenance of the epidermal barrier.

In certain embodiments of the present invention, antibiotic resistance of certain bacteria is modulated by employment of CRISPR to insert into the genome of a bacteria antibacterial sensitivity such that it can selectively be killed, if necessary, after it is employed to trigger desired immune responses in a new born or other individual.

CRISPR-Cas systems employ CRISPR RNAs to recognize and destroy complementary nucleic acids. In various embodiments of the present invention, CRISPR-Cas systems are used as programmable antimicrobials to selectively kill bacterial species and strains such that desired selected targets can be focused on such that virtually any genomic location may be a distinct target for CRISPR-based antimicrobials, and that, in conjunction with an appropriate delivery vehicle, such as those employed by Bikard et al. and Citorik et al., one is able to effectively deploy a CRISPR-Cas system as an antimicrobial agent.

Another aspect of certain embodiments include making synthetic CRISPR-containing RNAs that target genes of interest and using them with Cas enzymes. The specificity of CRISPR-Cas systems permits one to design methods to target a single bacterial species so that only essential genes from that one species is targeted and cut up. CRISPR-Cas systems are employed in various ways in the many embodiments of the present invention to retain the beneficial bacterial communities intact and to offer protection against undesired bacterial pathogens.

CRISPR has a certain protein in it called Cas9 that acts like a scissor as it recognizes specific sequences of DNA and cuts it enabling one to perform genome-editing of a bacterial genome in a person's microbiome. There exists another CRISPR system, CRISPR-Cpf1 that is even more preferred for use in microbial systems. Cpf1 is important in bacterial immunity and is well adapted to slice target DNAs. Cpf1 prefers a "TTN" PAM motif that is located 5' to its protospacer target—not 3', as per Cas9, making it distinct in having a PAM that is not G-rich and is on the opposite side of the protospacer. Cpf1 binds a crRNA that carries the protospacer sequence for base-pairing the target. Unlike Cas9, Cpf1 does not require a separate tracrRNA and is devoid of a tracrRNA gene at the Cpf1-CRISPR locus, which means that Cpf1 merely requires a cRNA that is about 43 bases long—of which 24 nt is protospacer and 19 nt is the constitutive direct repeat sequence. In contrast, the single RNA that Cas9 needs is still .about.100 nt long. Cpf1 is apparently directly responsible for cleaving the 43-base cRNAs apart from the primary transcript.

With respect to the cleavage sites on the target DNA, the cut sites are staggered by about 5 bases, thus creating "sticky overhangs" to facilitate gene editing via NHEJ-mediated-ligation of DNA fragments with matching ends. The cut sites are in the 3' end of the protospacer, distal to the 5' end where the PAM is. The cut positions usually follow the 18th base on the protospacer strand and the 23rd base on the complementary strand (the one that pairs to the crRNA). In Cpf1 there is a "seed" region close to the PAM in which single base substitutions completely prevent cleavage activity. Unlike the Cas9 CRISPR target, the cleavage sites and the seed region do not overlap. One advantage of the present invention, as compared to techniques that rely on CRISPR systems to modify mammalian cells, is that the system and method of preferred embodiments are directed to bacterial systems—rather than eukaryotic systems. It is believed that Cpf1 may be better than Cas9 for mediating insertions of DNA, namely because its guide RNA is only 43 bases long, making it feasible to purchase directly synthesized guide RNAs for Cpf1, with or without chemical modifications to enhance stability.

The CRISPR system may be employed in various embodiments to strengthen antibiotics or to kill the bacteria altogether. By removing the bacteria's genes that make them antibiotic-resistant, CRISPR can boost the effectiveness of existing drugs. CRISPR can also be used to remove a bacteria's genes that make them deadly and facilitate RNA-guided site-specific DNA cleavage. Analogous to the search function in modern word processors, Cas9 can be guided to specific locations within complex genomes by a short RNA search string.

In various embodiments, the CRISPR-Cas systems is employed to control the composition of the gut flora, such as by circumventing commonly transmitted modes of antibiotic resistance and distinguishing between beneficial and pathogenic bacteria. For applications that require the removal of more than one strain, multiple spacers that target shared or unique sequences may be encoded in a single CRISPR array and/or such arrays may be combined with a complete set of cas genes to instigate removal of strains lacking functional CRISPR-Cas systems. Because of the sequence specificity of targeting, CRISPR-Cas systems may be used to distinguish strains separated by only a few base pairs. Thus, in many embodiments, CRISPR-Cas systems provide for the selective removal of microorganisms to trigger certain predictable development of the immune system.

The specificity of targeting with CRISPR RNAs may be employed to readily distinguish between highly similar strains in pure or mixed cultures. Thus, in certain embodiments, varying the collection of delivered CRISPR RNAs is employed to quantitatively control the relative number of individual strains within a mixed culture in a manner to circumvent multidrug resistance and to differentiate between pathogenic and beneficial microorganisms.

Use of CRISPR-Cas provides a generalized and programmable strategy that can distinguish between closely related microorganisms and allows for fine control over the composition of a microbial population for use in the present invention. Thus, the RNA directed immune systems in bacteria and archaea called CRISPR-Cas systems is employed in various embodiments of the present invention to selectively and quantitatively remove individual bacterial strains based on sequence information. Thus, such genome targeting using CRISPR-Cas systems allows one to specifically remove individual microbial species and strains.

In various embodiments, it is desirable to remove—using CRISPR-Cas systems—particular pathogenic bacteria and/or simply the pathogenic portions of such bacteria—while sparing other desired commensal bacteria.

In various embodiments, one of skill in the art will appreciate that removal of particular strains of bacteria may be achieved using both type I and type II CRISPR-Cas systems, given the distinction between these systems being that type I systems cleave and degrade DNA through the action of a 3'-to-5' exonuclease, whereas type II systems only cleave DNA. In still other embodiments, multiple guide RNAs can also be used to target several genes at once. The use of effector fusions may also expand the variety of genome engineering modalities achievable using Cas9. For example, a variety of proteins or RNAs may be tethered to Cas9 or sgRNA to alter transcription states of specific genomic loci, monitor chromatin states, or even rearrange the three-dimensional organization of the genome.

CRISPR-Cas can be used on the various identified microbiome constituents to modify gene expression, including cutting of a gene, repress or activate a gene, etc. It can be employed to deliver desired regulators or any protein to a desired place on a genome of a microbe, thus permitting one to tailor the attributes of the microbiome of an individual to promote the health thereof. Because CRISPR-Cas acts before transcription occurs, it is able to be employed to target regulatory and other elements on the DNA of microbes that make up the microbiome.

Thus, in certain embodiments the present invention is directed to delivering to microbial cells in vivo a delivery vehicle with at least one nucleic acid encoding a gene or nucleotide sequence of interest, such method employing an RNA-guided nuclease. The microbial cells may be either or both pathogenic microbial cells or non-pathogenic bacterial cells and the gene or nucleotide sequence of interest may be a virulence factor gene, a toxin gene, an antibiotic resistance gene, or a modulatory gene, and most preferably the nucleotide sequence of interest comprises 16S ribosomal DNA (rDNA). Preferably the delivery vehicle is a bacteriophage. After assessing what particular microbes are present in a sample, the appropriate processing of such microbes using CRISPR-Cas to delete undesired genetic elements or features is relatively straightforward (especially in view of the guidance provided herein and in conjunction with the references incorporated herein by reference.)

It has been observed by the present inventor that producing Haiku resembles the generation of a patent claim. There is requisite structure, a need to communicate substance and an ethereal quality of understanding. As one of skill in the art of both biology and Haiku will appreciate a cancer treatment that includes:

Selective killing
of your microbiome bugs
using CRISPR-Cas!

The foregoing has outlined rather broadly various pertinent and important features of various embodiments of the present invention. Such description is, however, not to be considered as limiting the invention in any way. The invention is capable of other embodiments and of being practiced and carried out in various ways which will become obvious to those skilled in the art who read this specification. Also, it is to be understood that the phraseology and terminology employed herein are for the purpose of description and should not be regarded as limiting of the invention in any fashion.

While specific embodiments and applications of the present invention have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention. Those skilled in the art will appreciate that the conception upon which this disclosure is based, may readily be utilized as a basis for designing of other structures, methods and systems for carrying out the several purposes of the present invention. It is important, therefore, that the claims be regarded as including any such equivalent construction insofar as they do not depart from the spirit and scope of the present invention.

What is claimed is:

1. A method for treating an individual suffering from a chronic infectious disease and who has cancer, comprising, using a clustered regularly interspaced short palindromic repeats (CRISPR) CRISPR associated protein (Cas), selectively killing a pathogenic bacteria within the individual, said pathogenic bacteria selected from the group consisting of *Staphylococcus aureus; Pseudomonas aeruginosa; Klebsiella; Streptoccocus; Salmonella; Shigella; Mycobacterium tuberculosis; Enterococcus; E coli; Clostridium; Neisseria* gonnorrhoea; *Acinetobacter baumannii;* and *Campylobacter,* and enhancing the growth of a beneficial bacteria in the individual selected from the group consisting of *Akkermansia, Bacteroides, Bifidobacterium, Clostridium, Enterococcus, Fusobacterium, Coprococcus, Lactobacillus, Propionibacterium, Ruminococcus, Veillonella, Prevotella,* and *Streptococcus* bacteria; wherein said CRISPR Cas system comprises Cas3 and is delivered using a bacteriophage.

2. The method as set forth in claim 1, wherein the cancer comprises colorectal or bladder cancer.

3. The method as set forth in claim 1, further comprising administering to the individual an immune checkpoint inhibitor selected from the group consisting of nivolumab, pembrolizumab, pidilizumab, AMP-224, AMP-514, STI-A1110, TSR-042, RG-7446, BMS-936559, MEDI-4736, MSB-0020718C, AUR-012 and STI-A1010.

4. The method as set forth in claim 1, wherein using the CRISPR-Cas system, said pathogenic bacteria are killed while sparing other commensal bacteria.

5. The method as set forth in claim 1, wherein the pathogenic bacteria comprises *Klebsiella pneumoniae.*

6. The method as set forth in claim 1, wherein the CRISPR-Cas system is used to reduce virulence factors of the pathogenic bacteria.

7. A method for treating an individual suffering from a chronic infectious disease and who has cancer, comprising, using a clustered regularly interspaced short palindromic repeats (CRISPR) CRISPR associated protein (Cas) system or a CRISPR from *Prevotella* and *Francisella* 1 (Cpf1), selectively killing pathogenic bacteria within the individual, said pathogenic bacteria comprising at least one of *Staphylococcus aureus; Pseudomonas aeruginosa; Klebsiella; Streptoccocus; Salmonella; Shigella; Mycobacterium tuberculosis; Enterococcus; E coli; Clostridium; Neisseria* gonnorrhoea; *Acinetobacter baumannii;* and *Campylobacter*; and administering to the individual an immune checkpoint inhibitor that specifically binds to an immune checkpoint protein selected from the group consisting of CTLA4, PD-1, PD-L1, PD-L2, A2AR, B7-H3, B7-H4, BTLA, KIR, LAG3, TIM-3 and VISTA.

8. The method as set forth in claim 7, wherein the immune checkpoint inhibitor is selected from the group consisting of nivolumab, pembrolizumab, pidilizumab, AMP-224, AMP-514, STI-A1110, TSR-042, RG-7446, BMS-936559, MEDI-4736, MSB-0020718C, AUR-012 and STI-A1010.

9. The method as set forth in claim 7, wherein the CRISPR-Cpf1 system is used to cut a gene expressed by the pathogenic bacteria.

10. The method as set forth in claim 7, wherein the CRISPR-Cas or Cpf1 system is used to insert genes that have controllable elements such that the pathogenic bacteria cells are killed by triggering the expression of said inserted genes.

11. The method as set forth in claim 7, wherein the CRISPR-Cas system or Cpf1 system is delivered by a bacteriophage.

12. The method as set forth in claim 7, wherein said pathogenic bacteria comprises at least one of *Enterobacter aerogenes, Acinetobacter baumannii,* and *Klebsiella pneumoniae.*

13. The method of claim 7, further comprising enhancing the growth of a beneficial bacteria in the individual selected from the group consisting of *Akkermansia, Bacteroides, Bifidobacterium, Clostridium, Enterococcus, Fusobacterium, Coprococcus, Lactobacillus, Propionibacterium, Ruminococcus, Veillonella, Prevotella,* and *Streptococcus* bacteria.

14. The method as set forth in claim 7, wherein the CRISPR-Cas or Cpf1 system is used to cut a gene expressed by the pathogenic bacteria.

15. The method as set forth in claim 7, wherein CRISPR-Cas or Cpf1 is used to insert antibacterial sensitivity into the genome of said pathogenic bacteria such that the pathogenic bacteria can selectively be killed.

16. The method as set forth in claim 7, wherein CRISPR-Cas or Cpf1 is used to facilitate RNA-guided site-specific DNA cleavage to kill the pathogenic bacteria.

17. The method as set forth in claim 7, wherein using CRISPR-Cas systems, said pathogenic bacteria are killed while sparing other commensal bacteria.

18. The method as set forth in claim 7, wherein using one of a CRISPR-Cas or Cpf1 system, said pathogenic bacteria are modified to reduce virulence factors of said pathogenic bacteria.

19. A method for treating an individual suffering from a chronic infectious disease and cancer, comprising, using a clustered regularly interspaced short palindromic repeats (CRISPR) CRISPR associated protein (Cas) system from *Prevotella* and *Francisella* 1 (Cpf1), selectively killing a pathogenic bacteria within the individual, said pathogenic bacteria selected from the group consisting of: *Staphylococcus aureus; Pseudomonas aeruginosa; Klebsiella; Streptoccocus; Salmonella; Shigella; Mycobacterium tuberculosis; Enterococcus; E coli; Clostridium; Neisseria* gonnorrhoea; *Acinetobacter baumannii*; and *Campylobacter*, wherein the CRISPR-Cpf1 system is used to cut a gene expressed by the pathogenic bacteria;

wherein the CRISPR-Cpf1 system is used to facilitate RNA-guided site-specific DNA cleavage to kill the pathogenic bacteria;

wherein using the CRISPR-Cpf1 system said pathogenic bacteria are killed while sparing other commensal bacteria; and wherein the CRISPR-Cpf1 system is delivered to the pathogenic bacteria using a bacteriophage.

20. The method as set forth in claim 19, wherein the CRISPR-Cpf1 system is used to insert genes that have controllable elements such that the pathogenic bacteria cells are killed by triggering the expression of said inserted genes.

* * * * *